(12) United States Patent
Babuka et al.

(10) Patent No.: US 8,821,879 B2
(45) Date of Patent: Sep. 2, 2014

(54) ANTI-BOTULISM ANTIBODY COFORMULATIONS

(75) Inventors: Susan Joyce Babuka, Berkeley, CA (US); Mingxiang Li, Berkeley, CA (US)

(73) Assignee: XOMA Technology Ltd., Berkeley, CA (US)

( * ) Notice: Subject to any disclaimer, the term of this patent is extended or adjusted under 35 U.S.C. 154(b) by 472 days.

(21) Appl. No.: 12/875,065

(22) Filed: Sep. 2, 2010

(65) Prior Publication Data

US 2012/0121581 A1 May 17, 2012

Related U.S. Application Data

(60) Provisional application No. 61/240,149, filed on Sep. 4, 2009.

(51) Int. Cl.
*A61K 39/40* (2006.01)
(52) U.S. Cl.
CPC ...................................... *A61K 39/40* (2013.01)
USPC ...................................... 424/164.1; 530/389.5
(58) Field of Classification Search
CPC ..... A61K 39/08; A61K 39/40; A61K 47/183; A61K 2039/507; A61K 2121/00; C07K 16/1282
See application file for complete search history.

(56) References Cited

U.S. PATENT DOCUMENTS

| | | | |
|---|---|---|---|
| 5,851,524 | A | 12/1998 | Beliard et al. |
| 6,261,790 | B1 | 7/2001 | O'Rourke |
| 6,849,259 | B2 | 2/2005 | Haurum et al. |
| 2003/0138417 | A1 | 7/2003 | Kaisheva et al. |
| 2004/0018198 | A1 | 1/2004 | Gudas et al. |
| 2006/0121042 | A1 | 6/2006 | Dall'Acqua et al. |
| 2008/0071063 | A1 | 3/2008 | Allan et al. |
| 2008/0112953 | A1* | 5/2008 | McAuley et al. .......... 424/133.1 |
| 2008/0124328 | A1 | 5/2008 | Marks et al. |
| 2011/0059079 | A1 | 3/2011 | Babuka et al. |

FOREIGN PATENT DOCUMENTS

| | | |
|---|---|---|
| EP | 0402029 A2 | 12/1990 |
| WO | 9801476 A1 | 1/1998 |
| WO | 2005016232 A2 | 2/2005 |
| WO | 2005118644 A2 | 12/2005 |
| WO | 2006007853 A2 | 1/2006 |
| WO | WO 2006/029224 | 3/2006 |
| WO | 2006112838 A1 | 10/2006 |
| WO | 2007094754 A2 | 8/2007 |
| WO | WO 2007/092772 | 8/2007 |
| WO | 2007143004 A2 | 12/2007 |
| WO | WO 2008/045373 | 4/2008 |
| WO | 2008068246 A1 | 6/2008 |
| WO | 2008104183 A2 | 9/2008 |
| WO | 2008118691 A2 | 10/2008 |
| WO | 2009008916 A2 | 1/2009 |
| WO | 2009105150 A2 | 8/2009 |
| WO | 2010014854 A2 | 2/2010 |
| WO | 2011028961 A2 | 3/2011 |
| WO | 2011028962 A1 | 3/2011 |

OTHER PUBLICATIONS

Daugherty & Mrsny, Adv. Drug Delivery Rev. 2006; 58:686-706.*
Bakker, A.B.H. et al., "Novel Human Monoclonal Antibody Combination Effectively Neutralizing Natural Rabies Virus Variants and Individual in Vitro Escape Mutants" J.Virol. 2005, 79(14):9062-68.
de Kruif, J. et al., "A Human Monoclonal Antibody Cocktail as a Novel Component of Rabies Postexposure Prophylaxis" Ann.Rev. Medicine, 2007, 58:359-368.
Eren, R. et al., "Preclinical Evaluation of Two Neutralizing Human Monoclonal Antibodies against Hepatitis C Virus (HCV): a Potential Treatment to Prevent HCV Reinfection in Liver Transplant Patients" J.Virol. 2006, 80(6):2654-2664.
Goudsmit, J. et al., "Comparison of an Anti-Rabies Human Monoclonal Antibody Combination with Human Polyclonal Anti-Rabies Immune Globulin" JID 2006, 193:796-801.
Haurum, J and Bregenholt, S. "Recombinant Polyclonal Antibodies: Therapeutic Antibody Technologies Come Full Circle" IDrugs 2005, 8(5):404-409.
Kontsek, L et al. "Enhancement of Neutralizing Efficacy by Combining Three Monoclonal Antibodies to Human Interferon-Alpha" Immunology 1991, 73:8-11.
Logtenberg, T. "Antibody Cocktails: Next-Generation Biopharmaceuticals with Improved Potency" Trends in Biotech 2007, 25(9):390-394.
Manning, C. et al., "Stability of Protein Pharmaceuticals" Pharm.Res 1989, 6(11):903-918.
Montero-Julian, F.A. et al., "Pharmacokinetic Study of Anti-interleukin-6 (IL-6) Clearance by Cocktails of anti-IL-6 Antibodies" Blood 1995, 85:917-924.
Nahta, R. et al., "The HER-2-Targeting Antibodies Trastuzumab and Pertuzumab Synergistically Inhibit the Survival of Breast Cancer Cells" Cancer Research 2004, 64:2343-2346.
Nowakowski, A. et al., "Potent Neutralization of Botulinum Neurotoxin by Recombinant Oligoclonal Antibody" PNAS 2002

(56) References Cited

OTHER PUBLICATIONS

Xu, W. et al., "Passive Immunization with Human Neutralizing Monoclonal Antibodies: Correlates of Protective Immunity against HIV" Vaccine, 2002, 20:1956-1960.

Zheng, J. and Janis, L., "Influence of pH, buffer species, and storage temperature on physicochemical stability of a humanized monoclonal antibody LA298" Int'l Jrl Pharma 2006, 308:46-51.

International Search Report dated Nov. 24, 2010 for International Application No. PCT/US10/047753.

Chi, et al., Physical stability of proteins in aqueous solution: mechanism and driving forces in nonnative protein aggregation. Pharm Res., 2003, 20(9):1325-36.

Cleland, et al., The development of stable protein formulations: a close look at protein aggregation, deamidation, and oxidation. Crit. Rev. Ther. Drug Carrier Syst. 1993, 10(4):307-77.

Reubsaet, et al., Analytical techniques used to study the degradation of proteins and peptides: chemical instability. J Pharm Biomed Anal. 1998, 17(6-7):955-78.

Wang, W., Lyophilization and development of solid protein pharmaceuticals. Int. J. Pharm. 2000, 203(1-2):1-60.

Arnon, Clinical trial of human botulism immune globulin, in B. R. Das Gupta (ed.), Botulinum and Tetanus Neurotoxins: Neurotransmission and Biomedical Aspects. Plenum Press, New York, 1993, 477-482.

Black and Gunn, Hypersensitivity Reactions Associated with Botulinal Antitoxin, Am J Med. 1980, 69: 567-570.

Franz, et al., Botulinum and Tetanus Neurotoxins: Neurotransmission and Biomedical Aspects, in B. R. DasGupta (ed.) Plenum Press, New York, 1993, 473-476.

Hibbs et al. Experience with the Use of an Investigational F(ab')2 Heptavalent Botulism Immune Globulin of Equine Origin During an Outbreak of Type E Botulism in Egypt (1996) Clin. Infect. Dis., 23: 337-340.

Kozaki, et al., Characterization of *Clostridium botulinum* Type B Neurotoxin Associated with Infant Botulism in Japan. Infect. Immun. 1998, 66(10): 4811-4816.

Kozaki, et al., Immunological characterization of the neurotoxin produced by *Clostridium botulinum* type A associated with infant botulism in Japan, Microbiol. Immunol., 1995, 39:767-774.

International Search Report dated Apr. 29, 2011 for International Application No. PCT/US10/047752.

European Search Report of European Patent Application 10814532.7 dated Mar. 15, 2013.

Non-Final Office Action in U.S. Appl. No. 12/875,083, mailed May 1, 2014, 12 pages.

\* cited by examiner

% Clip by SEC-HPLC
3XmAb BoNT-A through 12 months

FIG. 7

% Aggregate by SEC-HPLC for ABT02, ABT03 and ABT02/03 Mixture Formulations at pH 6.0

FIG. 8

Light Scattering by A350
3XMAb BoNT-A through 6 Months

Absorbance at 280nm
3XMAb BoNT-A through 6 Months

% Cleaved by SEC-HPLC
3XMAb BoNT-A through 6 Months

% Aggregate by SEC-HPLC
3XMAb BoNT-A through 6 Months

BoNT/B Mix
MAu Total Peak Area by
SEC-HPLC

BoNT/B Mix
% Aggregate by SEC-HPLC

BoNT/B Mix
% Truncated by SEC-HPLC

FIG. 25

BoNT/B Mix
Acidic Species Summary

BoNT/E Mix
% Remaining by SEC TPA

FIG. 29

BoNT/E
% Aggregate by SEC-HPLC

FIG. 30

BoNT/E Mix
A350 Light Scattering

FIG. 31

BoNT/E Mix
A280 protein concentration measurement

ANTI-BOTULISM ANTIBODY COFORMULATIONS

CROSS REFERENCE TO RELATED APPLICATION

This application claims the benefit under 35 U.S.C. §119(e) of U.S. Provisional Ser. No. 61/240,149, filed Sep. 4, 2009, the content of which is incorporated by reference in its entirety.

STATEMENT OF GOVERNMENT SUPPORT

The invention was made with Government support under contract number HHSN266200600008C awarded by the National Institutes of Health. The Government has certain rights in the invention.

FIELD OF INVENTION

This invention relates generally to protein-based pharmaceutical compositions, more particularly to stable formulations of multiple anti-botulism antibodies.

BACKGROUND OF THE INVENTION

Botulism is caused by botulinum neurotoxin secreted by members of the genus *Clostridium* and is characterized by flaccid paralysis, which if not immediately fatal, requires prolonged hospitalization in an intensive care unit and mechanical ventilation. Naturally occurring botulism is found in infants or adults whose gastrointestinal tracts become colonized by Clostridial bacteria (infant or intestinal botulism), after ingestion of contaminated food products (food botulism), or in anaerobic wound infections (wound botulism) (Center for Disease Control (1998) Botulism in the United States, 1899-1998. Handbook for epidemiologists, clinicians, and laboratory workers. Atlanta, Ga. U.S. Department of Health and Human Services, Public Health Service: downloadable at www.bt.cdc.gov/agent/botulism/index.asp). Botulism neurotoxins (BoNTs) are also classified by the Centers for Disease Control (CDC) as one of the six highest-risk threat agents for bioterrorism (the "Category A agents"), due to their extreme potency and lethality, ease of production and transport, and need for prolonged intensive care (Arnon et al. (2001) JAMA 285: 1059-1070). Both Iraq and the former Soviet Union produced BoNT for use as weapons (United Nations Security Council (1995) Tenth report of the executive committee of the special commission established by the secretary-general pursuant to paragraph 9(b)(I) of security council resolution 687 (1991), and paragraph 3 of resolution 699 (1991) on the activities of the Special Commission; Bozheyeva et al. (1999) Former Soviet biological weapons facilities in Kazakhstan: past, present, and future. Center for Nonproliferation Studies, Monterey Institute of International Studies), and the Japanese cult Aum Shinrikyo attempted to use BoNT for bioterrorism (Arnon et al. (2001) supra). As a result of these threats, specific pharmaceutical agents are needed for prevention and treatment of intoxication.

No therapies are available for prevention or treatment of botulism, and only an investigational pentavalent toxoid vaccine is available from the CDC (Siegel (1988) J. Clin. Microbiol. 26: 2351-2356) and a recombinant vaccine is under development (Smith (1998) Toxicon 36: 1539-1548). Regardless, mass civilian or military vaccination is unlikely due to the rarity of disease or exposure and the fact that vaccination would prevent subsequent medicinal use of BoNT. Post-exposure vaccination is useless, due to the rapid onset of disease. Toxin neutralizing antibody (Ab) can be used for pre- or post-exposure prophylaxis or for treatment (Franz et al. (1993) pp. 473-476 In B. R. DasGupta (ed.), Botulinum and Tetanus Neurotoxins: Neurotransmission and Biomedical Aspects. Plenum Press, New York). Small quantities of both equine antitoxin and human botulinum immune globulin exist and are currently used to treat adult (Black and Gunn. (1980)/ii. J. Med., 69: 567-570; Hibbs et al. (1996) Clin. Infect. Dis., 23: 337-340) and infant botulism (Arnon (1993) Clinical trial of human botulism immune globulin., pp. 477-482. In B. R. DasGupta (ed.), Botulinum and Tetanus Neurotoxins: Neurotransmission and Biomedical Aspects. Plenum Press, New York) respectively.

Recombinant monoclonal antibody (mAb) could provide an unlimited supply of antitoxin free of infectious disease risk and not requiring human donors for plasmapheresis. Given the extreme lethality of the BoNTs, mAbs must be of high potency in order to provide an adequate number of doses at reasonable cost. The development of such mAbs has become a high priority research aim of the National Institute of Allergy and Infectious Diseases. While to date no single highly potent mAbs have been described, it has been reported that combining two to three mAbs could yield highly potent BoNT neutralization (Nowakowski et al. (2002) Proc. Natl. Acad. Sci. USA, 99: 11346-50).

The development of mAb therapy for botulism is complicated by the fact that there are at least seven BoNT serotypes (A-G) (Hatheway (1995) Curr. Top. Microbio. Immunol, 195: 55-75.) that show little, if any, antibody cross-reactivity. While only four of the BoNT serotypes routinely cause human disease (A, B, E, and F), there has been one reported case of infant botulism caused by BoNT/C (Oguma et al. (1990) Lancet 336: 1449-1450), one outbreak of foodborne botulism linked to BoNT/D (Demarchi, et al. (1958) Bull. Acad. Nat. Med., 142: 580-582), and several cases of suspicious deaths where BoNT/G was isolated (Sonnabend et al. (1981) J. Infect. Dis., 143: 22-27). Aerosolized BoNT/C, D, and G have also been shown to produce botulism in primates by the inhalation route (Middlebrook and Franz (1997) Botulinum Toxins, chapter 33. In F. R. Sidell, E. T. Takafuji, D. R. Franz (eds.), Medical Aspects of Chemical and Biological Warfare. TMM publications, Washington, D.C), and would most likely also affect humans. Thus it is likely that any one of the seven BoNT serotypes can be used as a biothreat agent.

Variability of the BoNT gene and protein sequence within serotypes has also been reported and there is evidence that such variability can affect the binding of monoclonal antibodies to BoNT/A (Kozaki et al. (1998) Infect. Immun. 66: 4811-4816; Kozaki et al. (1995) Microbiol. Immunol. 39: 767-774).

Antibodies for treatment or prevention of botulism must be able to protect against the major forms of botulinum toxin (A, B, and E) (Simpson (1996) Annas Internal Med. 125 (7):616-7). They also must have high potency to provide an adequate number of doses at reasonable cost. Together with the anti-BoNT/A antibodies, antibodies to BoNT/B and BoNT/E could provide protection against all of the major forms of botulism.

Although a large number of antibodies binding different epitopes on BoNTs have been examined, potent toxin neutralization by a single antibody has not been observed. As demonstrated for BoNT/A toxin, extremely potent neutralization of BoNTs B and E toxins can be achieved by combining antibodies to generate mixtures, typically of three antibodies, which act in a synergistic manner to potently neutralize these toxins. A putative requirement for antibody synergy to occur is that the antibodies bind different toxin epitopes so that multiple antibodies can be attached to BoNT leading to rapid Fc-mediated systemic clearance. Multiple antibodies have a higher probability of being bound to BoNT when the affinity of each individual antibody for BoNT is high.

Thus, the prevention and treatment of botulism may particularly benefit from the development of a formulation containing multiple antibodies. However, for the reasons described below, stable formulations containing multiple antibodies have yet to be realized.

Because proteins are larger and more complex than traditional organic and inorganic drugs (i.e. possess multiple functional groups in addition to complex three-dimensional structures), the formulation of such proteins can be problematic. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (i.e. any process which involves modification of the protein by bond formation or cleavage resulting in a new chemical entity) or physical instability (i.e. changes in the higher order structure of the protein). Chemical instability may be caused by deamidation, racemization, hydrolysis, oxidation, beta elimination or disulfide exchange. Physical instability may be caused by denaturation, aggregation, precipitation or adsorption, for example. The three most common protein degradation pathways are protein aggregation, deamidation and oxidation (Cleland et al. (1993) Critical Reviews in Therapeutic Drug Carrier Systems 10 (4):307-377).

Antibody molecules, as part of the group of protein pharmaceuticals, are very susceptible to physical and chemical degradation, such as denaturation and aggregation, deamidation, oxidation and hydrolysis. Protein stability is influenced by the characteristics of the protein itself, e.g. the amino acid sequence, and by external influences, such as temperature, solvent pH, excipients, interfaces, or shear rates. It is thus important to define the optimal formulation conditions to protect the protein against degradation reactions during manufacturing, storage and administration (Manning et al. (1989) Pharm. Res. 6 (11): 903-18).

Most pharmaceutical antibody compositions may comprise single monoclonal antibodies such as HERCEPTIN®, HUMIRA® etc. In some instances, administration of multiple monoclonal antibodies directed to a single target or multiple targets and administrated in combination may improve their diagnostic or therapeutic indication and efficacy. For example, in a collagen-induced arthritis model, an anti-TNFα antibody was shown to be more effective in combination with either an anti-IL-1R antibody or an anti-CD4 antibody (Williams et al. (2000) J. Immunol. 2000, 165:7240-45). Cocktails of three or more antibodies binding simultaneously to a cytokine e.g. IL-6, interferon-α have been proposed as a means of enhancing clearance of a target molecule overcoming the problem of accumulation of monomeric immune complexes (Montero-Julian et al. (1995) Blood 85 (4):917-24; Kontsek et al. (1991) Immunol. 73:8-11). For some indications, such as infectious diseases, multiple antibodies that target different epitopes on a single target or different targets (for example, different toxins or infectious agent or different subtypes of the same toxin) may be necessary to achieve therapeutic efficacy. Oligoclonal cocktails comprising multiple monoclonal antibodies have been described (reviewed in Logtenberg (2007) Trends in Biotechnol. 25 (9):390-94) but are generally limited by their short-term stability. For example U.S. Pat. No. 6,262,790 describes a cocktail of two monoclonal antibodies directed to different conserved epitopes on prion proteins reportedly having broad reactivity to PrP proteins in spite of interspecies and intraspecies variation. Other examples include two—antibody cocktails for rhesus D or Idiopathic Thrombocytopenic Purpura (ITP) (U.S. Pat. No. 5,851,524; symphogen.com), rabies (Bakker et al. (2005) J. Virol. 79 (14):9062-68; de Kruif et al. (2007) Annu Rev. Med. 58:359-68; International Patent Publ. Nos. WO 05/118644 and WO 08/068,246), hepatitis C (Eren et al. (2006) J. Virol. 80: 2654-64), hepatitis B (International Patent Publ. No. WO 06/112838), Shiga toxin (International Patent Publ. No. WO 07/143,004), EGF-R-positive cancers (International Patent Publ. No. WO 08/104,183) and breast cancer (Nahta et al. (2004) Cancer Res. 64: 2343-46); three-antibody cocktails for HIV (Xu et al. (2002) Vaccine 20: 1956-60) and botulinum neurotoxin type A (BoNT/A) (Nowakowski et al. (2002) Proc. Natl. Acad. Sci. USA 99 (17): 11346-50; International Patent Publ. No. WO 2005/016232); and a five-antibody cocktail for rabies (European Patent Publ. No. EP 0 402 029). Approaches for producing recombinant polyclonal antibodies have also been described (Haurum & Bregenholt (2005) IDrugs 8 (5):404-409, Rasmussen et al. (2007) Biotechnol. Lett. 29: 845-52; International Patent Publ. No. WO 06/007853). International Patent Publ. No. WO 98/01476 describes mixtures of polyclonal and monoclonal anti-HIV antibodies.

The stabilization of polypeptides in pharmaceutical compositions remains an area in which trial and error plays a major role (reviewed by Wang (1999) Int. J. Pharm. 185:129-88). Numerous factors can be varied in order to find suitable excipients and optimal conditions for preparing a long-term stable formulation for a single monoclonal antibody, making this a challenging process. Stably formulating two different antibodies in a single formulation is even more problematic and involves choosing excipients and conditions that represent a compromise. These difficulties are compounded for formulating three antibodies, or more.

The development of a stable formulation for multiple antibodies also requires determination of stability and degradation of the individual antibodies present in the antibody mixture. Such a determination is often difficult due to the large number of antibodies in the formulation and their similarities.

This invention addresses and overcomes these difficulties and provides related advantages as well.

SUMMARY OF THE INVENTION

It has now been discovered that stable pharmaceutical formulations can be prepared for multiple antibodies directed to botulinum neurotoxins (BoNT). One aspect of the invention provides a stable pharmaceutical formulation comprising, or alternatively consisting essentially of, or yet alternatively consisting of, a plurality of antibodies directed to at least one serotype of BoNT, an effective amount of a succinate buffer, and an effective amount of arginine, wherein the plurality of antibodies are present in substantially equal concentrations, and the pH of the formulation is between about 4.5 and about 7. In some embodiments, the pH of the formulation is between about 4.5, 4.6, 4.7, 4.8, 4.9, or 5.0 and about 6.5, 6.6, 6.7, 6.8, 6.9, or 7.0 and is not detrimental to any of the plurality of antibodies in the formulation. In some embodiments, the pH of the formulation is between about 5 and about 6.5, or alternatively between about 5.5 and about 6.5, or alternatively between about 5.5 and 6, or alternatively between about 6 and 6.5. In some embodiments, the pH of the formulation is at about 5.5, or alternatively about 6, or alternatively about 6.5.

Examples of antibodies that can be used in the formulation of the current invention are described herein.

In some embodiments, the formulation further comprises, or alternatively consists essentially of, or yet further consists of an effective amount of a tonicity agent that is not arginine. The tonicity agent can be one or more of sodium chloride, potassium chloride, glycerin, an amino acid or sugar. In a particular aspect, the tonicity agent is an amino acid, e.g., methionine, glycine or alanine.

In some embodiments, the formulation further comprises or alternatively consists essentially of, or yet further consists of an effective amount of a surfactant. The surfactant can be one or more of a polyoxyethylensorbitan fatty acid ester, a polyoxyethylene alkyl ether, an alkylphenylpolyoxyethylene ether, a polysorbate, a polyoxyethylene-polyoxypropylene copolymer or a sodium dodecyl sulphate. In a particular aspect, the surfactant is a polysorbate, e.g. Tween 20 or Tween 80.

In some embodiments, the formulation further comprises or alternatively consists essentially of, or yet further consists of an effective amount of a stabilizer and/or a cryoprotectant and/or a lyoprotecant. The stabilizer can be one or more of a sugar, an amino acid, a polyol, a surfactant, an antioxidant, a preservative, a cyclodextrine, a polyethyleneglycol, albumin or a salt.

In one aspect of the above embodiments, the plurality of the stable pharmaceutical formulation of the invention comprises or alternatively consists essentially of, or yet further consists of at least three antibodies, or at least four, or at least five antibodies. In another aspect, the plurality of antibodies comprise at least three antibodies for each BoNT serotype.

In another aspect of the above embodiments, the plurality of antibodies are present in substantially equal concentration in the formulation. In some embodiments, at least one of the plurality of antibodies is a monoclonal antibody, or a human antibody or a humanized antibody or a chimeric antibody.

In further another aspect of the above embodiments, the plurality of antibodies have isoelectric points from about 6 to about 10. In another aspect, the plurality of antibodies have isoelectric points from about 7 to about 9.5. In yet another aspect, the maximum of the isoelectric points is at least about 2.5 higher than the minimum of the isoelectric points, or alternatively the maximum of the isoelectric points is at least about 1.5 higher than the minimum of the isoelectric points.

In further another aspect of the above embodiments, the plurality of antibodies are present in concentrations from about 0.1 mg/mL to about 100 mg/mL. In another aspect, the plurality of antibodies are present in concentrations from about 1 mg/mL to about 5 mg/mL.

In yet another aspect of the above embodiments, the plurality of antibodies are detectably or therapeutically labeled.

The coformulation is not limited by the specificity of the antibodies. In one aspect, at least two of the plurality of antibodies specifically recognize and bind the same BoNT serotype.

In another aspect, at least two of the plurality of antibodies can specifically recognize and bind different epitopes of the same BoNT serotype. In yet another aspect, at least two of the plurality of antibodies can specifically recognize and bind different BoNT serotype. In some embodiments, the BoNT serotype is BoNT/A, or alternatively BoNT/B, or alternatively BoNT/E, or alternatively combinations thereof.

The formulations of the current invention can be stable at about room temperature for at least 30 days, or alternatively stable at a temperature from about 2.0° C. to about 8.0° C. for at least about a year, or alternatively stable for at least about two years or three years or five years at a temperature from about 2.0° C. to about 8.0° C., or alternatively stable for at least about two years at a temperature of about 5° C. In some embodiments, the formulations of the current invention are stable at about 25° C. for up to a year, or alternatively for up to two or three years. In some embodiments, the formulations of the current invention are stable at about 40° C. for up to three months, or alternatively for up to six months. In some embodiments, the formulations are stable at about −20° C. for up to one year, of alternatively two years, three years, four years, or five years. In some embodiments, the formulations are stable at about −80° C. for up to one year, of alternatively two years, three years, four years, or five years. In some embodiments, the formulation is lyophilized or frozen.

In some embodiments, the formulation of the current invention is physically stable. In some embodiments, the formulation of the current invention is chemically stable. In some embodiments, the formulation of the current invention is biologically stable.

Also provided is a method for preparing the stable pharmaceutical formulation of the invention as described above, comprising, or alternatively consisting essentially of, or alternatively consisting of, admixing a plurality of anti-BoNT antibodies, an effective amount of a succinate buffer, an effective amount of arginine, to a pH between about 4.5 and about 7 and variations in between as described herein.

In one aspect of the method, the plurality of antibodies of the stable pharmaceutical formulation comprises or alternatively consists essentially of, or yet further consists of at least three antibodies, or at least four, five, six, seven, eight or nine antibodies.

In one aspect of the method, the plurality of antibodies comprise at least three antibodies for each BoNT serotype. In some embodiments, at least one of the plurality of antibodies is a monoclonal antibody, or a human antibody or a humanized antibody or a chimeric antibody.

In yet another aspect of the method, at least two of the plurality of antibodies specifically recognize and bind the same BoNT serotype. In another aspect, at least two of the plurality of antibodies can specifically recognize and bind different epitopes of the same BoNT serotype. In yet another aspect, at least two of the plurality of antibodies can specifically recognize and bind different BoNT serotype. In some embodiments, the BoNT serotype is BoNT/A, or alternatively BoNT/B, or alternatively BoNT/E, or alternatively combinations thereof.

In some embodiments, the method further comprises, or alternatively consists essentially of, or yet further consists of admixing an effective amount of a tonicity agent other than arginine to the formulation described above. The tonicity agent can be at least one of sodium chloride, potassium chloride, glycerin, an amino acid or sugar. In a particular aspect, the tonicity agent is an amino acid, e.g., methionine or glycine or alanine.

In some embodiments, the method further comprises or alternatively consists essentially of, or yet further consists of admixing an effective amount of a surfactant to the formulation. The surfactant can be at least one of a polyoxyethylensorbitan fatty acid ester, a polyoxyethylene alkyl ether, an alkylphenylpolyoxyethylene ether, a polyoxyethylene-polyoxypropylene copolymer, a polysorbate or sodium dodecyl sulphate. In a particular aspect, the surfactant is a polysorbate, e.g., Tween 20 or Tween 80.

In some embodiments, the method further comprises or alternatively consists essentially of, or yet further consists of admixing an effective amount of a stabilizer. The stabilizer can be at least one a sugar, an amino acid, a polyol, a surfactant, an antioxidant, a preservative, a cyclodextrine, a polyethyleneglycol, albumin or a salt. In a further aspect, the method further comprises adminixing an effective amount of a cryoprotectant and/or a lyoprotectant.

Another aspect of the invention provides a method for treating a subject in need of therapy, comprising, or alternatively consisting essentially of, or alternatively consisting of, administering to the subject an effective amount of the formulation of the invention, thereby treating the subject.

Yet another aspect of the invention provides a method for preventing a subject from suffering from a botulinum neurotoxin infection, comprising, or alternatively consisting essentially of, or alternatively consisting of, administering to the subject an effective amount of the formulation of the invention, thereby preventing the subject from suffering from the botulinum neurotoxin infection. In some embodiments, the subject is at risk of botulinum neurotoxin exposure or infection.

This invention also provides the use of the formulations as described herein in the preparation of a medicament, which in one aspect, is useful to treat a subject in need of antibody therapy.

BRIEF DESCRIPTION OF THE DRAWINGS

FIG. 1, panels A through C, show evaluation of stability of ABT01 40° C. stressed samples formulated in 10 mM sodium phosphate, 140 mM NaCl, at pH 5.5, 6.5, or 7.5 (A) Change in percent SEC-HPLC monomer (B) Change in percent total soluble aggregates (C) Change in percent clips.

FIG. 2 shows scattered light intensity as measured at A350 nm for ABT01 stability samples formulated in three different buffer species: sodium citrate (C2), L-histidine (H2), and sodium succinate (S2) for the indicated number of weeks (w) or months (m).

FIG. 3, panels A and B show SEC-HPLC chromatograms of ABT01 three month 40° C. (A) and 50° C. (B) samples formulated in 10 mM sodium succinate, 0.005% polysorbate 80 at pH 6.0 with three different L-arginine concentrations (2%, 3% and 4%).

FIG. 4, panels A and B show validation of the IEX-HPLC method. (A) Overall IEX-HPLC profile of the 3-antibody mixture (ABT01/02/03). Sample shown is in succinate buffer at time zero. (B) Example of IEX-HPLC time course overlay illustrating that the method is able to measure the stability of individual antibodies in a mixture.

FIG. 5 uses chromatographic overlay of succinate buffered 1:1:1 3-antibody mixture (ABT01/02/03) to illustrate the overall size-based profile. The overlays shown are time zero through 4 weeks at 50° C. illustrating that the SEC-HPLC assay is able to measure the stability of individual antibodies in a mixture.

FIG. 6A shows IEX-HPLC chromatographic overlay of the 3-antibody mixture (ABT01/02/03) comparing histidine to succinate buffered samples.

FIG. 6B shows SEC-HPLC chromatographic overlay of the 3-antibody mixture (ABT01/02/03) comparing histidine versus succinate buffered solutions showing 40° C. and 50° C. at the 4 week time point. Magnified image showing percent peak area of small and large molecular weight species.

FIG. 7 shows percent clip for the 3-antibody mixture (ABT01/02/03) stored through 12 months.

FIG. 8 shows percent aggregate by SEC-HPLC of ABT02, ABT03 and the ABT02/03 mixture formulations, all at pH 6.0.

FIG. 9A shows A350 light scattering measurements for the 3-antibody mixture (ABT01/02/03) through the six month time point for samples stored at frozen, refrigerated and room temperature.

FIG. 9B shows absorbance at 280 nm for the 3-antibody mixture (ABT01/02/03) through the six month time point for samples stored at frozen, refrigerated and room temperature.

FIG. 9C shows percent cleaved by SEC-HPLC for the 3-antibody mixture (ABT01/02/03) through the six month time point for samples stored at frozen, refrigerated and room temperature.

FIG. 9D shows percent aggregate by SEC-HPLC for the 3-antibody mixture (ABT01/02/03) through the six month time point for samples stored at frozen, refrigerated and room temperatures.

FIG. 10A shows percent aggregate for the 3-antibody mixture (ABT01/02/03) stored through 12 months at −20° C. and 5° C.

FIG. 10B shows percent cleaved species for the 3-antibody mixture (ABT01/02/03) stored through 12 months at −20° C. and 5° C.

FIG. 10C shows percent acidic species of ABT01, ABT02 and ABT03 injected from the 3-antibody mixture. Samples shown are stored at 2 to 8° C. and −20° C. through the 12 month time point.

FIG. 11 shows percent difference at 2 to 8° C. in aggregates by SEC-HPLC for the average of the individual antibody injections versus the 3-antibody mixture (ABT01/02/03).

FIG. 12A shows DSC overlay illustrating increasing thermal stability of 3-antibody mixture (ABT01/02/03) with increasing pH.

FIG. 12B shows DSC overlay of individual antibody solutions vs. 3-antibody mixture (ABT01/02/03) in succinate buffer. Melting temperature (Tm) of mixture is the average of the individual Tm's FIG. 13 shows percent acidic peaks by CEX-HPLC of the individual antibodies in the ABT1/ABT2/ABT3 antibody mixture.

FIG. 14 shows by percent the aggregation and fragmentation as measured by SEC-HPLC of the ABT1/ABT2/ABT3 antibody mixture.

FIG. 15, panels A through C, show ELISA data demonstrating the binding of (A) ABT02, (B) ABT01 and (C) ABT03 within the context of a 3-antibody mixture. Antibodies were co-formulated at a 1:1:1 ratio in 10 mM sodium succinate/succinic acid, 142 mM L-arginine, 0.005% Tween-80 at pH 6.0. and stored at 2 to 8° C. for greater than 1 week prior to testing in the assay.

FIG. 16 shows the long-term stability of the individual antibodies in the ABT1/ABT2/ABT3 antibody mixture as measured by their ELISA binding activities.

FIG. 17 shows percent remaining compared to T=0 by CEX-HPLC total peak area for ABT17 for three levels of polysorbate 80.

FIG. 18 shows A350 light scattering measurements for agitation stress samples of the BoNT/B ABT10/ABT14/ABT17 mixture.

FIG. 19 shows percent remaining of T=0 by SEC-HPLC total peak area for the BoNT/B ABT10/ABT14/ABT17 mixture.

FIG. 20 shows percent aggregate by SEC-HPLC for agitation stress samples of the BoNT/B ABT10/ABT14/ABT17 mixture.

FIG. 21 shows A350 light scattering of BoNT/B ABT10/ABT14/ABT17 mixture stored through six weeks at 5, 40 and 50° C.

FIG. 23 shows percent aggregate by SEC-HPLC of BoNT/B ABT10/ABT14/ABT17 mixture stored through six weeks at 5, 40 and 50° C.

FIG. 24 shows SEC-HPLC chromatographic overlay of BoNT/B ABT10/ABT14/ABT17 mixture stored through six weeks at 40° C.

FIG. 25 shows percent truncated by SEC-HPLC of BoNT/B ABT10/ABT14/ABT17 mixture stored through six weeks at 5, 40 and 50° C.

FIG. 26 shows percent acidic by CEX-HPLC of BoNT/B ABT10/ABT14/ABT17 mixture stored through six weeks at 5, 40 and 50° C.

FIG. 27 shows CEX-HPLC chromatographic overlay for BoNT/E ABT18/ABT19/ABT21 mixture. T=0 vs. 72H agitation, 1000 RPM.

FIG. 28 shows A350 light scattering measurements for agitation stress samples of the BoNT/E ABT18/ABT19/ABT21 mixture.

FIG. 29 shows percent remaining of T=0 by SEC-HPLC total peak area for the BoNT/E ABT18/ABT19/ABT21 mixture formulation.

FIG. 30 shows percent Aggregate by SEC-HPLC for agitation stress samples of the BoNT/E ABT18/ABT19/ABT21 mixture.

FIG. 31 shows A350 light scattering of BoNT/E ABT18/ABT19/ABT21 mixture stored through six weeks at 5, 40 and 50° C.

FIG. 32 shows A280 protein concentration measurements of BoNT/E ABT18/ABT19/ABT21 mixture stored through six weeks at 5, 40 and 50° C.

FIG. 35 shows percent truncated by SEC-HPLC of BoNT/E ABT18/ABT19/ABT21 mixture stored through six weeks at 5, 40 and 50° C.

FIG. 36 shows CEX-HPLC chromatographic overlay of BoNT/E ABT18/ABT19/ABT21 mixture shown at the T=4 week time point.

DETAILED DESCRIPTION OF THE INVENTION

I. Definitions

Figure 1:
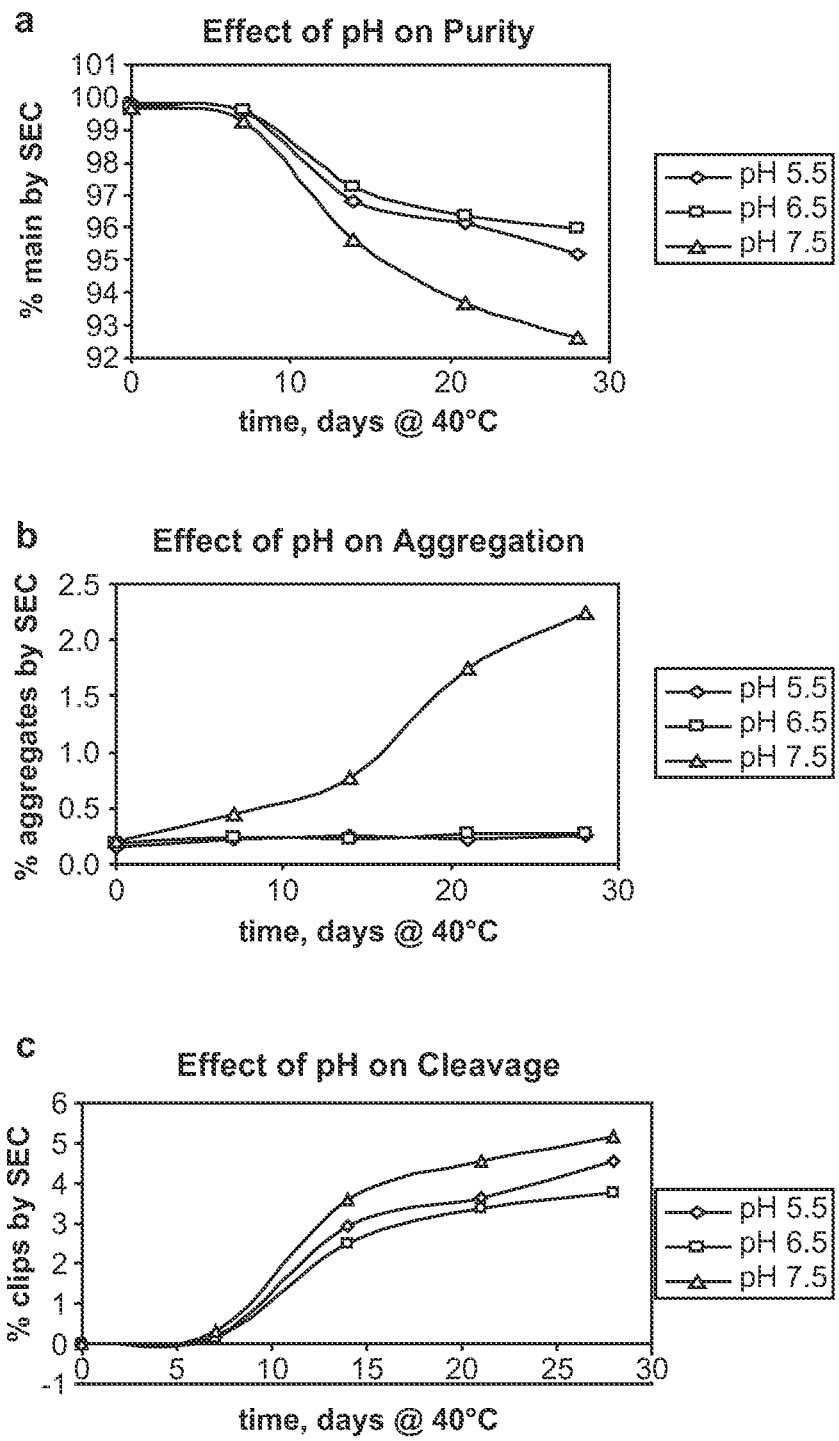

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, in a sterile composition suitable for diagnostic or therapeutic use in vitro, in vivo or ex vivo. In one aspect, the pharmaceutical composition is substantially free of endotoxins or is non-toxic to recipients at the dosage or concentration employed.

"An effective amount" refers to the amount of the defined component sufficient to achieve the desired chemical composition or the desired biological and/or therapeutic result. That result can be the desired pH or chemical or biological characteristic, e.g., stability of the formulation. In other aspects, the desired result is the alleviation of the signs, symptoms, or causes of a disease, or any other desired alteration of a biological system. When the desired result is a therapeutic response, the effective amount will vary depending upon the specific disease or symptom to be treated or alleviated, the age, gender and weight of the subject to be treated, the dosing regimen of the formulation, the severity of the disease condition, the manner of administration and the like, all of which can be determined readily by one of skill in the art.

A "subject" of diagnosis or treatment is a prokaryotic or a eukaryotic cell, a tissue culture, a tissue or an animal, e.g. a mammal, including a human. Non-human animals subject to diagnosis or treatment include, for example, a human patient, a simian, a murine, a canine, a leporid, such as a rabbit, livestock, sport animals, and pets.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of amelioration of the symptoms of the disease or infection, or a partial or complete cure for a disorder and/or adverse effect attributable to the disorder. In one aspect, the formulations containing anti-botulinum antibodies will prevent or alleviate or mitigate the symptoms of botulinum toxin in a subject.

As used herein, to "treat" further includes systemic amelioration of the symptoms associated with the pathology and/or a delay in onset of symptoms. Clinical and sub-clinical evidence of "treatment" will vary with the pathology, the individual and the treatment.

A formulation of the present invention can be administered by any suitable route, specifically by parental (including subcutaneous, intramuscular, intravenous and intradermal) administration. It will also be appreciated that the preferred route will vary with the condition and age of the recipient, and the disease being treated. Methods of determining the most effective means and dosage of administration are known to those of skill in the art and will vary with the composition used for therapy, the purpose of the therapy, and the subject being treated. Single or multiple administrations can be carried out with the dose level and pattern being selected by the treating physician. Suitable dosage formulations and methods of administering the agents are known in the art.

The formulations of the present invention can be used in the manufacture of medicaments and for the treatment of humans and other animals by administration in accordance with conventional procedures.

The term "isolated" as used herein with respect to nucleic acids, such as DNA or RNA, refers to molecules separated from other DNAs or RNAs, respectively that are present in the natural source of the macromolecule. The term "isolated" is also used herein to refer to polypeptides and proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

The term "protein" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than about 40% identity, or alternatively less than about 25%, or alternatively less than about 15%, or alternatively less than about 10% identity, with one of the sequences of the present invention.

As used herein, the term "equivalent thereof" when referring to a reference protein, polypeptide or nucleic acid, intends those having minimal homology while still maintaining desired functionality. It is contemplated that any modified protein mentioned herein also includes equivalents thereof. For example, the homology can be, at least about 75% homology and alternatively, at least about 80%, or alternatively at least about 85%, or alternatively at least about 90%, or alternatively at least about 95%, or alternatively about 98% percent homology and exhibit substantially equivalent biological activity to the reference polypeptide or protein. A polynucleotide or polynucleotide region (or a polypeptide or polypeptide region) has a certain percentage (for example, about 80%, about 85%, about 90%, or about 95%) of "sequence identity" to another sequence means that, when aligned, that percentage of bases (or amino acids) are the same in comparing the two sequences. This alignment and the percent homology or sequence identity can be determined using software programs known in the art, for example those described in Current Protocols In Molecular Biology (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

A polynucleotide or polynucleotide region (or a polypeptide or polypeptide region) has a certain percentage (for example, about 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/blast/Blast.cgi, last accessed on Nov. 26, 2007. Biologically equivalent polynucleotides are those having the specified percent homology and encoding a polypeptide having the same or similar biological activity.

A "peptide conjugate" refers to the association by covalent or non-covalent bonding of one or more polypeptides and another chemical or biological compound. In a non-limiting example, the "conjugation" of a polypeptide with a chemical compound results in improved stability or efficacy of the polypeptide for its intended purpose. In one embodiment, a peptide is conjugated to a carrier, wherein the carrier is a liposome, a micelle, or a pharmaceutically acceptable polymer.

An "isoelectric point" or "pI" refers to the pH at which an amphoteric molecule, such as an antibody, carries no net electrical charge. An amphoteric molecule contains both positive and negative charges depending on the functional groups present in the molecule. The net charge on the molecule is affected by pH of the surrounding environment and can become more positively or negatively charged due to the loss or gain of protons (H+). The pI is the pH value at which the molecule carries no electrical charge or the negative and positive charges are equal. The pI value can affect the solubility of a molecule at a given pH. Such molecules have minimum solubility in water or salt solutions at the pH which corresponds to their pI and often precipitate out of solution. Biological amphoteric molecules such as proteins contain both acidic and basic functional groups. Amino acids which make up proteins may be positive, negative, neutral or polar in nature, and together give a protein its overall charge. At a pH below their pI, proteins carry a net positive charge; above their pI they carry a net negative charge. A "theoretical pI" of a protein depends on the amino acid composition of the molecule and can be calculated with methods known in the art, e.g., with a script available on the website of biopython.org/wiki/Main_Page.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes aeukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" that usually lack a nucleus or any other membrane-bound organelles and are divided into two domains, bacteria and archaea. Additionally, instead of having chromosomal DNA, these cells' genetic information is in a circular loop called a plasmid. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *bacillus* bacteria, *E. coli* bacterium, and *Salmonella* bacterium.

As used herein, an "antibody" includes whole antibodies and any antigen binding fragment or a single chain thereof. Thus the term "antibody" includes any protein or peptide containing molecule that comprises at least a portion of an immunoglobulin molecule having biological activity of binding to the antigen. Examples of such may comprise a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "polyclonal antibody" or "polyclonal antibody composition" as used herein refer to a preparation of antibodies that are derived from different B-cell lines. A polyclonal antibody is a mixture of immunoglobulin molecules secreted against a specific antigen, recognizing the same or different epitopes of the antigen, or against different antigens.

The terms "monoclonal antibody" or "monoclonal antibody composition" as used herein refer to a preparation of antibody molecules of single molecular composition. A monoclonal antibody composition displays a single binding specificity and affinity for a particular epitope.

A "monoclonal antibody mixture" or an "oligoclonal cocktail" refers to a mixture or combination of multiple monoclonal antibodies, each of which monoclonal antibodies can specifically recognize and bind the same antigen, the same or different episodes of the antigen or different antigens.

Antibodies generally comprise two heavy chain polypeptides and two light chain polypeptides, though single domain antibodies having one heavy chain and one light chain, and heavy chain antibodies devoid of light chains are also contemplated. There are five types of heavy chains, called alpha, delta, epsilon, gamma and mu, based on the amino acid sequence of the heavy chain constant domain. These different types of heavy chains give rise to five classes of antibodies, IgA (including $IgA_1$ and $IgA_2$), IgD, IgE, IgG and IgM, respectively, including four subclasses of IgG, namely $IgG_1$, $IgG_2$, $IgG_3$ and $IgG_4$. There are also two types of light chains, called kappa (κ) or lambda (λ) based on the amino acid sequence of the constant domains. A full-length antibody includes a constant domain and a variable domain.

The constant domains are not involved directly in binding the antibody to an antigen but are involved in the effector functions (ADCC, complement binding, and CDC). Human constant domains are described in detail by Kabat et al., Sequences of Proteins of Immunological Interest, 5th Ed. Public Health Service, National Institutes of Health, Bethesda, Md. (1991), and by Bruggemann et al. (1987) J. Exp. Med. 166: 1351-1361; Love et al. (1989) Methods Enzymol. 178: 515-527. Other useful constant domains are the constant domains of the antibodies obtainable from the hybridoma cell lines deposited with depositories like Deutsche Sammlung von Mikroorganismen and Zellkulturen GmbH (DSMZ) or American Type Culture Collection (ATCC).

Each of the heavy chain and light chain sequences of an antibody, or antigen binding fragment thereof, includes a variable domain with three complementarity determining regions (CDRs) as well as non-CDR framework regions (FRs). The terms "heavy chain" and "light chain," as used herein, mean the heavy chain variable domain and the light chain variable domain, respectively, unless otherwise noted. Variable regions and CDRs in an antibody sequence can be identified (i) according to general rules that have been developed in the art or (ii) by aligning the sequences against a database of known variable regions. Methods for identifying these regions are described in Kontermann and Dubel, eds., Antibody Engineering, Springer, New York, N.Y., 2001, and Dinarello et al., Current Protocols in Immunology, John Wiley and Sons Inc., Hoboken, N.J., 2000. Databases of antibody sequences are described in and can be accessed through "The Kabatman" database at bioinf.org.uk/abs (maintained by A. C. Martin in the Department of Biochemistry & Molecular Biology University College London, London, England) and VBASE2 at vbase2.org, as described in Retter et al. (2005) Nucl. Acids Res. 33 (Database issue): D671-D674. The "Kabatman" database web site also includes general rules of thumb for identifying CDRs. The term "CDR," as used herein, is as defined in Kabat et al., Sequences of Immunological Interest, $5^{th}$ ed., U.S. Department of Health and Human Services, 1991, unless otherwise indicated.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes, by screening a human immunoglobulin gene library, or by synthesizing based on human immunoglobulin gene sequences. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least about 95%, or even at least about 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods for making these antibodies are described herein.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods for making these antibodies are described herein.

As used herein, "isotype" refers to the antibody class (e.g., IgM or IgG1) that is encoded by heavy chain constant region genes.

As used herein, the term "label" intends a directly or indirectly detectable compound or composition that is conjugated directly or indirectly to the composition to be detected, e.g., polynucleotide or protein such as an antibody so as to generate a "labeled" composition. An antibody in a formulation or in a coformulation with other coformulated antibodies can be labeled to facilitate detection or stability analysis. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6th ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Coformulated" or "coformulation" as used herein refers to antibodies being formulated together rather than being formulated and stored individually and then mixed before administration or separately administered.

As used herein, the term "excipient" refers to an inert substance which is commonly used as a diluent, vehicle, preservative, binder, or stabilizing agent for drugs and includes, but is not limited to, proteins (e.g., serum albumin, etc.), amino acids (e.g., aspartic acid, glutamic acid, lysine, arginine, glycine, histidine, alanine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). Also see Remington's Pharmaceutical Sciences (by Joseph P. Remington, 18th ed., Mack Publishing Co., Easton, Pa.) and Handbook of Pharmaceutical Excipients (by Raymond C. Rowe, 5th ed., APhA Publications, Washington, D.C.) which are hereby incorporated in its entirety. Preferably, the excipients impart a beneficial physical property to the formulation, such as increased protein stability, increased protein solubility and decreased viscosity.

The term "buffer" as used herein denotes a pharmaceutically acceptable excipient, which stabilizes the pH of a pharmaceutical preparation. Suitable buffers are well known in the art and can be found in the literature. Pharmaceutically acceptable buffers comprise but are not limited to histidine-buffers, citrate-buffers, succinate-buffers and phosphate-buffers. Independently from the buffer used, the pH can be adjusted at a value from about 4.0 to about 7.0 or alternatively from about 5.5 to about 6.5 or alternatively about 6.0 with an acid or a base known in the art, e.g., succinic acid, hydrochloric acid, acetic acid, phosphoric acid, sulfuric acid and citric acid, sodium hydroxide and potassium hydroxide. Suitable buffers include, without limitation, histidine buffer, 2-morpholinoethanesulfonic acid (MES), cacodylate, phosphate, acetate, succinate, and citrate. The concentration of the buffer can be between about 4 mM and about 60 mM, or alternatively about 4 mM to about 40 mM, or alternatively about 5 mM to about 25 mM.

"Succinate buffer" refers to a mixture of succinate salt and succinic acid with pH adjustment with an acid or a base known in the art. Examples of succinate salt include, without limitation, sodium succinate or potassium succinate. Succinate buffer can be generally used in an amount of about 1 mM to about 100 mM, or alternatively about 1 mM to about 50 mM, about 1-about 40 mM, about 2-about 40 mM, about 2-about 30 mM, about 3-about 30 mM, about 3-about 25 mM, about 4-about 25 mM, about 4-about 20 mM, about 5-about 20 mM, or alternatively from about 5 to about 15 mM. In some embodiments, the succinate buffer is used at about 5, or alternatively about 6, or alternatively about 7, or alternatively about 8, or alternatively about 9, or alternatively about 10, or alternatively about 11, or alternatively about 12, or alternatively about 13, or alternatively about 14 or alternatively about 15 mM. In some embodiments, the succinate buffer is used at about 10 mM.

"Cryoprotectants" are known in the art and include without limitation, e.g., sucrose, trehalose, and glycerol. A cryoprotectant exhibiting low toxicity in biological systems is generally used.

The term "tonicity agent" as used herein denotes pharmaceutically acceptable agents used to modulate the tonicity of the formulation. Isotonicity generally relates to the osmotic pressure relative to a solution, usually relative to that of human blood serum. A formulation can be hypotonic, isotonic or hypertonic. In one aspect, the formulation is isotonic. An isotonic formulation is liquid or liquid reconstituted from a solid form, e.g. from a lyophilized form and denotes a solution having the same tonicity as some other solution with which it is compared, such as physiologic salt solution and the blood serum. Suitable isotonicity agents include but are not limited to sodium chloride, potassium chloride, glycerin and any component from the group of amino acids, sugars, as defined herein as well as combinations thereof. Tonicity agents may be used in an amount of about 5 mM to about 500 mM, or alternatively from about 10 mM to about 450 mM, or alternatively from about 20 mM to about 400 mM, or alternatively from about 50 mM to about 300 mM, or alternatively from about 100 mM to about 200 mM, or alternatively from about 125 mM to about 175 mM. In some embodiments, one or more amino acids is present. In some embodiments the amino acid present is arginine. In some embodiments, arginine is present in a concentration of about 5 mM to about 500 mM, or alternatively from about 10 mM to about 450 mM, or alternatively from about 20 mM to about 400 mM, or alternatively from about 50 to about 300 mM, or alternatively from about 100 mM to about 200 mM, or alternatively from about 125 mM to about 175 mM. In some embodiments, arginine is present at about 120 mM, or alternatively about 125 mM, or alternatively about 130 mM, or alternatively about 135 mM, or alternatively about 140 mM, or alternatively about 141 mM, or alternatively about 142 mM, or alternatively about 143 mM, or alternatively about 144 mM, or alternatively about 145 mM, or alternatively about 150 mM, or alternatively about 160 mM or alternatively about 175 mM. In some embodiments, arginine is present at about 142 mM.

The term "liquid" as used herein denotes a formulation which is liquid at a temperature of at least about 2° C. to about 8° C. under standard pressure.

The term "stabilizer" denotes a pharmaceutical acceptable excipient, which protects the active pharmaceutical ingredient and/or the formulation from chemical and/or physical degradation during manufacturing, storage and application.

Chemical and physical degradation pathways of protein pharmaceuticals are reviewed by Cleland et al. (1993) Crit. Rev. Ther. Drug Carrier Syst. 10(4): 307-77, Wang (1999) Int. J. Pharm. 185(2): 129-88., Wang (2000) Int. J. Pharm. 203 (1-2): 1-60, and Chi et al. (2003) Pharm Res 20(9): 1325-36. Stabilizers include but are not limited to sugars, amino acids, polyols, surfactants, antioxidants, preservatives, cyclodextrines, e.g. hydroxypropyl-β-cyclodextrine, sulfobutylethyl-β-cyclodextrin, β-cyclodextrin, polyethyleneglycols, e.g. PEG 3000, 3350, 4000, 6000, albumin, e.g. human serum albumin (HSA), bovine serum albumin (BSA), salts, e.g. sodium chloride, magnesium chloride, calcium chloride, chelators, e.g. EDTA as hereafter defined. Stabilizers can be present in the formulation in an amount of about 1 mM to about 500 mM, or alternatively in an amount of from about 10 to about 300 mM, or alternatively in an amount of from about 100 mM to about 300 mM. In some embodiments, one or more amino acids is present. In some embodiments the amino acid present is arginine, methionine, glycine or alanine. In some embodiments the amino acid present is arginine. In some embodiments, arginine is present in a concentration of from about 5 mM to about 500 mM, or from about 10 mM to about 450 mM, or from about 20 mM to about 400 mM, or from about 50 mM to about 300 mM, or from about 100 mM to about 200 mM, or alternatively from about 125 mM to about 175 mM. In some embodiments, arginine is present in a concentration at around about 120 mM, or alternatively about 125 mM, or about 130 mM, or about 135 mM, or about 140 mM, or about 141 mM, or about 142 mM, or about 143 mM, or about 144 mM, or about 145 mM, or about 150 mM, or about 160 mM or about 175 mM. In some embodiments, arginine is present at about 142 mM.

As used herein, the term "surfactant" refers to a pharmaceutically acceptable organic substance having amphipathic structures; namely, it is composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. In some embodiments of the pharmaceutical formulations described herein, the amount of surfactant is described as a percentage expressed in weight/volume percent (w/v %). Suitable pharmaceutically acceptable surfactants include but are not limited to the group of polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), or sodium dodecyl sulphate (SDS). Polyoxyethylenesorbitan-fatty acid esters include polysorbate 20, (sold under the trademark Tween 20™) and polysorbate 80 (sold under the trademark Tween 80™). Polyethylene-polypropylene copolymers include those sold under the names Pluronic® F68 or Poloxamer 188™. Polyoxyethylene alkyl ethers include those sold under the trademark Brij™. Alkylphenolpolyoxyethylene ethers include those sold under the tradename Triton-X. When polysorbate 20 (Tween 20™) and polysorbate 80 (Tween 80™) are used they are generally used in a concentration range of about 0.001% w/v to about 1% w/v, or alternatively of about 0.002% w/v to about 0.1% w/v of the total volume of the formulation, or alternatively of about 0.003% w/v to about 0.007% w/v. In some embodiments, Tween 80™ is used at about 0.003% w/v, or about 0.004% w/v, or about 0.0045% w/v, or about 0.005% w/v, or about 0.0055% w/v, or about 0.006% w/v or about 0.007% w/v. In some embodiments, Tween 80™ is used at about 0.005% w/v. In this aspect, "w/v" intends the weight of surfactant per total volume of the coformulation.

A "lyoprotectant" refers to a pharmaceutically acceptable substance that stabilizes a protein during lyophilization (the process of rapid freezing and drying in a high vacuum). Examples of lyoprotectants include, without limitation, sucrose, trehalose or mannitol.

A "polyol" refers to an alcohol containing multiple hydroxyl groups, or a sugar alcohol. A sugar alcohol is a hydrogenated form of carbohydrate, whose carbonyl group (aldehyde or ketone, reducing sugar) has been reduced to a primary or secondary hydroxyl group (hence the alcohol). Sugar alcohols have the general formula $H(HCHO)_{n+1}H$, whereas sugars have $H(HCHO)_n HCO$.

An "antioxidant" refers to a molecule capable of slowing or preventing the oxidation of other molecules. Oxidation is a chemical reaction that transfers electrons from a substance to an oxidizing agent. Oxidation reactions can produce free radicals, which start chain reactions that destabilize the protein therapeutics and ultimately affect the product activity. Antioxidants terminate these chain reactions by removing free radical intermediates, and inhibit other oxidation reactions by being oxidized themselves. As a result, antioxidants are often reducing agents, chelating agent and oxygen scavengers such as thiols, ascorbic acid or polyphenols. Non-limiting examples of antioxidants include ascorbic acid (AA, E300), thiosulfate, methionine, tocopherols (E306), propyl gallate (PG, E310), tertiary butylhydroquinone (TBHQ), butylated hydroxyanisole (BHA, E320) and butylated hydroxytoluene (BHT, E321).

A "preservative" is a natural or synthetic chemical that is added to products such as foods, pharmaceuticals, paints, biological samples, wood, etc. to prevent decomposition by microbial growth or by undesirable chemical changes. Preservative additives can be used alone or in conjunction with other methods of preservation. Preservatives may be antimicrobial preservatives, which inhibit the growth of bacteria and fungi, or antioxidants such as oxygen absorbers, which inhibit the oxidation of constituents. Common antimicrobial preservatives include, benzalkonium chloride, benzoic acid, cholorohexidine, glycerin, phenol, potassium sorbate, thimerosal, sulfites (sulfur dioxide, sodium bisulfite, potassium hydrogen sulfite, etc.) and disodium EDTA. Other preservatives include those commonly used in patenteral proteins such as benzyl alcohol, phenol, m-cresol, chlorobutanol or methylparaben.

The term "stable formulation" as used herein in connection with the formulations according to the invention denotes a formulation, which preserves its physical stability/identity/integrity and/or chemical stability/identity/integrity and/or biological activity during manufacturing, storage and application. Various analytical techniques for evaluating protein stability are available in the art and reviewed in Reubsaet et al. (1998) J. Pharm. Biomed. Anal. 17 (6-7): 955-78 and Wang (1999) Int. J. Pharm. 185 (2): 129-88. Stability can be evaluated by storage at selected climate conditions for a selected time period, by applying mechanical stress such as shaking at a selected shaking frequency for a selected time period, by irradiation with a selected light intensity for a selected period of time, or by repetitive freezing and thawing at selected temperatures. The stability may be determined by at least one of the methods selected from the group consisting of visual inspection, SDS-PAGE, IEF, (high pressure) size exclusion chromatography (HPSEC), RFFIT, and kappa/lambda ELISA.

A protein "retains its physical stability" in a pharmaceutical formulation if it shows no signs of aggregation, precipitation and/or denaturation upon visual examination of color and/or clarity, or as measured by UV light scattering or by size exclusion chromatography (SEC) or differential scanning calorimetry (DSC).

A protein "retains its chemical stability" in a pharmaceutical formulation, if the chemical stability at a given time is such that there is no significant modification of the protein by bond formation or cleavage resulting in a new chemical entity. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example. Oxidation is another commonly seen chemical modification.

An antibody "retains its biological activity" in a pharmaceutical formulation, if the biological activity of the antibody at a given time is between about 50% and about 200%, or alternatively between about 60% and about 170%, or alternatively between about 70% and about 150%, or alternatively between about 80% and about 125%, or alternatively between about 90% and about 110%, of the biological activity exhibited at the time the pharmaceutical formulation was prepared as determined, e.g., in an antigen binding assay or virus neutralization assay.

II. Antibodies

Examples of anti-botulinum toxin antibodies can be found in patent publications, e.g., PCT Patent Application Publication No.: WO 2005/05016232 discloses anti-BoNT/A antibodies having synergistic effects in combination, PCT Patent Application Publication No.: WO 2007/094754 discloses anti-BoNT/A1/A2 cross-reactive antibodies, PCT Patent Application Publication No.: WO 2009/008916 discloses anti-BoNT/A, anti-BoNT/B and anti-BoNT/E antibodies, and U.S. Provisional Application No. 61/085,328, filed July 2008, discloses anti-BoNT/B and anti-BoNT/E antibodies. Uses of the anti-botulinum toxin antibodies have also been disclosed. Nowakowski et al. (2002) Proc. Natl. Acad. Sci. Vol. 99 (17): 11346-50 describes potent neutralization of BoNT by a recombinant oligoclonal antibody mixture and discusses potential applicability of oligoclonal antibody mixtures to other diseases e.g. anthrax, smallpox, plague, hemmorhagic fever viruses.

ABT01 is an IgG1 monoclonal antibody against BoNT/A comprising G1m(3) and Km(3) constant regions and VH and VL regions having the amino acid sequences of SEQ ID NOs 3 and 4 (Table 2) respectively. ABT01 contains 1332 amino acid residues and is N-glycosylated with a molecular weight of approximately 149 k Dalton. ABT01 is a neutral antibody with a theoretical pI of 7.0. Several studies were performed to determine the stability profile and the major degradation pathways of the ABT01 antibody.

ABT02 is an IgG1 monoclonal antibody against the BoNT/A, comprising G1m(3) and Km(3) constant regions and VH and VL regions having the amino acid sequences of SEQ ID NOs 1 and 2 (Table 2) respectively. ABT02 contains 1336 amino acid residues and is N-glycosylated with a molecular weight of approximately 149 k Dalton. ABT02 is a basic antibody with a theoretical pI of 7.9. Several studies were performed to determine the stability profile and the major degradation pathways of the ABT02 antibody.

ABT03 is an IgG1 monoclonal antibody against BoNT/A comprising G1m(3) and Km(3) constant regions and VH and VL regions having the amino acid sequences of SEQ ID NOs 5 and 6 respectively. ABT03 contains 1342 amino acid residues and is N-glycosylated with a molecular weight of approximately 149 k Dalton. ABT03 is a basic antibody with a theoretical pI of 8.7. Several studies were performed to determine the stability profile and the major degradation pathways of the ABT03 antibody.

These and other antibodies that have been tested or discussed herein are shown in Table 1 with sequences listed in Table 2. The antibodies shown in Table 1 have either G1m(3) or G1m(1,17) heavy chain constant region allotypes and Km(3) light chain allotypes.

TABLE 1

Antibodies used for coformulations

| Antibody | Antigen | Species | Subclass | pI | Heavy Chain SEQ ID NO: | Light Chain SEQ ID NO: |
|---|---|---|---|---|---|---|
| ABT01 | BoNT/A | Humanized | IgG1 | 7.0 | 3 | 4 |
| ABT02 | BoNT/A | Human | IgG1 | 7.9 | 1 | 2 |
| ABT03 | BoNT/A | Human | IgG1 | 8.7 | 5 | 6 |
| ABT04 | BoNT/A | Human | IgG1 | 7.9 | 1 | 2 |
| ABT05 | BoNT/A | Humanized | IgG1 | 7.0 | 3 | 4 |
| ABT06 | BoNT/A | Human | IgG1 | 8.7 | 5 | 6 |
| ABT07 | BoNT/B | Human | IgG1 | 8.0 | 7 | 9 |
| ABT08 | BoNT/B | Human | IgG1 | 9.1 | 8 | 9 |
| ABT09 | BoNT/B | Human | IgG1 | 8.0 | 10 | 11 |
| ABT10 | BoNT/B | Human | IgG1 | 8.3 | 12 | 13 |
| ABT11 | BoNT/B | Human | IgG1 | 8.2 | 14 | 15 |
| ABT12 | BoNT/B | Human | IgG1 | 8.1 | 16 | 17 |
| ABT13 | BoNT/B | Human | IgG1 | 8.6 | 18 | 19 |
| ABT14 | BoNT/B | Human | IgG1 | 9.3 | 20 | 21 |
| ABT15 | BoNT/B | Human | IgG1 | 8.7 | 22 | 23 |
| ABT16 | BoNT/B | Human | IgG1 | 8.5 | 24 | 25 |
| ABT17/ABT17G | BoNT/B | Human | IgG1 | 8.3 | 36/26 | 27 |
| ABT18 | BoNT/E | Human | IgG1 | 8.1 | 28 | 29 |
| ABT19 | BoNT/E | Human | IgG1 | 8.3 | 30 | 31 |
| ABT20 | BoNT/E | Human | IgG1 | 8.3 | 32 | 33 |
| ABT21 | BoNT/E | Human | IgG1 | 8.5 | 34 | 35 |

TABLE 2

Sequences of the antibodies

```
ABT02/ABT04
Heavy Chain: (SEQ ID NO. 1)
QVQLVQSGGGVVHPGRSLKLSCAGSGFTFSDYDMHWVRQAPGKGLEWVAVMWFDGTEKYSAESVKGRFTISRDNSKNTLFLQM
NSLRADDTAVYYCAREPDWLLWGDRGALDVWGQGTTVTSS Light Chain: (SEQ ID NO. 2)
DIVMTQSPSTLSASVGDRVTITCWASQSISSRLAWYQQKPGKAPKLLMYEATSLGSGVPSRFSGSGSGTEFTLTISSLQPDDF
AAYYCQHYDTYPYTFGQGTKLEIK
```

TABLE 2-continued

Sequences of the antibodies

ABT01/ABT05
Heavy Chain: (SEQ ID NO. 3)
QVQLQQSGGGLVQPGGSLRLSCAASGFTFKYDYMYWIRQAPGKGLEWVATISDGGSYTYYSDSVEGRFTTSRDNSKNTLYLQM
NSLRAEDTAIYYCSRYRYDDAMDYWGQGTLVTVSS Light Chain: (SEQ ID NO. 4)
EIVLTQSPATLSLSPGERATISCRASESVDSYGHSFMQWYQQKPGQAPRLLIYRASNLEPGIPARFSGSGSGTDFTLTISSLE
PEDFAVYYCQQGNEVPFTFGQGTKVEIK ABT03/ABT06
Heavy Chain: (SEQ ID NO. 5)
QVQLQQSGGGLVQPGGSLRLSCAASGFTFSNYAMTWVRQAPGKGLEWVSSISVGGSDTYYADSVKGRFTVSRDNSKNTLLLQM
NSLRAEDTAVYYCAKVRTKYCSSLSCFAGFDSWGQGTRVTVSS Light Chain: (SEQ ID NO. 6)
DVVMTQSPSSLSASVGDRVTITCRASQSISSYLHWYQQKPGKAPTLLISDASSSQSGVPSRFSGSRFGTDFTLTISSLQPEDF
ATYYCQQSYSTRALTFGGGTKVEIK ABT07
Heavy Chain: (SEQ ID NO. 7)
QVQLVQSGAEVKKPGESLVISCKASGDKDTFTSFWIAWVRQMPGKGLEWMGIIYAGDSDTRYSPSFQGHVNISVDRSTNTAYL
QWSSLKASDTAMYYCARHDSRYKYFYFGMDVWGQGTTVTVSS ABT08
Heavy Chain: (SEQ ID NO. 8)
QVQLVQSGAEVKKPGESLKISCKASGDKDTFTSFWIAWVRQMPGKGLEWMGIIYAGDSDTRYSPSFQGHVNISVDRSTNTAYL
QWSSLKASDTAMYYCARHDSRYKYFYFGMDVWGQGTTVTVSS ABT07/ABT08
Light Chain: (SEQ ID NO. 9)
DIQMTQSPSSLSASVGDRVTITCRASQSISSYLNWYQQEPGKAPKLLIYSASSLQSGVPSRFSGSGSGTDFTLTISSLQPEDF
ATYYCQQSYSTPPYTFGQGTKLEIK ABT09
Heavy Chain: (SEQ ID NO. 10)
QVQLLESGGGVVQPGRSLRLSCAASGFTFSSYGMHWVRQAPGKGLEWVAVIWYDGSNKYYADSVKGRFTISRDNSKNTLYLQM
NSLRAEDTAVYYCARGYSNYDYYYGMDVWGQGTTVTVSS Light Chain: (SEQ ID NO. 11)
DIQMTQSPSSLSASVGDRVTITCRASQRISNYLNWYQQKPGKAPKLLIYAASSLQSEVPSRFSGSGYGTDFTLTISSLQPEDF
ATYYCQQSYRPPLTFGGGTKVDIK ABT10
Heavy Chain: (SEQ ID NO. 12)
QVQLVESGGGVVQPGRSLRLSCAASGFTFSHYGMHWVRQSPGKGLEWVAVIWYDGRNPYYAASVKGRFTISRDNDKNTLYLQM
NSLRAEDTAVYYCVKDLTRFHDTTFGVFEMWGPGTTVTVSS Light Chain: (SEQ ID NO. 13)
EIVLTQSPSFVSASVGDRVTITCRASQGISSWLAWYQQKPGKAPKLLIYAASSLQSGVPSRFSGSGSGTEFTLTISSLQPDDF
ATYYCQQYSSLYTFGQGTKVDIK ABT11
Heavy Chain: (SEQ ID NO. 14)
EVQLVQSGGGVVQPGRSLRLSCAASGFIFRTYGMHWVRQAPGKGLEWVAFVSSDGNNKFYSDSVKGRFTISRDNAKNTLYLQM
NSLETEDTAMYYCAKDRYPIDCSGGSCFSYGMDVWGQGTTVTVSS Light Chain: (SEQ ID NO. 15)
EIVLTQSPATLSVSPGERATLSCRASQSVSKFLAWYQQKRGQAPRLLIYGASTRATGIPARFSGSGSGTEFALTISSLQSEDF
ADYYCQQYDNWPITFGQGTRLEIK ABT12
Heavy Chain: (SEQ ID NO. 16)
QVQLVESGGGVVQPGRSLRLSCAASGFTFSSYALHWVRQTPGKGLEWVALISYDGSNKYYADSVKGRFTISRDNSKNMLYLQM
NSLRAEDTAVYYCAKDRSHYGDYVGYLDYWGQGTLVTVSS Light Chain (Lambda): (SEQ ID NO. 17)
SYVLTQPPSVSVAPGKTARITCEGNNVGNKNVHWYQQRPGQAPVLVVHDDSDRPSGIPERFSGSNSGNTATLTINRVEAGDEA
DYYCQVWDSSSAQWVFGGGTKLTVLG ABT13 (non-affinity matured light chain)
Heavy Chain (Same as for ABT12): (SEQ ID NO. 18)
QVQLVESGGGVVQPGRSLRLSCAASGFTFSSYALHWVRQTPGKGLEWVALISYDGSNKYYADSVKGRFTISRDNSKNMLYLQM
NSLRAEDTAVYYCAKDRSHYGDYVGYLDYWGQGTLVTVSS Light Chain (Kappa): (SEQ ID NO. 19)
DIVMTQSPSTLSASVGDRVTITCRASQGISSWLAWYQQKPGKAPKLLIYKASSLESGVPSRFSGSGSGTEFTLTISSLQPEDF
ATYYCLQHNSYPRAFGQGTKLEIK TABLE 2-continued Sequences of the antibodies ABT14
Heavy Chain: (SEQ ID NO. 20)
QVQLVQSGGGLVQPGGSRRLSCAASGFYFNAYWMTWVRQAPGKGLEWVANINLDGTEIYYLDSVKGRFTVSRDNVKNSVFLQM
SSLRVEDTAVYFCARLEWGGRNGWVSPWGQGTLVTVSS Light Chain: (SEQ ID NO. 21)
DIVMTQSPSSLSASVGDRVSISCRASQSISSYLNWYQQKPGKAPKLLIYKTSSLESGVPSRFSGRGSGTDFTLTISSLQPEDF
ATYYCQQSYSTPLTFGGGTKVEIK ABT15
Heavy Chain: (SEQ ID NO. 22)
QVQLVQSGAEVKKPGASVNVSCKASGYTFTGYYIYWVRQAPGQGLEWMGWINPNSGVTKYAQKFQGRVTMTIDTSTNTAYMEL
NRLRADDTAVYYCAREWTQLWSPYDYWGQGTTVTVSS Light Chain: (SEQ ID NO. 23)
DIVLTQSPSTLSASVGDRVTISCRASRSIGWYLNWYQQRPGKAPKLLIYAASSLHNGVPSRFSGSGSGTEFTLTISSLQPDDF
ATYYCQQAFGFPRTFGQGTKVEIK ABT16
Heavy Chain: (SEQ ID NO. 24)
QVQLQESGSRLVKPSQTLSLTCGVSGGSISSSSYSWSWIRQTPGKGLEWIGYIYHSGSTYYNPSLKSRVTMSVDKSRNQFSLN
MSSVTAADTAVYYCARTAFYYENTGPIRCYLDFWGQGTLVTVSS Light Chain: (SEQ ID NO. 25)
DIQMTQSPSTLSASIGDRVTISCRASQSIQSWLAWYQQRPGEAPKLLIYSASTLQTGVPSRFSGSGSGTDFTLTISSLQPEDF
ATYYCQQYNSYPLTFGQGTKLEIK ABT17 (Non-glycosylated at the bold/underlined K residue)
Heavy Chain: (SEQ ID NO. 36)
EVQLLESGGGLVQPGGSLRLSCAASGFTFSNYPMSWVRQAPGKGLAWVSSLTASGDNTFYADSVKGRFTISRDNSKNTLYLQM
HSLRAEDTAVYYCAKALVGRYDISTGYYRPVMDSWGQGTLVTVSS ABT17G (Glycosylated at the bold/underlined N residue)
Heavy Chain: (SEQ ID NO. 26)
EVQLLESGGGLVQPGGSLRLSCAASGFTFSNYPMSWVRQAPGKGLAWVSSLTASGDNTFYADSVKGRFTISRDNSNNTLYLQM
HSLRAEDTAVYYCAKALVGRYDISTGYYRPVMDSWGQGTLVTVSS ABT17/ABT17G
Light Chain: (SEQ ID NO. 27)
DIQMTQSPPSLSASVGDRVTITCRTSQGFTSALAWYQQKPGEPPKLLIYDASKLESGVPSRFSGSGSGTNFALTISSLQPEDF
ATYFCQQSNSYPLTFGGGTKVEIK ABT18
Heavy Chain: (SEQ ID NO. 28)
QVQLQESGAEVKKPGSSVKVSCKASGGDLNKYAITWLRQAPGQGFEWMGGITPIFATTNYAQKFQGRVTITADESTSTVYMDL
SSLGSEDTAIYFCAKSPRGGIVGTFDTWGQGTMVTVSS Light Chain: (SEQ ID NO. 29)
EIVLTQSPSFLSAFVGDRVTITCRTSQSINNYLNWYQQKAGKAPKLLIYAASTLHTGVPSRFSGSGSGTEFTLTISSLQPEDF
ATYYCQQSYSIPLTFGGGTKVEIK ABT19
Heavy Chain: (SEQ ID NO. 30)
QVQLVQSGGGVVQPGKSLRLSCAASGFAFGGYAMHWVRQAPGKGLEWVAVISYDGNKKYYADSVKGRFTISRDNSKNTLYLQM
NSLRAEDAAVFYCARARLCTSTSCYWTFDPWGQGTLVTVSS Light Chain: (SEQ ID NO. 31)
DIQMTQSPSSVSASVGDRVSITCQASQDISNYLNWYQQKPGKAPKLLIYAASSLQSGVPSRFSGSGSGTDFTLTISSLQPEDF
ATYYCQQSYDTPPTFGQGTKLEIK ABT20
Heavy Chain: (SEQ ID NO. 32)
QVQLQESGPGLVKPSETLSLTCSVSGVSISDYYWSWIRQPPGKGLEWIGYIYYSGSTNYNPSLKSRVTISVDTSKNQFSLKLS
SVTAADTAVYYCARHTSGWSGGAFDIWGQGTMVTVSS Light Chain: (SEQ ID NO. 33)
EIVLTQSPNSLAVSLGERATIRCKSSQSVLYSGNNKNYIAWYQQKPGQPPKLLIYWASTRESGVPDRFSGSGSETDFTLTISS
LRAEDVALYYCQQYYSRWTFGQGTKLEIK ABT21
Heavy Chain: (SEQ ID NO. 34)
EVQLVRSGGNLVQPGGSLRLSCAATGPIGSHWMTWVRQAPGQGLEWVANINLDGTEKFYVDSVKGRFTVSRDNRKSSVFLQMN
NLRVDDTAVYYCARLQWGGYNGWLSPWGQGTLVTVSS Light Chain: (SEQ ID NO. 35)
DIVMTQSPSSLSASVGDRVTISCRASQSIRHYVNWYQQKPGKAPKLLIYKASSLASGAPSRFSGSGSGTDFTLTISSLQPDDF
ATYYCQQSYSIPLTFGGGTKVEIK Other suitable antibodies and targets are described in Logtenberg (2007) Trends in Biotechnology 25 (9):390-4, the content of which is incorporated herein by reference in its entirety.

Antibodies can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, which induces the B-lymphocytes to produce IgG immunoglobulins specific for the antigen. This IgG is purified from the mammal's serum. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antiben depot, which allows for a slow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived therefrom, or any other suitable cell line as known in the art (see, those at the following web addresses e.g., atcc.org, lifetech.com., last accessed on Nov. 26, 2007), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al. (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134).

Antibody derivatives of the present invention can also be prepared by delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycolforms of antibodies, including whole antibody molecules, antibody fragments, or fusion proteins that include a region equivalent to the Fc region of an immunoglobulin, having enhanced Fc-mediated cellular toxicity, and glycoproteins so generated.

The antibodies or fragments thereof may be engineered, mutated or modified, e.g., peglyated, glycosylated, hinge-modified (see for example Filpula (2007) Biomol. Eng. 24 (2): 201-15; Dall'Acqua et al. (2006) J. Immunol. 177: 1129-38). Such changes can be also used to alter the PI of the antibody.

Antibody derivatives also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbiol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-

147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59 (6):1236-1243; Jakobovits (1998) Advanced Drug Delivery Reviews 31:33-42; Green and Jakobovits (1998) J. Exp. Med. 188(3):483-495; Jakobovits (1998) Exp. Opin. Invest. Drugs 7 (4):607-614; Tsuda et al. (1997) Genomics 42:413-421; Sherman-Gold (1997) Genetic Engineering News 17 (14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4 (8):761-763; Arbones et al. (1994) Immunity 1 (4):247-260; Jakobovits (1993) Nature 362 (6417):255-258; Jakobovits et al. (1993) Proc. Natl. Acad. Sci. USA 90 (6): 2551-2555; and U.S. Pat. No. 6,075,181.)

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies of this invention can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in antibodies from other mammalian species. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological Interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28 (4-5):489-498. Veneering can also be used to alter the PI of an antibody.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Holliger et al., (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes engineered antibody molecules, fragments and single domains such as scFv, dAbs, nanobodies, minibodies, Unibodies, and Affibodies (Holliger & Hudson (2005) Nature Biotech. 23 (9):1126-36; U.S. Patent Publication US 2006/0211088; PCT Publication WO2007/059782; U.S. Pat. No. 5,831,012).

The term "antibody derivative" further includes "linear antibodies". The procedure for making linear antibodies is known in the art and described in Zapata et al. (1995) Protein Eng. 8 (10):1057-1062. Briefly, these antibodies comprise a pair of tandem Fd segments ($V_H$—$C_H1$—VH—$C_H1$) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58: 671-685.

The term "antibody" also is intended to include antibodies of all isotypes. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307. Alternatively, recombinant DNA techniques may be used.

The isolation of other monoclonal antibodies with the specificity of the monoclonal antibodies described herein can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody of interest.

In some aspects of this invention, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

Antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I), yttrium-90 ($^{90}$Y), bismuth-212 ($^{212}$Bi), bismuth-213 ($^{213}$Bi), technetium-99m ($^{99m}$Tc), rhenium-186 ($^{186}$Re), and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from Chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies also can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

III. Formulations

The stabilization of polypeptides in pharmaceutical compositions remains an area in which trial and error plays a major role. Numerous factors can be varied in order to find suitable excipients and optimal conditions for preparing a long-term stable formulation for a single monoclonal antibody, making this a challenging process. Stably formulating two different antibodies in a single formation is even more problematic which involves choosing excipients and conditions that represent a compromise. These difficulties are compounded for formulating three antibodies, or more.

One aspect of the invention provides a stable pharmaceutical formulation comprising, or alternatively consisting essentially of, or yet alternatively consisting of, a plurality of antibodies directed to at least one serotype of BoNT, an effective amount of a succinate buffer, an effective amount of arginine, wherein the plurality of antibodies are present in substantially equal concentrations, and the pH of the formulation is between about 4.5 and about 7. In some embodiments, the pH of the formulation is between about 4.5, 4.6, 4.7, 4.8, 4.9, or 5.0 and about 6.5, 6.6, 6.7, 6.8, 6.9, or 7.0 and is not detrimental to any of the plurality of antibodies in the formulation. In some embodiments, the pH of the formulation is between about 5 and about 6.5, or alternatively between about 5.5 and about 6.5, or alternatively between about 5.5 and 6, or alternatively between about 6 and 6.5. In some embodiments, the pH of the formulation is at about 5.5, or alternatively about 6, or alternatively about 6.5.

The effective amount or concentration of succinate buffer can be determined with methods known in the art. The effective concentration of a succinate buffer depends on the desired ionic strength and the buffering capacity required. Succinate buffer can be generally used in an amount of about 1 mM to about 200 mM, or alternatively 1 mM to about 100 mM, or alternatively about 1 mM to about 50 mM, or alternatively from about 1 mM to about 40 mM, or alternatively from about 2 to about 40 mM, or alternatively from about 2 mM to about 30 mM, or alternatively from about 3 mM to about 30 mM, or alternatively from about 3 mM to about 25 mM, or alternatively from about 4 mM to about 25 mM, or alternatively from about 4 mM to about 20 mM, or alternatively from about 5 mM to about 20 mM, or alternatively from about 5 mM to about 15 mM. In some embodiments, the succinate buffer is used at about 5 mM, or alternatively about 6 mM, or alternatively about 7 mM, or alternatively about 8 mM, or alternatively about 9 mM, or alternatively about 10 mM, or alternatively about 11 mM, or alternatively about 12 mM, or alternatively about 13 mM, or alternatively about 14 mM, or alternatively about 15 mM. In some embodiments, the succinate buffer is used at about 10 mM. In some embodiments, the succinate buffer comprises sodium succinate or potassium succinate.

The effective amount or concentration of arginine can be determined with methods known in the art. In some embodiments, arginine is present in a concentration of about 5 mM to about 500 mM, or alternatively from about 10 mM to about 450 mM, or alternatively from about 20 mM to about 400 mM, or alternatively from about 50 mM to about 300 mM, or alternatively from about 100 mM to about 200 mM, or alternatively from about 125 mM to about 175 mM. In some embodiments, arginine is present at about 120 mM, or alternatively about 125 mM, or alternatively about 130 mM, or alternatively about 135 mM, or alternatively about 140 mM, or alternatively about 141 mM, or alternatively about 142 mM, or alternatively about 143 mM, or alternatively about 144 mM, or alternatively about 145 mM, or alternatively about 150 mM, or alternatively about 160 mM or alternatively about 175 mM. In some embodiments, arginine is present at about 142 mM.

In some embodiments, the plurality of antibodies are present in the formulation at a concentration from about 0.1 mg/mL to about 200 mg/mL, or alternatively from about 1 to about 150 mg/mL, or alternatively about 2 mg/mL to about 100 mg/mL, or alternatively about 3 mg/mL to about 80 mg/mL, or alternatively about 4 mg/mL to about 50 mg/mL, or alternatively about 5 mg/mL to about 20 mg/mL. In some embodiments, the plurality of antibodies are present at a concentration of at least about 1 mg/mL, or alternatively at least about 2 mg/mL, at least about 3 mg/mL, or alternatively at least about 4 mg/mL, or alternatively at least about 5 mg/mL, or alternatively at least about 6 mg/mL, or alternatively at least about 7 mg/mL, or alternatively at least about 8 mg/mL, or alternatively at least about 9 mg/mL, or alternatively at least about 10 mg/mL, or alternatively at least about 15 mg/mL, or alternatively at least about 20 mg/mL, or alternatively at least about 30 mg/mL, or alternatively at least about 40 mg/mL, or alternatively at least about 50 mg/mL, or alternatively at least about 60 mg/mL, or alternatively at least about 70 mg/mL, or alternatively at least about 80 mg/mL, or alternatively at least about 90 mg/mL, or alternatively at least about 100 mg/mL, or alternatively at least about 120 mg/mL, or alternatively at least about 150 mg/mL or alternatively at least about 200 mg/mL. In some embodiments, at least one of the plurality of antibodies is present at a concentration of at least about 1 mg/mL, or alternatively at least about 2 mg/mL, or alternatively at least about 3 mg/mL, or alternatively at least about 4 mg/mL, or alternatively at least about 5 mg/mL, or alternatively at least about 6 mg/mL, or alternatively at least about 7 mg/mL, or alternatively at least about 8 mg/mL, or alternatively at least about 9 mg/mL, or alternatively at least about 10 mg/mL, or alternatively at least about 15 mg/mL, or alternatively at least about 20 mg/mL, or alternatively at least about 30 mg/mL, or alternatively at least about 40 mg/mL, or alternatively at least about 50 mg/mL, or alternatively at least about 60 mg/mL, or alternatively at least about 70 mg/mL, or alternatively at least about 80 mg/mL, or alternatively at least about 90 mg/mL, or alternatively at least about 100 mg/mL, or alternatively at least about 120 mg/mL, or alternatively at least about 150 mg/mL, or alternatively at least about 200 mg/mL.

The antibodies in the formulation are intended to include a protein or a peptide containing molecule that comprises at least a portion of an immunoglobulin molecule. Examples of such include without limitation, polyclonal antibodies, monoclonal antibodies (mAbs), recombinant antibodies, chimeric antibodies, CDR-grafted antibodies, human antibodies, human monoclonal antibodies, recombinant human antibodies, modified antibodies (e.g., pegylated or glycosylated), single chain antibodies, bispecific antibodies, as well as fragments, including variants and derivatives thereof, provided by known techniques, including, but not limited to enzymatic cleavage, peptide synthesis or recombinant techniques. Antigen binding fragments of an antibody include, for example Fab, Fab', F(ab')$_2$, and F(v) antibody fragments. The antibodies can be isolated from any suitable biological source, e.g., human, ovine, murine, rat, equine and canine. Methods to isolate or prepare antibodies are known in the art or they can be purchased from a commercial vendor.

In yet another aspect of the above embodiments, at least two of the plurality of antibodies specifically recognize and bind the same BoNT serotype. In another aspect, at least two of the plurality of antibodies can specifically recognize and bind different epitopes of the same BoNT serotype. In yet another aspect, at least two of the plurality of antibodies can specifically recognize and bind different BoNT serotype. In some embodiments, the BoNT serotype is BoNT/A, or alternatively BoNT/B, or alternatively BoNT/E, or alternatively combinations thereof.

In one aspect, the antibodies are anti-botulism antibodies, examples of which are described herein.

In some embodiments, the plurality of antibodies comprises ABT01, ABT02, and ABT03. In some embodiments, the plurality of antibodies comprises a first antibody comprising a heavy chain variable region of SEQ ID NO. 3 and a light chain variable region of SEQ ID NO. 4, a second antibody comprising a heavy chain variable region of SEQ ID NO. 1 and a light chain variable region of SEQ ID NO. 2, and a third antibody comprising a heavy chain variable region of SEQ ID NO. 5 and a light chain variable region of SEQ ID NO. 6.

In some embodiments, the plurality of antibodies comprises ABT10, ABT14, and ABT11. In some embodiments, the plurality of antibodies comprises a first antibody comprising a heavy chain variable region of SEQ ID NO. 12 and a light chain variable region of SEQ ID NO. 15, a second antibody comprising a heavy chain variable region of SEQ ID NO. 20 and a light chain variable region of SEQ ID NO. 21, and a third antibody comprising a heavy chain variable region of SEQ ID NO. 14 and a light chain variable region of SEQ ID NO. 15.

In some embodiments, the plurality of antibodies comprises ABT10, ABT14 and ABT17. In some embodiments, the plurality of antibodies comprises a first antibody comprising a heavy chain variable region of SEQ ID NO. 12 and a light chain variable region of SEQ ID NO. 13, a second antibody comprising a heavy chain variable region of SEQ ID NO. 20 and a light chain variable region of SEQ ID NO. 21, and a third antibody comprising a heavy chain variable region of SEQ ID NO. 36 and a light chain variable region of SEQ ID NO. 27.

In some embodiments, the plurality of antibodies comprises ABT10, ABT14 and ABT15. In some embodiments, the plurality of antibodies comprises a first antibody comprising a heavy chain variable region of SEQ ID NO. 12 and a light chain variable region of SEQ ID NO. 13, a second antibody comprising a heavy chain variable region of SEQ ID NO. 20 and a light chain variable region of SEQ ID NO. 21, and a third antibody comprising a heavy chain variable region of SEQ ID NO. 22 and a light chain variable region of SEQ ID NO. 23.

In some embodiments, the plurality of antibodies comprises ABT21, ABT20, and ABT18. In some embodiments, the plurality of antibodies comprises a first antibody comprising a heavy chain variable region of SEQ ID NO. 12 and a light chain variable region of SEQ ID NO. 13, a second antibody comprising a heavy chain variable region of SEQ ID NO. 20 and a light chain variable region of SEQ ID NO. 21, and a third antibody comprising a heavy chain variable region of SEQ ID NO. 14 and a light chain variable region of SEQ ID NO. 15.

In some embodiments, the plurality of antibodies comprises ABT21, ABT20, and ABT19. In some embodiments, the plurality of antibodies comprises a first antibody comprising a heavy chain variable region of SEQ ID NO. 34 and a light chain variable region of SEQ ID NO. 35, a second antibody comprising a heavy chain variable region of SEQ ID NO. 32 and a light chain variable region of SEQ ID NO. 33, and a third antibody comprising a heavy chain variable region of SEQ ID NO. 30 and a light chain variable region of SEQ ID NO. 31.

In some embodiments, the plurality of antibodies comprises ABT21, ABT18, and ABT19. In some embodiments, the plurality of antibodies comprises a first antibody comprising a heavy chain variable region of SEQ ID NO. 34 and a light chain variable region of SEQ ID NO. 35, a second antibody comprising a heavy chain variable region of SEQ ID NO. 28 and a light chain variable region of SEQ ID NO. 29, and a third antibody comprising a heavy chain variable region of SEQ ID NO. 30 and a light chain variable region of SEQ ID NO. 31.

In one aspect, the formulation provides a pharmaceutical formulation comprising two or more antibody mixtures selected from the group of:

a) a first antibody comprising a heavy chain variable region of SEQ ID NO. 3 and a light chain variable region of SEQ ID NO. 4, a second antibody comprising a heavy chain variable region of SEQ ID NO. 1 and a light chain variable region of SEQ ID NO. 2, and a third antibody comprising a heavy chain variable region of SEQ ID NO. 5 and a light chain variable region of SEQ ID NO. 6;

b) a first antibody comprising a heavy chain variable region of SEQ ID NO. 12 and a light chain variable region of SEQ ID NO. 13, a second antibody comprising a heavy chain variable region of SEQ ID NO. 20 and a light chain variable region of SEQ ID NO. 21, and a third antibody comprising a heavy chain variable region of SEQ ID NO. 14 and a light chain variable region of SEQ ID NO. 15;

c) a first antibody comprising a heavy chain variable region of SEQ ID NO. 12 and a light chain variable region of SEQ ID NO. 13, a second antibody comprising a heavy chain variable region of SEQ ID NO. 20 and a light chain variable region of SEQ ID NO. 21, and a third antibody comprising a heavy chain variable region of SEQ ID NO. 36 and a light chain variable region of SEQ ID NO. 27;

d) a first antibody comprising a heavy chain variable region of SEQ ID NO. 12 and a light chain variable region of SEQ ID NO. 13, a second antibody comprising a heavy chain variable region of SEQ ID NO. 20 and a light chain variable region of SEQ ID NO. 21, and a third antibody comprising a heavy chain variable region of SEQ ID NO. 22 and a light chain variable region of SEQ ID NO. 23;

e) a first antibody comprising a heavy chain variable region of SEQ ID NO. 12 and a light chain variable region of SEQ ID NO. 13, a second antibody comprising a heavy chain variable region of SEQ ID NO. 20 and a light chain variable region of SEQ ID NO. 21, and a third antibody comprising a heavy chain variable region of SEQ ID NO. 14 and a light chain variable region of SEQ ID NO. 15;

f) a first antibody comprising a heavy chain variable region of SEQ ID NO. 34 and a light chain variable region of SEQ ID NO. 35, a second antibody comprising a heavy chain variable region of SEQ ID NO. 32 and a light chain variable region of SEQ ID NO. 33, and a third antibody comprising a heavy chain variable region of SEQ ID NO. 30 and a light chain variable region of SEQ ID NO. 31; or g) a first antibody comprising a heavy chain variable region of SEQ ID NO. 34 and a light chain variable region of SEQ ID NO. 35, a second antibody comprising a heavy chain variable region of SEQ ID NO. 28 and a light chain variable region of SEQ ID NO. 29, and a third antibody comprising a heavy chain variable region of SEQ ID NO. 30 and a light chain variable region of SEQ ID NO. 31, 10 mM sodium succinate/succinic acid buffer, 142 mM L-arginine and 0.005% Tween-80, wherein the formulation has a pH of about 6.0.

In some embodiments, the formulation further comprises a tonicity agent that is not arginine. The tonicity agent can be at least one of sodium chloride, potassium chloride, glycerin, an amino acid or sugar. Tonicity agents may be used in an amount of about 5 mM to about 500 mM, or alternatively from about 10 mM to about 450 mM, or alternatively about 20 mM to about 400 mM, or alternatively from about 50 mM to about 300 mM, or alternatively from about 100 mM to about 200 mM, or alternatively from about 125 mM to about 175 mM. In some embodiments, one or more amino acids is present. In some embodiments the amino acid present is glycine, glycine or methionine.

In some embodiments, the formulation further comprises a surfactant. The surfactant can be at least one of polyoxyethylensorbitan fatty acid ester, polyoxyethylene alkyl ether, alkylphenylpolyoxyethylene ether, polysorbate, polyoxyethylene-polyoxypropylene copolymer, or sodium dodecyl sulphate. In a particular aspect, the surfactant is a polysorbate, e.g., Tween 20 or Tween 80. In certain aspects, the surfactant is present in a concentration of from about 0.001 w/v to about 1% w/v, or alternatively of about 0.002 to about 0.1%, or alternatively of about 0.003% to about 0.007%, all percentages presented as "w/v". In some embodiments, the surfactant is used at about 0.003% w/v, or alternatively about 0.004% w/v, or alternatively about 0.0045% w/v, or alternatively about 0.005% w/v, or alternatively about 0.0055% w/v, or alternatively about 0.006% w/v or alternatively about 0.007% w/v. In some embodiments, the surfactant is used at about 0.005% w/v.

In some embodiments, the formulation further comprises a stabilizer. The stabilizer can be at least one of the group a sugar, an amino acid, a polyol, a surfactant, an antioxidant, a preservative, a cyclodextrine, a polyethyleneglycol, albumin or a salt. In a further aspect, the formulation further comprises a cryoprotectant and/or a lyoprotecant.

In some embodiments, the formulation further comprises a pharmaceutically acceptable excipient selected from the group sugar, amino acid, polyol, antioxidant or preservative.

In one aspect of the above embodiments, the plurality of antibodies of the stable pharmaceutical formulation of the invention comprises two antibodies, or alternatively at least three antibodies, or alternatively at least four antibodies, or alternatively at least five antibodies.

In a preferred embodiment, the plurality of antibodies of the stable pharmaceutical formulation of the invention comprises three, four or five antibodies. In another preferred embodiment, the plurality of antibodies of the stable pharmaceutical formulation of the invention comprises six or even up to nine antibodies. In one aspect of the above embodiments, the plurality of antibodies are present in substantially equal concentration in the formulation.

In another aspect of the above embodiments, the plurality of antibodies have isoelectric points from about 6 to about 10, or alternatively from about 6.5 to about 9.5, 7 to 9.5, 7 to 9, or 7.5 to 8.5. In yet another aspect, the maximum of the isoelectric points is at least about 3.5 higher than the minimum of the isoelectric points, or alternatively the maximum of the isoelectric points is at least about 3, or 2.75, 2.5, 2.25, 2.1, 2.0, 1.9, 1.8, 1.7, 1.6, or 1.5 higher than the minimum of the isoelectric points.

The formulations of the current invention can be stable at about room temperature for at least 30 days, or alternatively stable at a temperature from about 2.0° C. to about 8.0° C. for at least about a year, or alternatively stable for at least about two years or alternatively at least three years, or alternatively at least four years, or at least five years at a temperature from about 2.0° C. to about 8.0° C., or alternatively stable for at least about two years at a temperature of about 5° C. In some embodiments, the formulations of the current invention are stable at about 25° C. for up to a year, or alternatively for up to two years. In some embodiments, the formulations of the current invention are stable at about 40° C. for up to three months, or alternatively for up to six months. In some embodiments, the formulations are stable at about −20° C. for up to one year, of alternatively two years, three years, four years, or five years. In some embodiments, the formulations are stable at about −80° C. for up to one year, of alternatively two years, three years, four years, or five years.

In some embodiments, the formulation of the current invention is physically stable. In some embodiments, the formulation of the current invention is chemically stable. In some embodiments, the formulation of the current invention is biologically stable. In some embodiments, the formulation of the current invention is physically stable, chemically stable and biologically stable.

IV. Determination of Formulation Stability

The accumulation of low molecular weight (LMW) species and high molecular weight (HMW) species are useful measures of antibody stability. Accumulation of either LMW or HMW in a formulation is indicative of instability of a protein stored as part of the formulation. Size exclusion chromatography with HPLC can be used to determine the presence of LMW and HMW species. Suitable systems for such measurements are known in the art, e.g., HPLC systems (Waters, Milford, Mass.). Other systems known in the art can be used to evaluate the integrity of antibody in a formulation, for example, SDS-PAGE (to monitor HMW and LMW species), bioassays of antibody activity, enzyme-linked immunosorbent assay, ability to bind purified antigen, and cation exchange-HPLC (CEX-HPLC; to detect variants and monitor surface charge). In one example, a bioassay is an in vitro toxin neutralization assay such as a mouse hemidiaphragm assay as described in Nowakowski et al. (2002) Proc. Natl. Acad. Sci. 99 (17): 11346-50. In another example, a bioassay is an in vivo toxin neutralization assay such as a mouse survival assay. Alternatively a bioassay may be a cell-based assay in which the effect of the antibody on cell signaling is measured. A number of assays for measuring the level of signaling are available in the art. See, for example: Dove (2006) Nat. Methods 3: 223-229.

The development of a stable co-formulation required new methods to measure the stability and degradation of the individual antibodies when present in the antibody mixture. A number of methods were developed for this purpose. The methods, customized from and based on IEX-HPLC, SEC-HPLC and ELISA, are described in more detail in Example 3.

V. Storage and Preparation of Formulations

Another aspect of the invention provides a method for preparing the stable pharmaceutical formulation of the invention, comprising, or alternatively consisting essentially of, or alternatively consisting, admixing a plurality of antibodies and an effective amount of a succinate buffer and an effective amount of arginine to a pH between about 4.5 and about 7. In some embodiments, the pH of the formulation is between about 4.5, 4.6, 4.7, 4.8, 4.9, or 5.0 and about 6.5, 6.6, 6.7, 6.8, 6.9, or 7.0 and is not detrimental to any of the plurality of antibodies in the formulation. In some embodiments, the pH of the formulation is between about 5 and about 6.5, or alternatively between about 5.5 and about 6.5, or alternatively between about 5.5 and 6, or alternatively between about 6 and 6.5. In some embodiments, the pH of the formulation is at about 5.5, or alternatively about 6, or alternatively about 6.5.

In some embodiments, the method comprises admixing to the formulation a tonicity agent that is not arginine. The tonicity agent can be at least one of sodium chloride, potassium chloride, glycerin, an amino acid or sugar. Tonicity agents may be used in an amount of about 5 mM to about 500 mM, or alternatively from about 10 mM to about 450 mM, or alternatively about 20 mM to about 400 mM, or alternatively from about 50 mM to about 300 mM, or alternatively from about 100 mM to about 200 mM, or alternatively from about 125 mM to about 175 mM. In some embodiments, one or more amino acids is present. In some embodiments the amino acid present is glycine, glycine or methionine.

In some embodiments, the method further comprises, or alternatively consists essentially of, or yet further consists of, adding a tonicity agent to the formulation. The tonicity agent can be at least one or more of sodium chloride, potassium chloride, glycerin, an amino acid or sugar. Tonicity agents may be added to reach a concentration of about 5 mM to about 500 mM, or alternatively from about 10 mM to about 450 mM, or alternatively from about 20 mM to about 400 mM, or alternatively from about 50 mM to about 300 mM, or alternatively from about 100 mM to about 200 mM, or alternatively from about 125 mM to about 175 mM. In some embodiments, one or more amino acids is present. In some embodiments the amino acid added is one or more of arginine, methionine, glycine or alanine. In some embodiments, the amino acid is added to reach a concentration of about 5 mM to about 500 mM, or alternatively from about 10 mM to about 450 mM, or alternatively from about 20 mM to about 400 mM, or alternatively from about 50 mM to about 300 mM, or alternatively from about 100 mM to about 200 mM, or alternatively from about 125 mM to about 175 mM. In some embodiments, the amino acid is added to reach a concentration of around 120 mM, or alternatively about 125 mM, or alternatively about 130 mM, or alternatively about 135 mM, or alternatively about 140 mM, or alternatively about 141 mM, or alternatively about 142 mM, or alternatively about 143 mM, or alternatively about 144 mM, or alternatively about 145 mM, or alternatively about 150 mM, or alternatively about 160 mM or alternatively about 175 mM. In some embodiments, arginine is added to reach a concentration of about 142 mM.

In some embodiments, the method further comprises adding a surfactant to the formulation. The surfactant can be at least one of the group polyoxyethylensorbitan fatty acid ester, polyoxyethylene alkyl ether, alkylphenylpolyoxyethylene ether, polyoxyethylene-polyoxypropylene copolymer, polysorbate, or sodium dodecyl sulphate. In a particular aspect, the surfactant is a polysorbate such as Tween 20 or Tween 80. In certain aspects, the surfactant is added to reach a concentration of from about 0.001% w/v to about 1% w/v, or alternatively of from about 0.002% w/v to about 0.1% w/v, or alternatively of from about 0.003% w/v to about 0.007% w/v. In some embodiments, the surfactant is used to reach a concentration of about 0.003% w/v, or alternatively 0.004% w/v, or alternatively 0.0045% w/v, or alternatively 0.005% w/v, or alternatively 0.0055% w/v, or alternatively 0.006% w/v, or alternatively 0.007% w/v. In some embodiments, the surfactant is added to reach a concentration of about 0.005% w/v.

In some embodiments, the method further comprises adding a stabilizer to the formulation. The stabilizer can be at least one of the group a sugar, an amino acid, a polyol, a surfactant, an antioxidant, a preservative, a cyclodextrine, a polyethyleneglycol, albumin or a salt. In some embodiments, the stabilizer is present in the formulation at a concentration of from about 0.001% to about 5%, or alternatively from about 0.01% to about 2%, or 0.1% to 1%, or 0.2% to 0.8% or alternatively at about 0.5%. In some embodiments, the stabilizer is present in the formulation at a concentration of from about 90 mM to about 300 mM, or alternatively from 100 mM to about 200 mM, or alternatively at about 150 mM.

In one aspect of the method, the plurality of antibodies admixed to the formulation comprises two antibodies, or alternatively at least three antibodies, or alternatively at least four antibodies, or alternatively at least five antibodies directed to at least one serotype of BoNT. In a preferred embodiment, the plurality of antibodies admixed to the formulation comprises three, four or five or more antibodies. In another preferred embodiment, the plurality of antibodies of the stable pharmaceutical formulation of the invention comprises six or even up to nine or ten antibodies.

In some embodiments of the method, the plurality of antibodies are admixed to reach a concentration of from about 0.1 mg/mL to about 200 mg/mL, or alternatively from about 1 to about 150 mg/mL, or alternatively about 2 mg/mL to about 100 mg/mL, or alternatively about 3 mg/mL to about 80 mg/mL, or alternatively about 4 mg/mL to about 50 mg/mL, or alternatively about 5 mg/mL to about 20 mg/mL. In some embodiments, the plurality of antibodies are present at a concentration of at least about 1 mg/mL, or alternatively at least about 2 mg/mL, at least about 3 mg/mL, or alternatively at least about 4 mg/mL, or alternatively at least about 5 mg/mL, or alternatively at least about 6 mg/mL, or alternatively at least about 7 mg/mL, or alternatively at least about 8 mg/mL, or alternatively at least about 9 mg/mL, or alternatively at least about 10 mg/mL, or alternatively at least about 15 mg/mL, or alternatively at least about 20 mg/mL, or alternatively at least about 30 mg/mL, or alternatively at least about 40 mg/mL, or alternatively at least about 50 mg/mL, or alternatively at least about 60 mg/mL, or alternatively at least about 70 mg/mL, or alternatively at least about 80 mg/mL, or alternatively at least about 90 mg/mL, or alternatively at least about 100 mg/mL, or alternatively at least about 120 mg/mL, or alternatively at least about 150 mg/mL or alternatively at least about 200 mg/mL. In some embodiments, at least one of the plurality of antibodies is present at a concentration of at least about 1 mg/mL, or alternatively at least about 2 mg/mL, or alternatively at least about 3 mg/mL, or alternatively at least about 4 mg/mL, or alternatively at least about 5 mg/mL, or alternatively at least about 6 mg/mL, or alternatively at least about 7 mg/mL, or alternatively at least about 8 mg/mL, or alternatively at least about 9 mg/mL, or alternatively at least about 10 mg/mL, or alternatively at least about 15 mg/mL, or alternatively at least about 20 mg/mL, or alternatively at least about 30 mg/mL, or alternatively at least about 40 mg/mL, or alternatively at least about 50 mg/mL, or alternatively at least about 60 mg/mL, or alternatively at least about 70 mg/mL, or alternatively at least about 80 mg/mL, or alternatively at least about 90 mg/mL, or alternatively at least about 100 mg/mL, or alternatively at least about 120 mg/mL, or alternatively at least about 150 mg/mL, or alternatively at least about 200 mg/mL.

In yet another aspect of the method, at least two of the plurality of antibodies specifically recognize and bind the same BoNT serotype. In another aspect, at least two of the plurality of antibodies can specifically recognize and bind different epitopes of the same BoNT serotype. In yet another aspect, at least two of the plurality of antibodies can specifically recognize and bind different BoNT serotype. In some embodiments, the BoNT serotype is BoNT/A, or alternatively BoNT/B, or alternatively BoNT/E, or alternatively combinations thereof.

Examples of antibodies that can be used in the formulation of the method are shown in Table 1.

Formulations containing antibodies can be frozen for storage. Accordingly, it is desirable that the formulation be relatively stable under such conditions, including, under freeze-thaw cycles. One method of determining the suitability of a formulation is to subject a sample formulation to at least two, e.g., three, four, five, eight, ten, or more cycles of freezing (at, for example −20° C. or −80° C.) and thawing (for example by fast thaw in a 37° C. water bath or slow thaw at 2°-8° C.), determining the amount of low molecular weight (LMW) species and/or high molecular weight (HMW) species that accumulate after the freeze-thaw cycles and comparing it to the amount of LMW species or HMW species present in the sample prior to the freeze-thaw procedure. An increase in the LMW or HMW species indicates decreased stability.

Formulations can be stored after lyophilization. Therefore, testing a formulation for the stability of the protein component of the formulation after lyophilization is useful for determining the suitability of a formulation. The method is similar to that described, supra, for freezing, except that the sample formulation is lyophilized instead of frozen, reconstituted to its original volume or desired concentration, and tested for the presence of LMW species and/or HMW species.

The lyophilized sample formulation is compared to a corresponding sample formulation that was not lyophilized. An increase in LMW or HMW species in the lyophilized sample compared to the corresponding sample indicates decreased stability in the lyophilized sample.

In general, a lyophilization protocol includes loading a sample into a lyophilizer, a pre-cooling period, freezing, vacuum initiation, ramping to the primary drying temperature, primary drying, ramping to the secondary drying temperature, secondary drying, and stoppering the sample.

Additional parameters that can be selected for a lyophilization protocol include vacuum (e.g., in microns) and condenser temperature. Suitable ramp rates for temperature are between about 0.1° C./min. to about 2° C./min., for example about 0.1° C./min. to about 1.0° C./min., about 0.1° C./min. to about 0.5° C./min., about 0.2° C./min. to about 0.5° C./min., about 0.1° C./min., about 0.2° C./min., about 0.3° C./min., about 0.4° C./min., about 0.5° C./min., about 0.6° C./min., about 0.7° C./min., about 0.8° C./min., about 0.9° C./min., and about 1.0° C./min. Suitable shelf temperatures during freezing for a lyophilization cycle are generally from about −55° C. to about −5° C., about −25° C. to about −5° C., about −20° C. to about −5° C., about −15° C. to about −5° C., about −10° C. to about −5° C., about −10° C., about −11° C., about −12° C., about −13° C., about −14° C., about −15° C., about −16° C., about −17° C., about −18° C., about −19° C., about −20° C., about −21° C., about −22° C., about −23° C., about −24° C. or about −25° C. Shelf temperatures can be different for primary drying and secondary drying, for example, primary drying can be performed at a lower temperature than secondary drying. In a non-limiting example, primary drying can be executed at about 0° C. and secondary drying at about 25° C.

A formulation can also be spray-dried and then stored. Spray-drying is conducted using methods known in the art, and can be modified to use liquid or frozen spray-drying (e.g., using methods such as those from Niro Inc. (Madison, Wis.), Upperton Particle Technologies (Nottingham, England), or Buchi (Brinkman Instruments Inc., Westbury, N.Y.), or U.S. Patent Publication Nos. WO 2003/0072718 and WO 2003/0082276).

VI. Therapies

The present invention, in another aspect, provides a method for treating a subject in need of therapy, comprising administering to the subject an effective amount of one or more of the formulation of the invention. The therapeutically effective amount of a formulation will depend on the disease or condition of the subject and actual clinical setting.

In some embodiments, the subject is infected or exposed to at least on serotype of botulinum neurotoxin. In one aspect of the embodiments, the serotype is at least one of BoNT/A, BoNT/B or BoNT/E.

In some embodiments the subject is suffering from intoxication. In some embodiments the intoxication may be caused by infection. In some embodiments the intoxication may be caused by ingestion of toxin. In some embodiments the intoxication may be caused by contact with a venomous animal. In some embodiments the intoxication may be caused by an act or bioterrorism or biological warfare.

The invention, in yet another aspect, provides a method for preventing botulinum neurotoxin infection of a subject, comprising administering to the subject an effective amount of the formulation of the invention. The therapeutically effective amount of a formulation will depend on the disease or condition of the subject and actual clinical setting.

In some embodiments, the subject is in need of prophylactically or therapeutically neutralizing a botulinum neurotoxin. In one aspect of the embodiments, the botulinum neurotoxin is at least one of botulinum neurotoxin A, B or E.

Also provided is use of the formulation of the invention in the preparation of a medicament. Further provided is use of the formulation of the invention in the preparation of a medicament to treat a subject.

Administration of the formulation of the invention can be made by methods known in the art. In one aspect, the route of administration is intramuscular injection. In another aspect, the route of administration is intravenous injection. In another aspect, the route of administration is subcutaneous injection.

The effective amount of the formulation of the invention can be experimentally determined and can vary depending upon the specific antibody, the disease or symptom to be treated or alleviated, the age, gender and weight of the subject to be treated, the dosing regimen of the formulation, the severity of the disease condition, the manner of administration and the like, all of which can be determined readily by one of skill in the art. In one aspect, the effective amount of the formulation of the invention is between about 0.1 mL to about 2 mL, or alternatively from about 0.1 mL to about 1.5 mL, or alternatively from about 0.2 mL to about 1.2 mL, or alternatively from about 0.2 mL to about 1.0 mL, or alternatively from about 0.25 mL to about 1.0 mL, or alternatively from about 0.25 mL to about 0.9 mL, or alternatively from about 0.3 mL to about 0.9 mL, or alternatively from about 0.3 mL to about 0.8 mL, or alternatively from about 0.4 mL to about 0.8 mL, or alternatively from about 0.4 mL to about 0.7 mL, or alternatively from about 0.4 mL to about 0.6 mL, or alternatively from about 0.45 mL to about 0.55 mL. In another aspect, the effective amount of the formulation of the invention is about 0.1 mL, or alternatively about 0.2, or alternatively about 0.3, or alternatively about 0.4, or alternatively about 0.45, or alternatively about 0.5, or alternatively about 0.55, or alternatively about 0.6, or alternatively about 0.7, or alternatively about 0.8, or alternatively about 0.9, or alternatively about 1.0, or alternatively about 1.2, or alternatively about 1.5, or alternatively about 1.8, or alternatively about 2 mL.

Administration of the formulation of the invention can be composed of one dose, or a number of consecutive doses. The amount and frequency of dosage can be determined with methods known in the art, and will vary depending on factors such as the risk of continued risk of infection, half life of the antibody and toxicity of the formulation.

Administration of the formulation of the invention can be made at one site of the subject, or multiple sites of the subject. The amount of dosage and sites can be determined with methods known in the art. In one aspect, the administration is one or more intramuscular injection at the thigh or the arm of the subject. In another aspect, the administration is one or more intramuscular injection at the rear thigh of the subject.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Example 1

Materials and Methods for Development of Formulations for Individual Antibodies

Transient Production of Antibodies

Antibodies can be transiently expressed in HEK 293 cells and purified by Protein A and Q-Sepharose. Lipofectamine or polyethylenimine (PEI) was used for transient transfection of 293 cells to produce 200 mg of each candidate antibody. Although PEI is a polymer and lipofectamine is lipid based, the process of transfection was very similar for both and did not affect the quality of the MAb protein expressed. Lipofectamine was more efficient for transfection, allowing use of smaller volumes of cells. Lipofectamine transfections were expanded in shake flasks and the PEI was expanded in Wave bioreactors, however, the medium and cell growth conditions were the same for both. Both lipofectamine and PEI were positively charged molecules and should be removed by the protein A step because they should not bind the resin. Further purification with HIC can be used to remove high aggregate. Final pools were then diafiltered or dialyzed into the target formulation.

Permanent Production of Antibodies

Antibodies can be permanently produced in CHO cell lines. Harvested antibody material can be purified with column chromatography. The clarified cell culture fluid was first captured with a Protein A affinity column. The eluted antibody solution was then held at the low pH for viral inactivation. The antibody was further purified with an anion exchange column (Q-Sepharose) and an HIC column (Butyl Sepharose). The antibody material used in formulation development was either Protein A captured eluent, pH adjusted to approximately 6, or further-purified material (Q-Sepharose, HIC).

Preparation of Antibody Formulation

A formulation of 10 mM NaSuccinate, 142 mM L-arginine, 0.005% Tween-80 at pH 6.0 was made with the following procedure. First, 1% Tween-80 stock solution was prepared by adding 1 gram by weight of Tween-80 (JT Baker PN 4117-04) to 50 mL Milli-Q water, QS (quantity sufficient) to 100 mL Milli-Q and mixing well. Then, to prepare the buffer, add 500 mL Milli-Q to vessel, then 2.52 g Disodium succinate-6($H_2O$) (Sigma Aldrich PN 14170), 0.077 g Succinic Acid (Sigma Aldrich PN 14079), 30.0 g L-arginine monohydrochloride (JT Baker PN 2067-07) and 5 mL of the 1% Tween-80 stock solution and adjust the total volume to 900 mL. The pH of the buffer should be 6.0, if not it can be adjusted with NaOH or HCl. To make the final buffer, QS the solution to 1000 mL and mix well.

Example 2

Stability Assessment for Formulations of Individual Antibodies

Visual Assessment

Visual assessment was made against a black/white background under a top-mounted fluorescent light.

Protein Concentration

Protein concentration was determined by ultraviolet absorbance at 280 nm.

Turbidity

The absorbance at 350 nm due to light scattering was measured for neat samples against filtered water on a Shimadzu UV-160U UV-Vis Spectrophotometer.

Size Exclusion High Performance Liquid Chromatography (SEC-HPLC)

The size-exclusion HPLC method utilized the TSKG 3000 SWXL SEC column manufactured by Toso Hass. A 30 minute isocratic method was used with detection at 214 nm. Two mobile phases were used for early vs. late studies. One mobile phase was 50 mM $NaPO_4$, 0.2 M NaCl, pH 7.0. The other phase was 50 mM $NaPO_4$, 0.1 M $(NH_4)_2SO_4$, with 5% Acetonitrile, pH 6.8. The flow rate was 0.5 ml/min with a 10 µl injection at 1 mg/ml (10 µg). The percent aggregate and percent clip were reported from the total area percent of each protein related absorbance. Samples were run on an Agilent 1100 Series HPLC and chromatograms integrated using Chemstation software; alternately samples were run on a Beckman-Coulter system Gold HPLC and integrated using Beckman's 32 Karat software.

Weak Cation Exchange Chromatography (IEX)

The IEX-HPLC method utilized a Dionex ProPac IEX-10, 4×250 mm column. Samples were run on Agilent 1100 & 1200 Series HPLC's and chromatograms integrated using Chemstation software. Mobile Phase A: 10 mM $NaPO_4$ monobasic, monohydrate; Mobile Phase B: 10 mM $NaPO_4$ dibasic, heptahydrate, 1% NaCl. A gradient method was developed for each of the individual BoNT antibodies as well as a step gradient method that resolved the main peaks of each mAb in mixtures. Detection was at 229 nm with varying injection amounts. The percents acidic, basic and main peak were reported from the total area percent of each protein related absorbance.

Differential Scanning Calorimetry (DSC)

Samples were filtered and degassed prior to thermal analysis. DSC analysis used a MicroCal VP-DSC™ calorimeter and scans integrated using Origin® software. All thermal scans were performed from 15-90° C. or 15-100° C. at 90° C./hour with reference to a target formulation buffer.

Solubility Studies

Antibody material from two different batches was used for each solubility study. Antibody material was dialyzed against buffers at different pH levels. The dialyzed solutions were filtered through a 0.22 μm filter. An aliquot of the filtered solution was diluted appropriately with the corresponding buffer for the UV measurement. The concentration was calculated by dividing the A280 with the antibody's theoretical absorbance.

Thermal Denaturation Measurement

Differential Scanning calorimetry (DSC) analyses were performed with the VP-DSC™ (MicroCal, Northampton, Mass.). Samples were prepared either by dialysis or centrifugal buffer exchange units, filtered and degassed prior to thermal analysis. Approximately 0.5 ml of each sample was loaded into the sample cell with the same amount of matching buffer into the reference cell. The samples were scanned from 15 to 90° C. (20 to 90° C. for ABT03 samples) at a rate of 90° C./hour. The data were analyzed with the Origin® 5.0 data analysis software.

Freeze-Thaw and Shaking Studies

Sample solutions were filled into 1.7 ml plastic centrifugation tubes at 1 mL aliquots. The samples were frozen in a −70° C. freezer for at least 2 hours and thawed at ambient temperature until all ice disappeared (approximately 1 hour). Samples at freeze-thaw cycles 0 (control), 1, 3, and 5 were collected and kept at 2-8° C., or the temperature under which an analysis was performed, until being analyzed together by SEC-HPLC and UV spectroscopy. The shaking studies were carried out by placing the sample containers in the Eppendorf Thermomixer R and shaking continuously at 1000 RPM for up to 72 hours.

Accelerated and Real Time Stability Studies

Antibody was dialyzed into the desired formulation buffer at 2-8° C. with three buffer exchanges as indicated below. The concentrations of the dialyzed solutions were measured by ultraviolet absorbance at 280 nm and then adjusted to a desired concentration, which can range from about 0.1 mg/ml to about 5 mg/ml and was typically 1 mg/ml with the corresponding buffer. The formulated samples solutions were filtered with a 0.22 μm filter before being filled into a 2 cc polypropylene micro centrifugation tube. Stability samples were stored in incubators at the accelerated storage temperature of 40° C. and/or 50° C., 25° C., as well as 2-8° C. The stability samples were taken out of the incubator at appropriate time points for stability assays. The samples were first examined visually for any signs of precipitation, discoloration and clarity. After initial visual observation, the samples were brought to room temperature prior to analysis. If testing took longer than one day, samples were stored at 2-8° C. cooler for the duration of the testing. Samples were centrifuged at 10,000 relative centrifugal force (rcf) for 5 minutes to remove any particulates and large insoluble aggregates, and adequate amount of supernatant was placed into an HPLC sample vial for analysis or used for UV measurement. In addition to centrifugation, samples were optionally 0.22 μm filtered with "Spin-X", a cellulose acetate type of filter.

Table 3 shows the amounts and purities of the transiently-expressed BoNT/B and BoNT/E monoclonal antibodies produced.

TABLE 3

| Transiently produced BoNT/B and BoNT/E MAbs | | | | |
|---|---|---|---|---|
| | Purified antibody | Purity by SEC-HPLC | | |
| Antibody* | amount, mg | Monomer | Aggregate | Clip |
| ABT07 | 6.78 | 98.5 | 1.5 | 0 |
| ABT08 | 2.7 | 98.8 | 1.2 | 0 |
| ABT08 | 392.6 | 97.57 | 2.28 | 0.02 |
| ABT08 | 93.33 | 98.21 | 1.79 | 0.00 |
| ABT09 | 186.6 | 97.7 | 2.3 | 0 |
| ABT10 | 125.58 | 95.3 | 1.5 | 3.2 |
| ABT10 | 1221 | 98.4 | 1.6 | 0.1 |
| ABT11 | 257.5 | 94 | 5.6 | 0.4 |
| ABT12 | 3.56 | 86.9 | 11.8 | 1.2 |
| ABT12 | 2.7 | 88.8 | 9.9 | 1.3 |
| ABT12 | 6.63 | 84.8 | 14.3 | 0.9 |
| ABT12 | 3.08 | 82 | 17 | 0.9 |
| ABT12 | 318.5 | 82.6/93.2 | 17.3/6.8 | 0.1/0.0 |
| ABT12 | 1.95 | 90.4 | 9.3 | 0.3 |
| ABT12 | 145.93 | 95.27 | 4.73 | 0 |
| ABT14 | 98.4 | 81.99 | 0.12 | 17.89 |
| ABT14 | 111.1 | 98.5 | 0.6 | 0.9 |
| ABT18 | 95 | 97.7 | 2.3 | 0 |
| ABT19 | 14.75 | 99.2 | 0.8 | 0 |
| ABT21 | 335.4 | 100 | 0 | 0 |

*Each individual lot of antibody production is shown.

Example 3

Formulation of Individual Antibodies

ABT01

ABT01 showed limited solubility of approximately 3.3 mg/ml in sodium phosphate buffer (10 mM $NaH_2PO4/Na_2HPO_4$, 140 mM NaCl) at pH 5.5, 6.5, and 7.5 ABT01 showed similar thermal transition temperatures upon unfolding ($T_0$ and Tm) at the 3 different pH values. The limited solubility of ABT01 in PBS based buffers made it necessary to screen other more effective solubilizers so that the ABT01 concentration can be increased to allow more options for eventual co-formulation. To this end, five different excipients were chosen for the study of their effects on the solubility and thermal transition temperatures on ABT01. The starting ABT01 solution was dialyzed against each of the five excipients listed in Table 4 which also lists the resulting solubility and DSC data. The 5% L-arginine formulation was the only buffer that resulted in clear antibody solution during the entire dialysis. The other four buffers resulted in cloudiness and precipitation for the antibody solution in the dialysis cassette.

TABLE 4

| Solubility and thermal transition temperatures of ABT01 in 10 mM L-histidine, pH 6.5 with five different excipients | | | | |
|---|---|---|---|---|
| Formulation | Visual appearance | Solubility, mg/ml | Tm, ° C. | Tp, ° C. |
| 0.9% NaCl | Precipitation | 4.12 | 66.9 | 72.9 |
| 2% Glycine | Cloudy/precipitation | 2.79 | 66.1 | 75.3 |
| 5% L-arginine HCl | Clear | >5.17 | 66.9 | 81.6 |
| 5% sorbitol | Cloudy/precipitation | 2.28 | 65.6 | 77.1 |
| 4% sucrose, 1% Glycine | Cloudy/precipitation | 1.22 | 65.8 | 83.4 |

Another study was carried out to assess the effect of L-arginine concentration on the solubility of ABT01. ABT01 material was dialyzed against 2, 4, and 8% L-arginine monohydrochloride in 10 mM sodium citrate at pH 6.5. The dialyzed antibody solution was then concentrated by centrifugation with a Vivascience concentrator (MWCO 10 k). The concentrated antibody solution was diluted with the corresponding buffer and the concentration was measured with UV A280 in duplicates or triplicates. The thermal transition temperatures were measured with DSC after diluting the sample concentration to 1 mg/ml antibody. The solubility and DSC data are presented in Table 5.

TABLE 5

| Solubility and thermal transition temperatures of ABT01 in sodium citrate, pH 6.5 buffers with three different L-arginine concentrations. | | | | |
|---|---|---|---|---|
| L-arginine, % | Concentration rate | Solubility (mg/ml) | Tm, ° C. | Tp, ° C. |
| 2.0 (~95 mM) | Moderate | 24 | 67.1 | 71.8 |
| 4.0 (~189 mM) | Moderate | 43 | 67.1 | 73.1 |
| 8.0 (~379 mM) | Fast | 76 | 66.6 | 83.5 |

The concentration values of ABT01 in the 3 different L-arginine concentration buffers had probably not reached the solubility limit. The centrifugation was stopped due to the diminishing volume of the retentate. The solubility data shown in Table 5 indicated that ABT01 could reach at least 40 mg/ml concentration in 4.0% L-arginine buffer.

ABT01 showed almost identical Tm (67.1° C.) in the 2% and 4% L-arginine formulations and a slightly lower Tm (66.6° C.) in 8% L-arginine solution, suggesting that too high an L-arginine concentration was probably unfavorable to the stability of ABT01. Unfolded ABT01 maintained in the solution in 8% L-arginine and aggregation/precipitation occurred at much higher temperature than in lower L-arginine concentrations, as suggested by the much higher Tp value (83.5° C.) in the 8% L-arginine solution.

Physical Stability

ABT01 (formulated in 10 mM sodium phosphate, 140 mM NaCl at pH 6.5) was subjected to 5 cycles of freeze-and-thaw or shaking at 1000 RPM for 2 hours. The effect of repeated freeze-thaw had a pronounced effect on ABT01. Without the presence of polysorbate 80 (Tween 80), the sample lost approximately 30% of the original amount of protein after 5 cycles of freeze-thaw. The presence of 0.005% (w/v) polysorbate 80 was able to reduce the protein loss to approximately 25%, a marked improvement. Higher concentrations of polysorbate 80 did not improve the protection any further. It appeared that the effective polysorbate 80 concentration was about 0.005%. ABT01 was stable against shaking regardless of the presence of surfactant.

Effect of pH

ABT01 samples were subjected to accelerated stability studies with HPLC analyses. SEC-HPLC chromatograms for the stability samples formulated in the three different pH phosphate buffers stored at 40° C. for 6 months indicated that higher pH formulation caused substantially more aggregates than the lower pH formulation. The formation of cleaved species seemed to be not as dramatically affected by pH. Nevertheless, the pH 6.5 formulation had the least amount of clips than either the higher or the lower pH formulations.

This effect of pH on the formation of soluble aggregates and clips was consistently observed in the earlier time point stability samples, as shown in FIG. 1. The pH 6.5 formulation consistently gave the highest percent monomer as measured by SEC-HPLC (FIG. 1A). The pH 7.5 formulation consistently gave the highest aggregates as well as clips. Although the pH 5.5 formulation controlled the soluble aggregate formation well, it consistently produced more clips than the pH 6.5 formulation.

It appeared that the pH 6.5 formulation contained the least amount of the acidic species. After being stored at 40° C. for 6 months, the antibody species in the pH 7.5 formulation were substantially more acidic than those in the two lower pH formulations. For the purpose of controlling the increase of acidic species (deamidation), it is desirable to avoid the higher pH formulation and chose a pH in the 5.5 to 6.5 range.

Effect of Buffer Species

Figure 2:
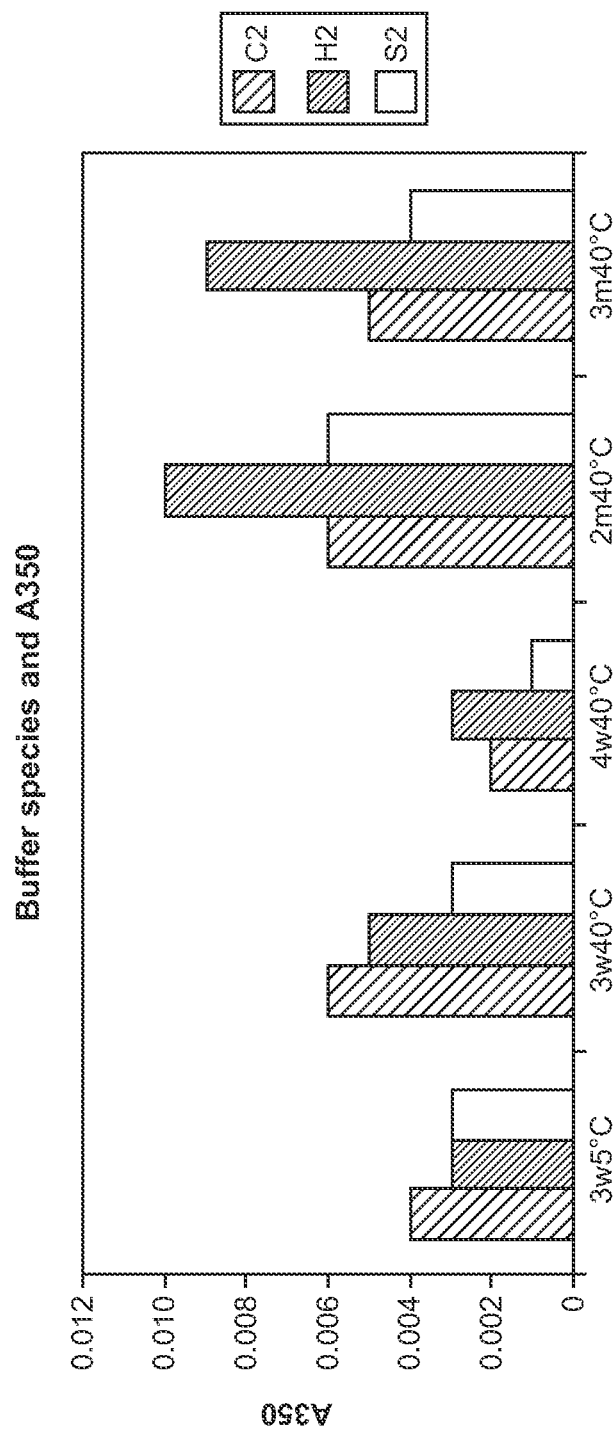

Sodium citrate, L-histidine and sodium succinate were chosen for the buffer species selection study. It appeared that the sodium succinate formulation gave the lowest scattered light intensity almost on every occasion, as shown in FIG. 2. Therefore, sodium succinate was the preferred buffer of choice for the ABT01 formulation.

Effect of L-Arginine Concentration

Since L-arginine was needed for sustaining ABT01 solubility at 30 mg/ml in the formulation, it was important to understand how the L-arginine concentration affected the stability of ABT01. The antibody was formulated at 1 mg/mL in 10 mM sodium succinate, 0.005% polysorbate 80, pH 6.0 buffer with L-arginine concentrations of 2, 3 and 4%.

Figure 3:
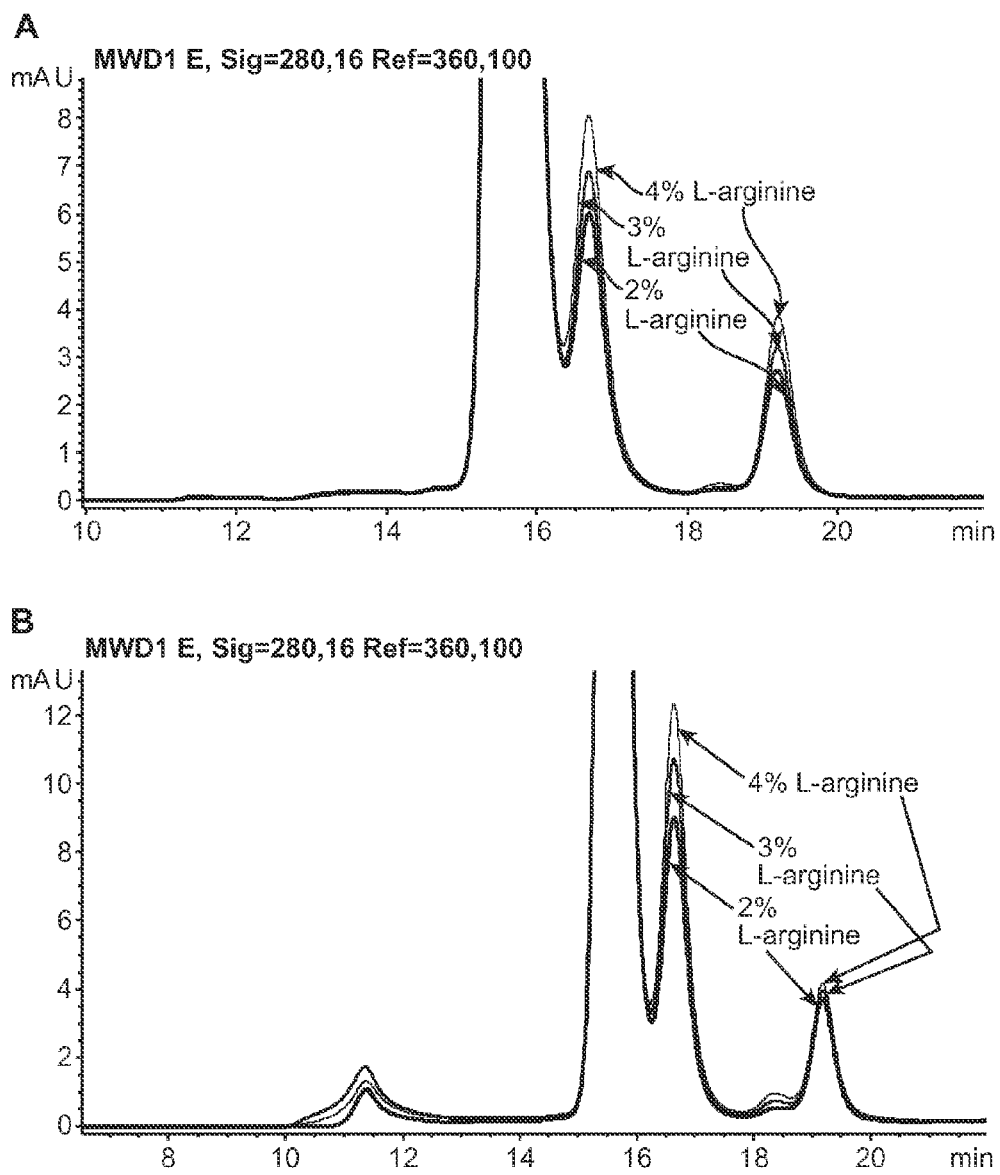

L-arginine concentration did not have significant effect on the formation of acidic species of ABT01. Stability data also showed that the L-arginine concentration did not affect the formation of soluble aggregates at 40° C. or 2-8° C. However, the formation of clips was the predominant degradation pathway and the L-arginine concentration had a measurable effect on the formation of the clips at 40° C. (FIG. 3A) and 50° C. (FIG. 3B). The SEC-HPLC data indicated that higher L-arginine concentration caused slightly faster formation of clips in stability samples stored at both 40° C. and 50° C. It should be noted that this may have been due to the effect of the higher ionic strength, rather than the L-arginine itself. The effect of higher L-arginine concentration on the faster formation of clips was consistently observed across all time points. Consequently, it is desirable to use the lowest L-arginine concentration necessary to sustain the solubility in the formulation. A 3% or 142 mM L-arginine concentration was chosen as a compromise between the necessity for solubility sustenance and the control of the formation of clips.

ABT02

Similar to ABT01, the formulations of ABT02 and their stability were studied. It appeared that ABT02 had limited solubility of approximately 4.6 mg/ml in sodium phosphate buffer (10 mM NaH$_2$PO4/Na$_2$HPO$_4$, 140 mM NaCl). As for ABT01, L-arginine was an effective solubilizer for ABT02; the concentration of ABT02 reached as high as 120 mg/ml in formulation buffer containing 10 mM sodium succinate, 142 mM L-arginine, pH 6.0.

Freeze-thaw stability tests showed that ABT02 was stable against shaking regardless of the presence of surfactant. The presence of 0.005% polysorbate 80 was able to reduce the protein loss due to freeze-thaw cycles. Freeze-thaw induced no changes in soluble aggregates in any of the ABT02 materials used for freeze-thaw studies.

With respect to selection of optimal pH values, lower pH also favored the formation of insoluble aggregates, leading to rapid antibody loss at elevated storage temperatures (40° C. and 50° C.). The formation of soluble aggregates became a competition degradation pathway only when the storage temperature was raised to 50° C. The optimal pH for controlling soluble aggregate formation appeared around 6.0. The optimal pH for controlling clipping appeared slightly higher than 6.0, probably between 6.0 and 7.0. However, higher pH caused substantially more rapid increase of acidic species formation and pH 6.0 was close to the optimal pH for preserving the main charge variants of ABT02.

With respect to buffer species, sodium succinate buffered formulation showed the lowest scattered light intensity and was the preferred buffer species.

ABT03

For ABT03, the effect of different excipients and cryoprotectants on the physical stability of ABT03 was examined. These excipients and cryoprotectants are listed below:

Protein Concentrations
1 mg/ml
5 mg/ml
Buffers
10 mM L-Histidine
10 mM NaSuccinate
Solubilizers
150 mM NaCl
190 mM L-arginine
142 mM L-arginine
Surfactants (w/v)
Polysorbate-20 at 0.001, 0.005, 0.01 and 0.05%
Polysorbate-80 at 0.001, 0.005, 0.01 and 0.05%
Pluronic F68 at 0.001, 0.005, 0.01 and 0.05%
Triton X-100 at 0.005 and 0.05%
Cryoprotectants
7.5% Trehalose
5% Sorbitol
5% Dextrose
7.5% Sucrose ABT03 at 1 mg/ml without surfactant sustained losses approaching 10% over multiple freeze/thaw cycles. Agitation caused only slight losses of up to 2.5%. Surfactants protected ABT03 to varying degrees with the best results achieved for 0.005% polysorbate-20. Pluronic F68 and polysorbate-80 were less effective than polysorbate-20. As ABT03 without surfactant was stable to physical stress at 5 mg/ml, it would seem degradation was due to surface layer interactions as opposed to protein/protein interactions. Thus, although the surfactant may not be necessary at 5 mg/ml, its presence may help to protect ABT03 during the increased physical stress of large production volume freeze/thaw.

Two separate studies assessed the effect of pH. The first study combined histidine buffer with sodium chloride at pH 5.0, 6.0 and 7.0. The subsequent study substituted L-arginine as a solubilizer and shifted the pH up by a ½ unit. The ABT03 concentration was set at ~4.5 mg/ml due to limited material availability.

pH Study 1:
10 mM L-Histidine, 150 mM NaCl, pH 5.0
10 mM L-Histidine, 150 mM NaCl, pH 6.0
10 mM L-Histidine, 150 mM NaCl, pH 7.0
pH Study 2:
10 mM L-Histidine, 190 mM L-arginine, pH 5.5
10 mM L-Histidine, 190 mM L-arginine, pH 6.5
10 mM L-Histidine, 190 mM L-arginine, pH 7.5

The two primary degradation pathways for ABT03 were both strongly affected by pH. Increases in acidic isoforms as measured by salt-elution IEX-HPLC followed the predicted pattern. Higher pH's (>6.0) caused a reduction in percent basic and main peaks that correlated with acidic isoform increases. Although lower pH's had reduced acidic formation, pH shifts too far below the optimum resulted in significant reductions in total peak area. pH 6.0 was the most stable formulation demonstrating the slowest acidic isoform formation and lowest overall peak area losses.

SEC demonstrated that the pH optimum was ~6.0, with lower or higher pH causing greater amounts of clips. SDS-PAGE confirmed the pH optimum of ~6.0 and demonstrated that different sites were cleaved dependent on pH. HMW species formation was pH dependent with lowest levels at pH 6.0.

Effects of Solubilizers

Protein solubilizers were optimized to maximize solubility while minimizing potential negative effects on long term stability. The three stability studies that addressed the solubilizer used for ABT03 are listed below.

Study 1:
10 mM L-Histidine, 150 mM NaCl at pH 5.0, 6.0 and 7.0

Study 2:
10 mM L-Histidine, 190 mM L-arginine at pH 5.5, 6.5 and 7.5

Study 3:
10 mM NaSuccinate, 150 mM L-arginine with and w/o surfactant (0.01% polysorbate-20, polysorbate-80 and Pluronic F68)

The most significant difference in stability between NaCl and L-arginine formulations was in the rate of acidic species formation at accelerated temperatures. Although the formulations with L-arginine started at a lower percent acidic than NaCl formulations (due to starting material variation), the degradation is considerably more rapid.

High pH usually accelerates deamidation. Therefore, it was remarkable that the low pH NaCl formulation degraded faster than the high pH arginine formulation. 190 mM L-arginine appeared to have a greater stabilizing effect than 142 mM L-arginine. Other assays did not demonstrate any significant differences in stability between sodium chloride and arginine formulations.

In addition to inclusion of arginine, a second attempt to harmonize with ABT01/02 formulations was by buffering with sodium succinate instead of histidine. As no difference in stability was observed related to buffer species, sodium succinate was chosen for ABT02 and ABT01 to avoid histidine's tendency to discolor and increase A350 light scattering.

Stability studies on ABT03 suggested a possible difference in deamidation based on buffer species. With harmonization as the goal, sodium succinate and histidine were compared directly to isolate either the solubilizer or the buffer as the source of the change in stability.

Histidine vs. Sodium Succinate Formulations
1. 10 mM L-Histidine, 142 mM L-arginine, pH 6.0, 0.005% polysorbate-20
2. 10 mM L-Histidine, 142 mM L-arginine, pH 6.0, 0.005% polysorbate-80
3. 10 mM NaSuccinate, 142 mM L-arginine, pH 6.0, 0.005% polysorbate-20
4. 10 mM NaSuccinate, 142 mM L-arginine, pH 6.0, 0.005% polysorbate-80

This study indicated the rate of acidic formation did not differ significantly between histidine and succinate buffered formulations. This data identifies L-arginine as the likely source for the difference in ABT03 degradation.

Two studies examined surfactant effect on ABT03 stability.
Study 1:
10 mM NaSuccinate, 142 mM L-arginine, pH 6.0, no surfactant added
10 mM NaSuccinate, 142 mM L-arginine, pH 6.0, 0.01% polysorbate-20
10 mM NaSuccinate, 142 mM L-arginine, pH 6.0, 0.01% polysorbate-80
10 mM NaSuccinate, 142 mM L-arginine, pH 6.0, 0.01% Pluronic F68

Study 2:
10 mM L-Histidine, 142 mM L-arginine, pH 6.0, 0.005% polysorbate-20
10 mM L-Histidine, 142 mM L-arginine, pH 6.0, 0.005% polysorbate-80
10 mM NaSuccinate, 142 mM L-arginine, pH 6.0, 0.005% polysorbate-20
10 mM NaSuccinate, 142 mM L-arginine, pH 6.0, 0.005% polysorbate-80

Results indicated that surfactant-containing formulations had slightly higher clip levels than the surfactant free formulation. This difference was detected both by SEC-HPLC and SDS-PAGE. Polysorbate-20, polysorbate-80 and Pluronic F68 all had slightly higher percent clip levels by SEC and greater intensity on certain LMW bands by SDS-PAGE than the surfactant free formulation. There did not appear to be a significant difference between surfactant types. As the negative impact on long term stability was slight, and the positive effect on physical stability major, inclusion of polysorbate-20 in the ABT03 formulation was preferred.

Other Antibodies Suitable for Co Formulation

Each anti-BoNT/B or E antibody was assessed in a target formulation of 10 mM NaSuccinate, 142 mM L-arginine at pH 6.0. The studies were performed in the absence of surfactant (polysorbate 80).

Antibody Solubility

All BoNT/B and BoNT/E antibodies have been concentrated via Vivaspin ultracentrifugation to >10 mg/mL and measured by SEC-HPLC following overnight storage for any change in aggregate percent. 10 mg/mL was attained without any significant change in percent aggregate for any candidate BoNT/B or E antibody.

Table 6 demonstrates comparative physical stability of the BoNT/B and E antibodies.

TABLE 6

Summary of physical stress data (agitation and freeze/thaw) for BoNT/B and BoNT/E antibodies.

| | Agitation thru 72 hours | | | Freeze/thaw (5 cycles) | | |
|---|---|---|---|---|---|---|
| Antibody | A350 | % Aggregate increase | % total remaining protein | A350 | % Aggregate increase | % total remaining protein |
| ABT07 | 0.171 | 0 | 96 | 0.002 | 0.1 | 97 |
| ABT07 | 0 | 0.1 | 86 | 0 | 0 | 100 |
| ABT09 | 0.009 | 0 | 99 | 0 | 0.4 | 94 |
| ABT10 | 0 | 0 | 97 | 0.001 | 0.4 | 98 |
| ABT11 | 0.012 | 0 | 99 | 0.002 | 0 | 98 |
| ABT12 | 0 | 0 | 103 | 0.008 | 0.6 | 98 |
| ABT13 | 0 | 0 | 98 | 0 | 0 | 101 |
| ABT14 | 0 | 0 | 99 | 0.003 | 0.1 | 99 |
| ABT14 (0.01% PS-80) | 0 | 0 | 101 | 0 | 0 | 101 |
| ABT18 | 0.013 | 1.0 | 89 | 0.064 | 0.2 | 101 |
| ABT21 | 0 | 0 | 97 | 0 | 0 | 98 |

Other important factors in assessing physical stability included percent aggregate because aggregates often have increased immunogenicity, percent truncated because truncated forms are often inactive, and percent remaining total protein. Table 7 summarizes all of these data. On accelerated chemical stability, there were no visual changes observed in any of the antibodies. Therefore, all anti-BoNT/B and E antibodies showed good solubility and physical stability.

TABLE 7

Summary data set for physical stability study performed at 40° C. through the 6 week time point.

| Antibody | Aggregate by SEC | | Truncated by SEC % increase at 40° C. thru 6 W | Acidic by IEX % increase at 40° C. thru 6 W | Total Protein by A280 % remaining thru 6 W at 40° C. |
|---|---|---|---|---|---|
| | Starting % Aggregate | % Aggregate 40° C. at 6 W | | | |
| ABT07 | 1.92 | 1.68 | 0.2 | NA | 96 |
| ABT07 | 8.36 | 7.4 | 0.6 | 13.4 | 100 |
| ABT09 | 1.84 | 1.23 | 0.8 | 34.5 | 106 |
| ABT10 | 0.78 | 1.01 | 2.6 | 21.4 | 100 |
| ABT11 | 5.26 | 4.78 | 3.3 | 16.8 | 98 |
| ABT12 | 6.28 | 7.27 | 5.5 | 28.6 | 100 |
| ABT13 | 4.76 | 3.69 | 0.3 | NA | 99 |
| ABT14 | 0.86 | 0.05 | 0.50 | 21.3 | 99 |
| ABT21 | 0 | 0 | 12.3 | 22.3 | 99 |

The summary of the DSC test results for antibodies in 10 mM NaSuccinate/Succinic acid, 142 mM L-arginine with pH 6.5 is shown below in Table 8.

TABLE 8

DSC transition temperatures for antibodies formulated in 10 mM NaSuccinate/Succinic Acid, 142 mM L-Arginine monohydrochloride, pH 6.0

| Antibody | DSC Transition Temperatures | | | |
|---|---|---|---|---|
| | To | Tm | Tp | Tp – To |
| ABT02 | 65.3 | 71.4 | 74.5 | 9.2 |
| ABT04 | 65.7 | 70.9 | 73.9 | 8.2 |
| ABT01 | 63.2 | 67.3 | 69.7 | 6.5 |
| ABT05 | 63.2 | 67.6 | 70.5 | 7.3 |
| ABT03 | 66.0 | 70.8 | 73.1 | 7.1 |
| ABT06 | 65.6 | 70.5 | 74.1 | 8.5 |

Example 4

Development of Methods for Characterizing Antibody Mixtures

The development of a stable co-formulation required new methods to measure the stability and degradation of the individual antibodies when present in the antibody mixture. A number of methods were developed for this purpose.

A. IEX-HPLC

A IEX-HPLC step gradient method was developed to separate the antibody mixtures by specific antibody, allowing quantification on stability programs, and also to separate each antibody by its charge variants, utilizing the method as stability-indicating for deamidation and other charge-based degradation. The final method was demonstrated to separate each antibody and its charge variants with complete baseline resolution from other antibodies. This method proved to be critical to the success of the coformulation development.

Two studies were performed to optimize the method. A solubility study was performed to confirm that the single antibody and co-antibody mixtures were fully soluble in the IEX starting conditions. A second study was performed which compared the performance of three IEX-HPLC columns when injecting aliquots from a single sample pool (i.e., identical injections over three different columns). Samples from pristine −20° C. pools that were pelleted and then filtered were compared to highly degraded 50° C. stability samples. Pristine sample injections did not cause a decrease in column performance. Degraded sample injections did cause irreversible column damage. If degraded samples were filtered before injection, the column performance issue was partially alleviated. This filtering step, combined with diligent cleaning, resolved the issue.

The finalized IEX-HPLC method utilized a Dionex ProPac IEX-10, 4×250 mm column. Samples were run on Agilent 1100 & 1200 Series HPLC's and chromatograms integrated using Chemstation software. Mobile Phase A: 10 mM $NaPO_4$ monobasic, monohydrate; Mobile Phase B: 10 mM $NaPO_4$ dibasic, heptahydrate 1% NaCl. A 40 minute step gradient method started at 11% B for 1 minute, followed a linear gradient to 41% over 16 minutes, held at 41% B for 1 minute, followed a second linear gradient from 41% to 70% over 10 minutes, held at 70% B for 1 minute, and re-equilibrated at 11% B. Detection was at 229 nm with varying injection amounts. The percents acidic, basic and main peak were reported from the total area percent of each protein related absorbance.

Figure 4:
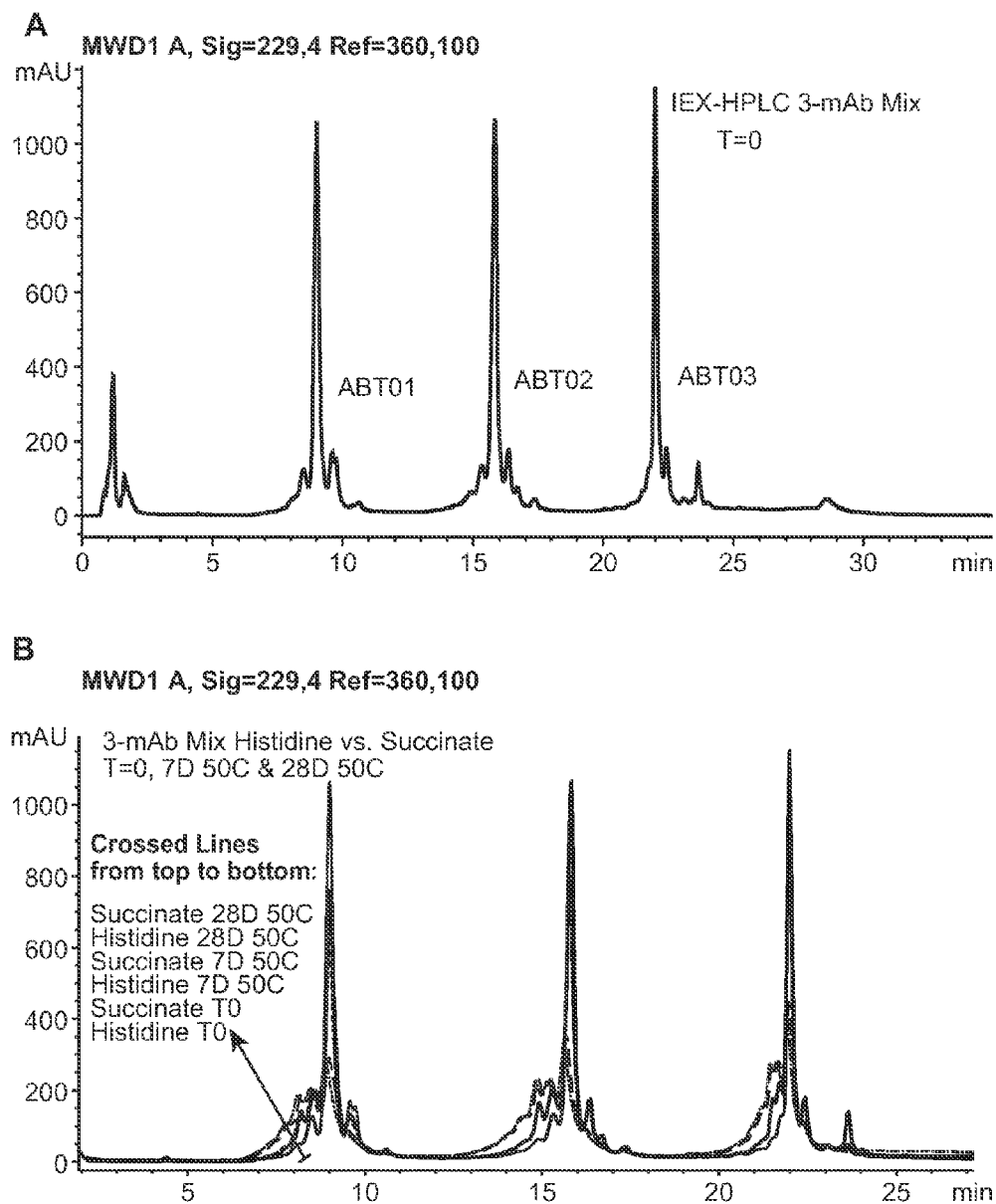

This ion exchange HPLC method separates degradants based on charge, detecting changes in the charge state of the whole antibody including deamidation products and stable deamidation intermediates. FIG. 4A illustrates the charge-based HPLC separation of the 3-antibody mixture (ABT01/02/03). FIG. 4B shows a time course stability overlay for the 3-antibody mixture (ABT01/02/03) illustrating that the method is stability indicating. Each antibody contains a large main peak with varying amounts of acidic and basic species. The step gradient IEX-HPLC method achieved baseline separation between all three antibodies at T=0, allowing for both stability monitoring as well as individual antibody quantitation within the 3-mAb mixture solution.

B. SEC-HPLC

Mixtures of antibodies are typically difficult to adequately characterize by biophysical methods due to biochemical differences. For example, the three IgG1 antibodies, designated ABT02, ABT01, and ABT03, have different retention times when run on a typical size exclusion chromatographic column using conventional methods, resulting in partial overlap of individual monomer peaks and obscuration of impurity peaks. Consequently, this posed a challenge to developing an assay to accurately measure aggregated and fragmented forms in the co-mixture. A method was developed which measured product related impurities while also serving as a stability indicating assay for the antibody mixture.

The method utilized the TSKG 3000 SWXL SEC column manufactured by Toso Hass. A 30 minute isocratic method was used with detection at 280 nm. The mobile phase was 50 mM $NaPO_4$, 0.1 M $(NH_4)_2SO_4$, pH 6.8, 5% acetonitrile. The flow rate was 0.5 ml/min with varying injection amounts. The percent aggregate and percent clip were reported from the total area percent of each protein related absorbance. Samples were run on Agilent 1100 or 1200 Series HPLC's and chromatograms integrated using Chemstation software. Comparison of the actual normalized peak area of the mixture to the theoretical peak area calculated from the individual antibody samples provided a quantitative measurement of aggregation levels in the mixture versus aggregation levels in the individual antibody formulations. This novel approach provided a way to determine whether the different antibodies interacted in the mixture. If the actual peak area was approximately equal to the theoretical peak area, this indicated no interaction between the different antibodies.

Figure 5:
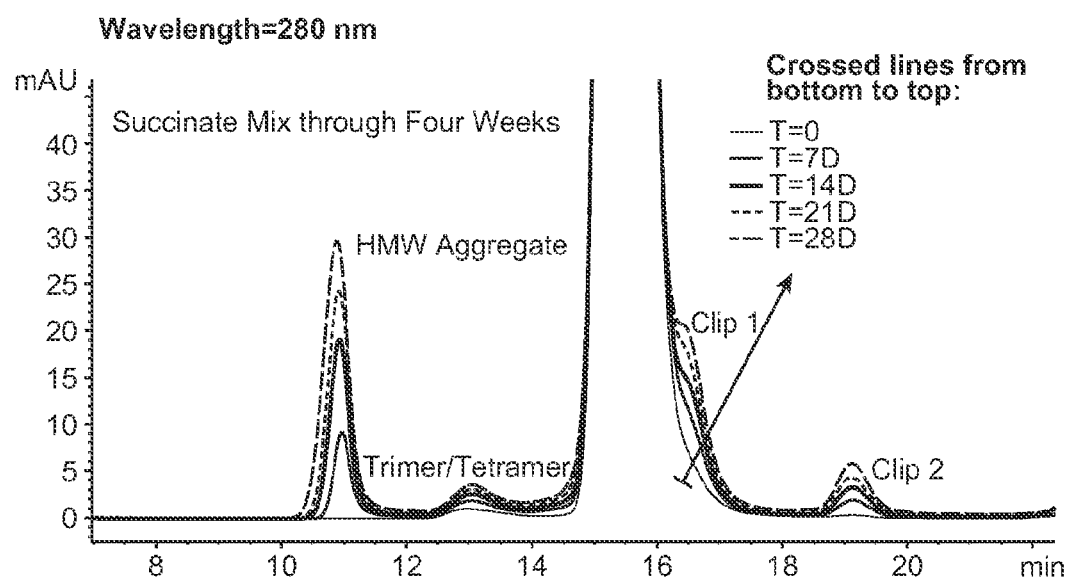

The size-based degradants fell into two categories: truncated forms, i.e. clips or cleaved species, and larger molecular weight forms, i.e. aggregates. In-line 90° light scattering has showed that the HMW forms represent a multimer of unknown size that elutes at around 11 minutes followed by a smaller aggregate with molecular weight between monomer and tetramer at around 13 minutes and the monomer at ~16 minutes. The initial aggregate profile, as well as the size-based degradation rates, is specific to each individual antibody. The hinge-clip shoulder and truncated form molecular weights cannot be determined by 90° light scattering because smaller sized species do not scatter light adequately for molecular weight quantitation. FIG. 5 is a representative chromatographic overlay of the 1:1:1 ratio 3-mAb mixture (ABT01/02/03) illustrating the multimer (trimer/tetramer), aggregate, monomer, main peak shoulder hinge-clip and finally the late eluting low molecular weight species peak. The profile shows a time course for a thermally stressed sample illustrating that the method is stability indicating.

Protein loads of 5 μg to 100 μg showed linearity as measured by an $r^2>0.99$ and relative standard deviation of intra and inter assay of <5% for aggregates and <15% for fragments. It was demonstrated that when one of the three antibodies in the mixture aggregated or was degraded, the impurities could still be accurately determined without interference from the others in the mixture.

C. ELISA

An ELISA assay was developed to measure the relative antigen binding of the different antibodies present in the coformulation. For example, ABT02, ABT01 and ABT03 recognize different antigenic domains of BoNT/A. ABT02 binds to the heavy-chain C-terminus (HCC) domain, ABT01 binds to the heavy-chain N-terminus (HCN) domain, and ABT03 binds to the light-chain heavy-chain N-terminus (LCHN) domain of the toxin. Three sandwich ELISA methods were developed to detect dose dependent binding of these antibodies to their cognate individually cloned and expressed toxin domains. Soluble HCC, HCN, or LCHN antigen domains were purified from an *E. coli* expression system using sequential protein A, Q-sepharose and butyl 650M columns and stored frozen in small aliquots as stock. This stock was used to coat each 96-well plate at 5-10 μg/ml. Following incubation overnight at 2-8° C., the wells were washed and then blocked with assay buffer (1×DBPS, 1% BSA, 0.05% Tween 20). The assay plate was then incubated on a shaker for 2 hours at room temperature to block. The wells were washed and samples of prepared reference standards and test samples composed of a diluted antibody mixture of ABT02, ABT01, ABT03 are added to the plate diluted in assay buffer. Following a 2-hour room temperature incubation to allow for the antibody mixture to bind to the antigen domains, the wells were washed with wash buffer (1×DBPS, 0.05% Tween-20) to remove any unbound reactants. A conjugated goat anti antigen-human IgG Fc labeled with horseradish peroxidase (Pierce catalog no. #31413) diluted at 1:10,000 in assay buffer was added to each well and the assay plate was incubated for two hours at room temperature on a plate shaker. Absorbance readings were obtained at wavelength OD405 nm and graphed on a 4-parameter fit algorithm against the concentration of antibodies to yield a dose dependent sigmoidal curve. The concentration of each sample was calculated using the standard curve.

The qualifications of these methods showed that they are precise, specific and consistently yield a dose-response curve with linearity of r2>0.980. The inter-assay precision of all the ELISA methods was within 15%. Each of the anti-BoNT/A antibodies was found to be specific only to its corresponding domain.

These ELISA methods are advantageous in that they do not require the use of the biologically active toxin which eliminates any safety concerns. Moreover, this model of using non-toxic toxin subunits as the basis for a binding ELISA to measure activity of an antibody mixture can potentially be applied to other BoNT subtypes as well as other biological toxins where the therapeutic product is composed of multiple antibodies.

Example 5

Co-Formulation Development for Anti-BoNT/A Antibodies

Anti-BoNT/A Antibody Co-Formulations

Two key elements in designing the co-formulation were the buffer species and the pH.

A. Choice of Buffer Species

The primary purpose of the study was to identify the buffer component for a 1:1:1 co-mixture of ABT02, ABT01 and ABT03 by comparing chemical stability of histidine versus succinate buffered formulations while keeping pH and all other excipients the same. This comparison was performed on the individual antibodies along with the 3-antibody mixture. The buffer species investigated based on results obtained during early stability studies of ABT03 buffered in histidine vs. succinate (see example 3). (ABT02 and ABT01 did not show any significant differences on short term accelerated stability between histidine and succinate buffers). The ABT03 studies had two important outcomes that could affect the final excipient choice. The first result obtained was that ABT03 appeared significantly more stable at accelerated temperature in histidine buffer. Refrigerated storage did not show any drug profile changes, however histidine was preferred as accelerated temperature degradation can be predictive of long term degradation. The second result was due to light exposure of histidine formulated ABT03 sample vials. The light exposed samples exhibited solution discoloration and an associated interference with A280 protein concentration measurements. No change in degradation was observed by SEC or IEX-HPLC. A study was therefore designed to determine if the antibody mixture showed a similar superiority of histidine over succinate buffer at accelerated temperature and to decide if the difference was significant enough to choose histidine over succinate (thus requiring the drug be stored protected from light).

Figure 6A:
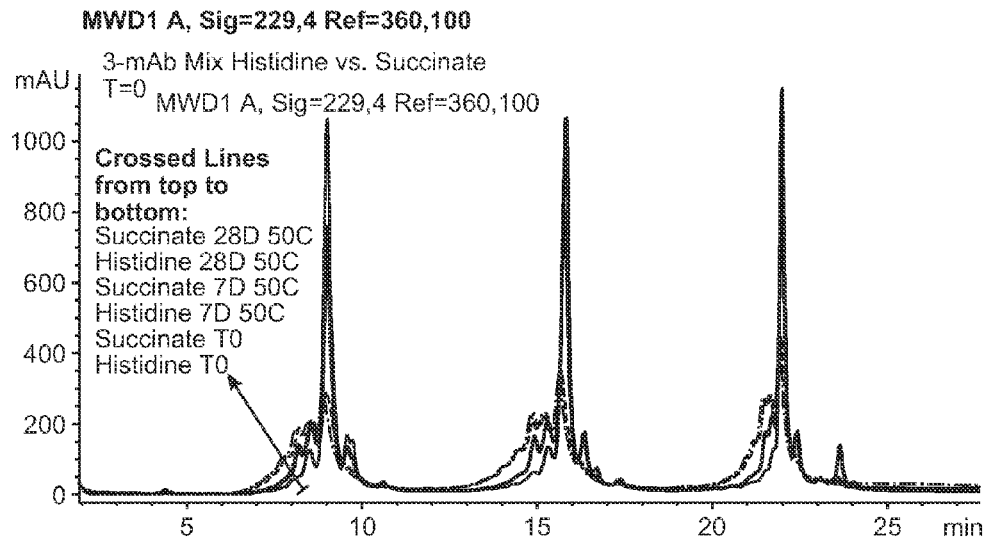

The results from the stability evaluation indicated by IEX-HPLC, no differences in charge-based degradation for the 3-antibody coformulation were apparent between histidine and succinate buffered formulations (FIG. 6).

Figure 6B:
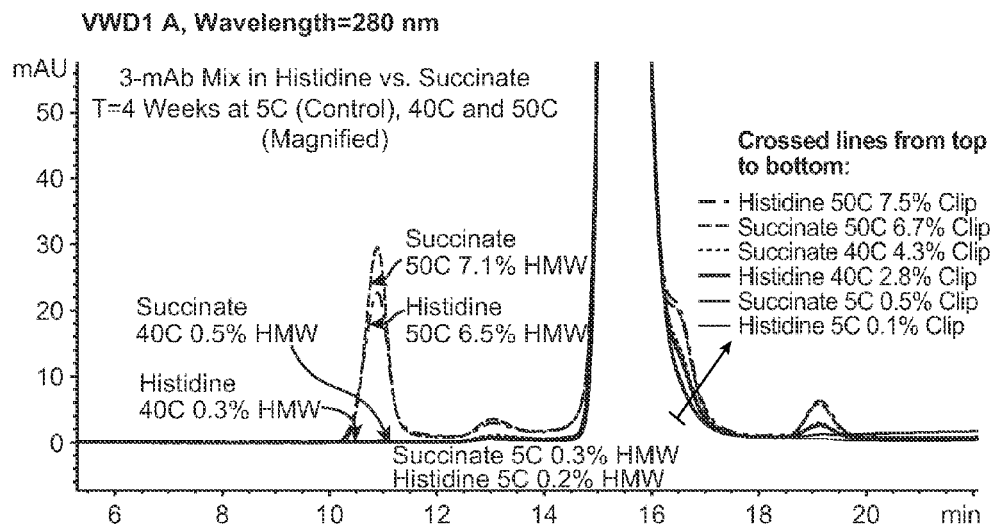

SEC-HPLC revealed that the 3-antibody mixture was slightly more stable to aggregation in histidine buffer. FIG. 6B shows a SEC-HPLC chromatographic overlay for samples stored at 40° C. and 50° C. for four weeks. FIG. 7 illustrates that the aside from two apparent outliers, the two buffers had equivalent stability to clipping. There were slight differences in stability to size based degradation as measured by SEC-HPLC. ABT02 was more stable to aggregation in succinate buffer, while ABT03 was more stable in histidine. ABT01 aggregate results varied and appeared to represent run to run variation. The 3-antibody mixture was slightly more stable to aggregation in histidine buffer. Although slight differences existed in levels of truncated species, none was significant enough support choosing one buffer species over the other.

An in-line Precision 90° light scattering detector with refractive index measurement was utilized to quantify the molecular weight average of each peak 90° light scattering analysis of the 3-antibody mixture, using an in-line Precision 90° light scattering detector with refractive index measurement, showed that at T=0, the aggregate peak represented an approximate molecular weight of ~350 kDa for both buffer species. This molecular weight calculates to dimer plus a truncated form. (It is notable that all of the individual antibodies quantitated to the molecular weight of a monomer plus a truncated species). After four weeks at 40° C., the succinate buffered sample still calculated to dimer+, but the histidine buffered sample had changed significantly. The histidine buffered sample at 40° C. after four weeks represented a total of three aggregate peaks. Two new large multimer peaks eluted at 10 and 11 minutes. The peak at 13 minutes that was dimer+ at T=0 now had an average molecular weight of >600 kDa, (tetramer). 90° light scattering results are presented in Tables 9 and 10.

TABLE 9

Calculated* molecular weights for each peak on SEC-HPLC. Numbers reported in kDa.

| Sample | Temp (° C.) | Peak Elution Time On SEC-HPLC | | | | |
|---|---|---|---|---|---|---|
| | | 11' | 13' | 13'A | 13'B | 16' |
| ABT02 | −20 | | 265 | | | 157 |
| | 40 | | 540 | | | 162 |
| ABT01 | −20 | | 249 | | | 160 |
| | 40 | 1691 | 194 | | | 117 |
| ABT03 | −20 | | | 248 | 202 | 156 |
| | 40 | | 339 | | | 155 |

*90° light scattering measurement combined with a refractive index signal and UV detection allows calculation of the molecular weight average of the species falling under a single peak. Calculations can then be performed determining the approximate size of the aggregate (i.e., dimer, trimer, tetramer, etc).

TABLE 10

Possible identity of HMW peaks.

| Sample | Temp (° C.) | Peak Elution Time On SEC-HPLC | | | |
|---|---|---|---|---|---|
| | | 11' | 13' | 13'A | 13'B |
| ABT02 | −20 | | Monomer + 115 KDa | | |
| | 40 | | Trimer + 90 KDa | | |
| ABT01 | −20 | | Monomer + 99 KDa | | |
| | 40 | Multimer | Monomer + 44 KDa | | |
| ABT03 | −20 | | | Monomer + 98 KDa | Monomer + 52 KDa |
| | 40 | | Dimer + 67 KDa | | |

For the 3-antibody mixture, the most important difference between the two buffer species was noted in the A350 and A280 measurements. Some histidine buffered samples had increased A350 light scattering levels which at times interfered with A280 protein concentration measurement. Several stressed samples showed saturated A280 signals without a spike in A350 levels. In contrast, there were only slight increases in A350 measurements for succinate buffered samples and such trends were normal for stressed samples. Slight yellowing and opalescence of histidine buffered solutions was evident in several accelerated stability samples, but visual changes did not necessarily correlate with A350 and A280 changes. No visual changes were detected in 2-8° stored samples. Although A280 interference was only observed at accelerated temperature, the risk associated with lot failure due to stability concerns was high enough to eliminate histidine from consideration for the coformulation.

B. Choice of pH

This study compared ABT02, ABT01, ABT03 and their mixtures in 10 mM NaSuccinate, 142 mM L-arginine, 0.005% Tween-80 at three different pH's. The study consisted of both chemical and physical stability studies. Chemical stability studies were performed at refrigerated (2-8° C.), accelerated (25° C.) and stressed (40° C. & 50° C.) temperatures. Freeze/thaw studies were performed through 10 cycles to −20° C. Agitation studies were analyzed for room temperature shaking through 72 hours at 1000 RPM.

(i) Effect of pH on Physical Stability

Individual antibody formulations and the 3-antibody mixture were assessed to determine the effect of agitation or freeze/thaw stress. These studies determined that through 72 hours rotation at 1000 RPM, or 10 freeze/thaw cycles, no changes were detected by any of the assays utilized. Visual appearance and A350 measurement did not show any significant changes due to agitation stress. No protein losses were apparent for any samples by either A280 measurement or by SEC-HPLC total peak area. Percent aggregate changes were due only to run to run variation and did not reflect a change in aggregate levels. No change in percent clip was expected, and none was observed.

FIG. 8 presents aggregate data for ABT02, ABT03 and the ABT02/11 mixture to illustrate two points: 1) Aggregate levels are constant through 10 freeze/thaw cycles, and 2) aggregate levels of mixtures are the average of the aggregate levels for each individual antibody.

(ii) Effect of pH

At accelerated and stressed temperatures, 3-antibody mixture solutions at all three pH's remained clear and colorless except at very stressed (50° C. at 6 weeks) conditions. Light scattering (A350) through the 3 month time point increased only after storage at 50° C. at all three pH's. Significant aggregation only occurred at 50° C. Aggregation and cleavage occurring at 50° C. was fastest at pH 5.5. Absorbance at 280 nm and SEC-HPLC total peak area both showed no change in total protein for any stressed samples at all three pH's. Results from real time storage stability studies at the three pH's are shown in FIG. 9.

Comparative Stability of Co-Formulated and Individually-Formulated Antibodies

1. Long Term Stability of the 3-Antibody Mixture

Figure 10A:
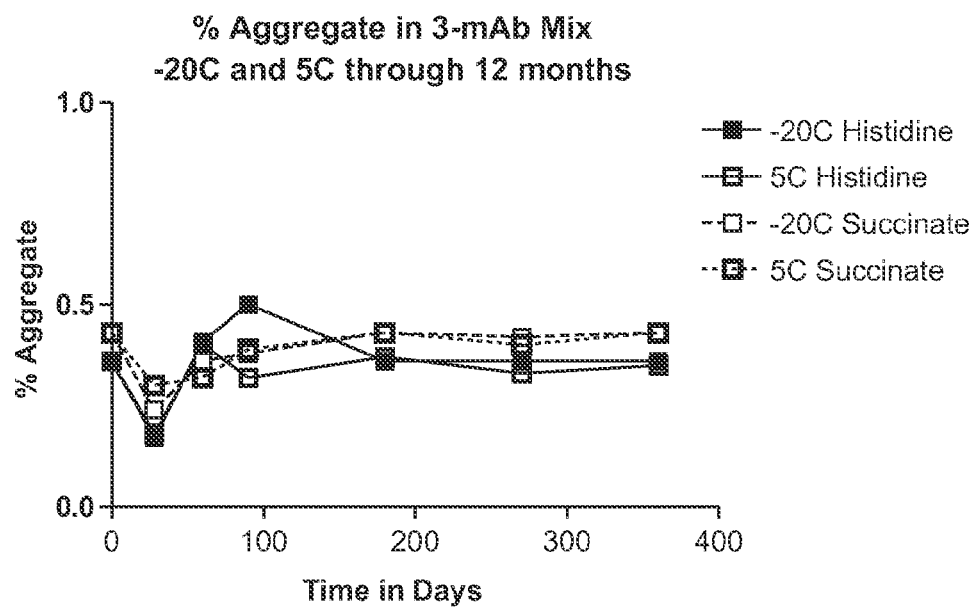
Figure 10B:
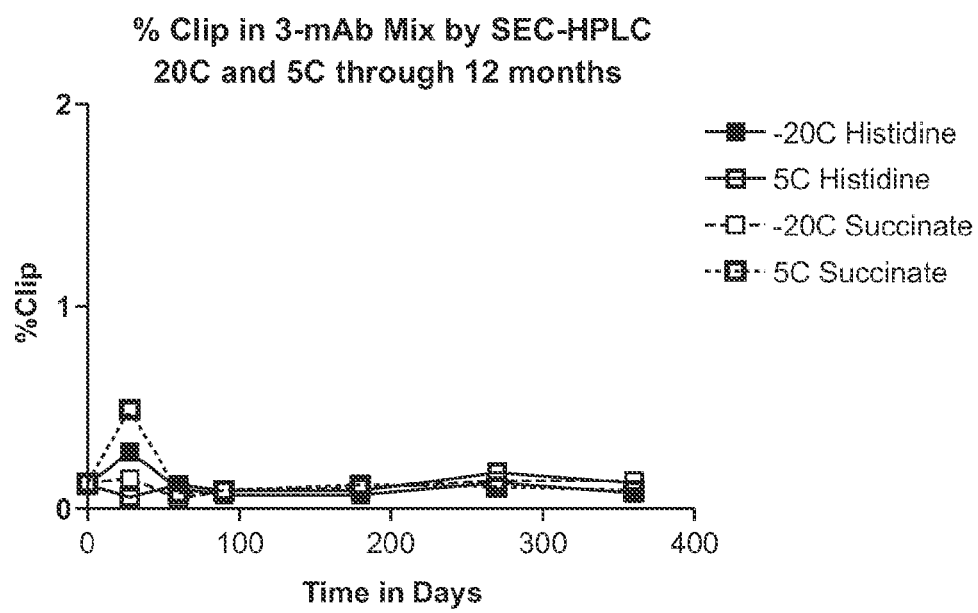
Figure 10C:
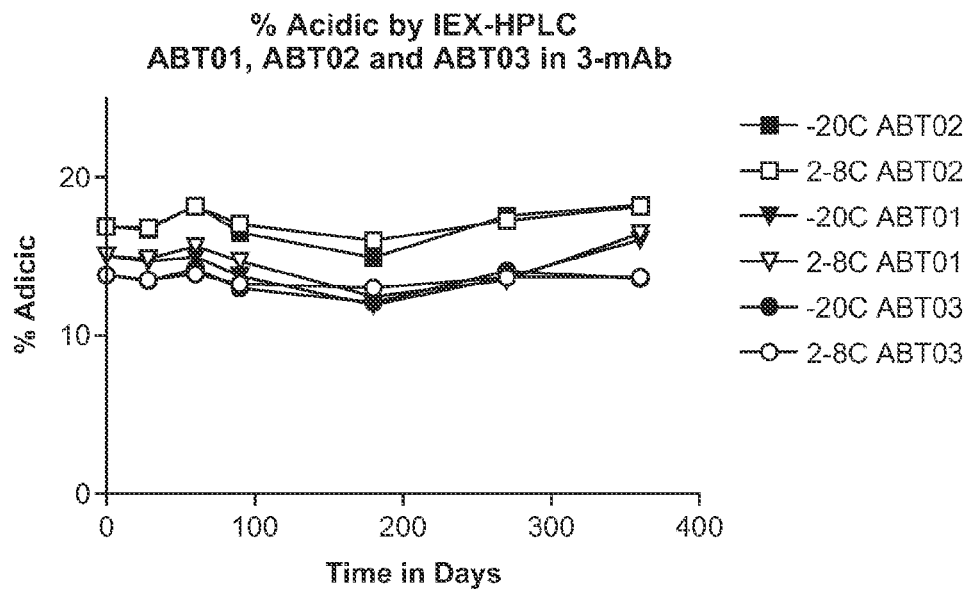

The 3-antibody mixture in the formulation containing 10 mM NaSuccinate/Succinic Acid, 142 mM L-arginine, pH 6.0, 0.005% Tween-80 remained stable at 2-8° C. for at least 1 year. There was no significant change in visual, appearance, A350 light scattering or A280 protein concentration measurements. No aggregate changes were observed for the 3-antibody mixture at 2-8° C. (FIG. 10A), and the hinge-clip shoulder showed only the integration related run to run variation (See FIG. 10B). FIG. 10C shows that the each antibody stored in the mixture is stable to charge-based degradation when stored at refrigerated or frozen temperatures.

2. Determining the Effect of Mixing on Antibody Stability

Experiments were performed to determine the effect of mixing the three different antibodies on each antibody's stability, addressing the question of whether the antibodies interact in solution.

A. IEX-HPLC

IEX-HPLC showed no significant differences in charge-based stability between the ABT02, ABT01 or ABT03 individual formulations and the ABT02, ABT01 or ABT03 antibodies in the mixture formulation.

B. SEC-HPLC

Figure 11:
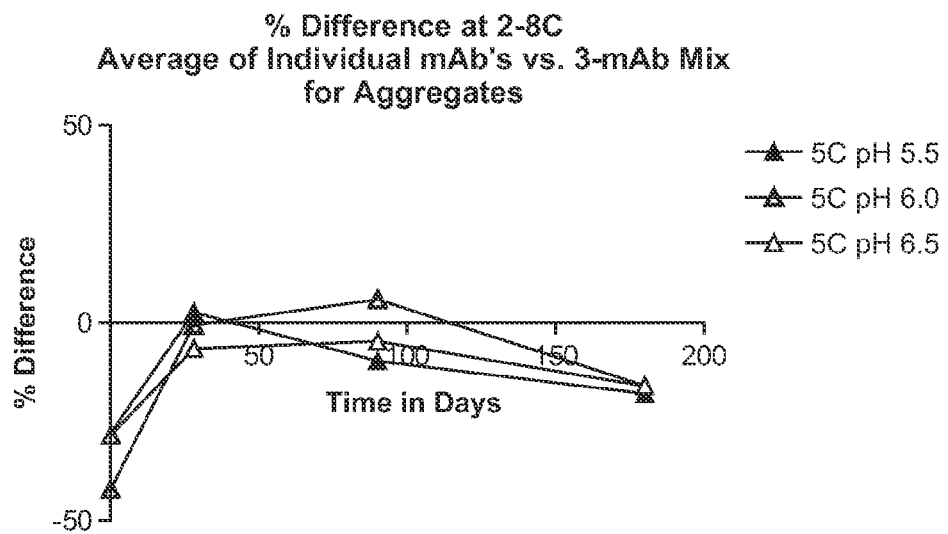

A complete analysis of SEC-HPLC results for the individual antibodies versus the 3-antibody mixture was performed at all temperatures and time points. The percentage of antibody cleaved in the 3-antibody mixture generally fell below the average of the three individual antibodies. FIG. 11 illustrates that the aggregate levels for the 3-antibody mixture are very near the average of the aggregates for the individual mAb's at the recommended storage temperature.

C. DSC

Figure 12A:
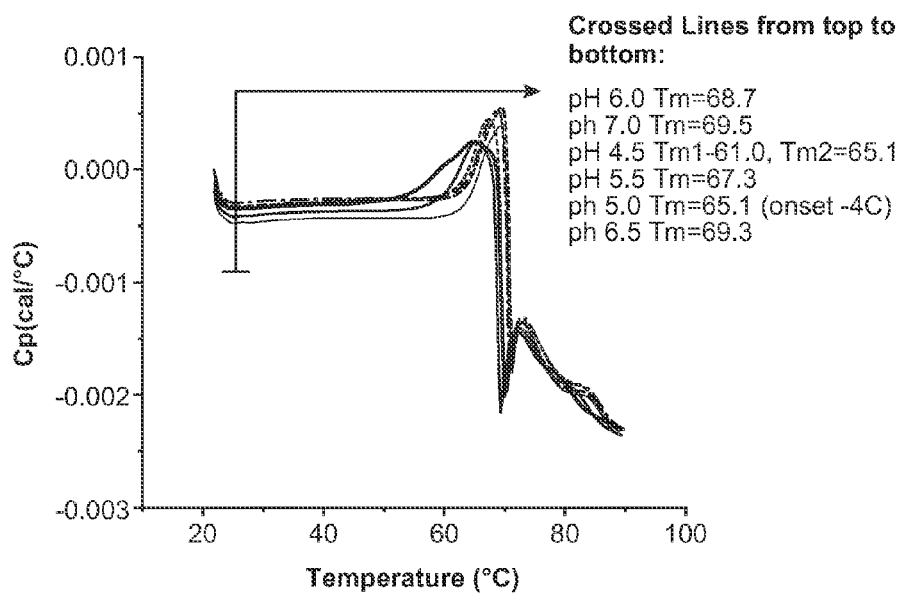

Differential scanning calorimetry was performed to determine the thermal stability of the 2- and 3-antibody mixtures as compared to the individual antibodies. The 3-antibody mixture was exchanged into appropriate buffers at pH's from 4.5 to 7.0 and the solutions scanned by DSC from 20-90° C. ABT02, ABT01 and ABT03 showed a DSC profile common to many monoclonal antibodies. At neutral pH, the DSC profile showed a single transition at ~70° C., followed by protein precipitation apparent by the drop in Cp following the transition peak. At lower pH's, a second transition (Tm1) shouldered strongly on the front of Tm2. Tm1 resolved into a shoulder at pH 4.5 and 5.0. Tm2 was slightly broader at pH 5.5, but no Tm1 shoulder was apparent. Tm2 for the mixture increased with increasing pH. FIG. 12A shows an overlay of pH screen thermograms.

Figure 12B:
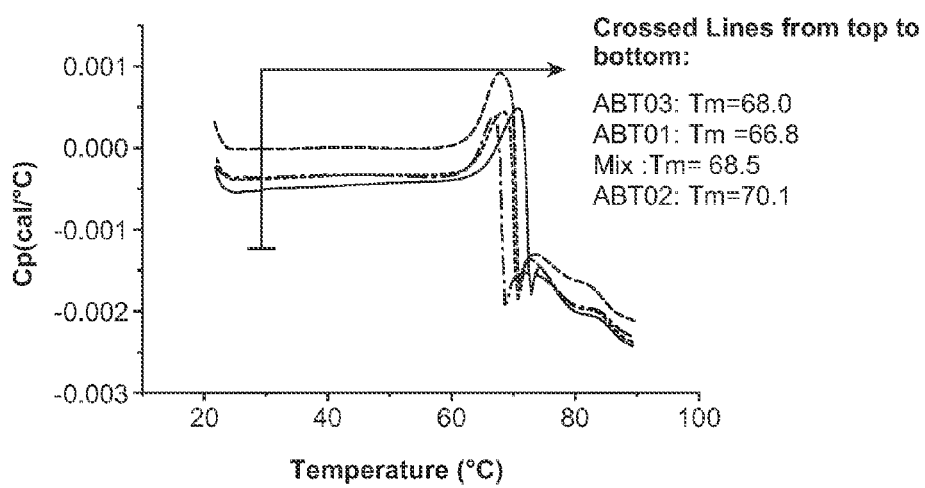

The 2- and 3-antibody mixtures were analyzed by DSC in the succinate buffered formulation at pH 6.0. Tm2 of the 3-mAb mixture was at or very near the average of the Tm's for each individual mAb (FIG. 12B). Tm's for the 2-antibody mixtures fell between the Tm's for the individual antibodies in all cases, indicating that thermal denaturation of the 2- and 3-antibody mixtures is not significantly different from the individual antibody solutions.

3. Stability of Lyophilized Anti-BoNT/A Monoclonal Antibody Mixture (ABT01, ABT02 and ABT03)

The three anti-BoNT/A monoclonal antibody mixture (formulated in 10 mM sodium succinate, 142 mM L-arginine monohydrochloride at pH 6.0) was lyophilized with a conventional lyophilization cycle (Table 11). The lyophilized three-mAb mixture product showed good cake morphology if the total antibody concentration in the initial liquid solution was approximately 20 mg/mL or higher. The lyophilized product showed fast reconstitution speed and complete content recovery as measured with UV spectrometry as well as two different HPLC methods (size-exclusion and ion-exchange). The lyophilized product showed markedly improved stability compared with the liquid counterpart. The data in Table 12 demonstrated that the lyophilized product showed almost no change in any of the monitored degradants after storage at 50° C. for 4 weeks.

TABLE 11

Lyophilization cycle

| Process | Temperature | Vacuum pressure | Duration |
| --- | --- | --- | --- |
| Shelf loading | Ambient | Atmosphere | ~15 min. |
| Freezing | −50° C. | Atmosphere | 400 min. |
| Primary drying 1 | −30° C. | 180 mT | 720 min |
| Primary drying 2 | −25° C. | 200 mT | 1000 min. |
| Secondary drying | 25° C. | 200 mT | 400 min. |

TABLE 12

Comparison of major degradation species of the three-mAb mixture in the lyophilized and liquid state after storage at 50° C. for 1 month

| | % Degradants by SEC-HPLC | | % Total acidic species by WCX-HPLC | | |
| --- | --- | --- | --- | --- | --- |
| State | Total aggregates | Total clips | ABT02 | ABT01 | ABT03 |
| T = 0 | 0.50 | BQ* | 22.2 | 15.0 | 23.4 |
| Lyophilized | 0.63 | BQ | 22.5 | 15.3 | 23.7 |
| Liquid | 5.4 | 8.7 | 64.2 | 54.7 | 65.3 |

*BQ—below quantification

4. Long-Term Stability of Anti-BoNT/A Monoclonal Antibody Mixture

Figures 13, 14:
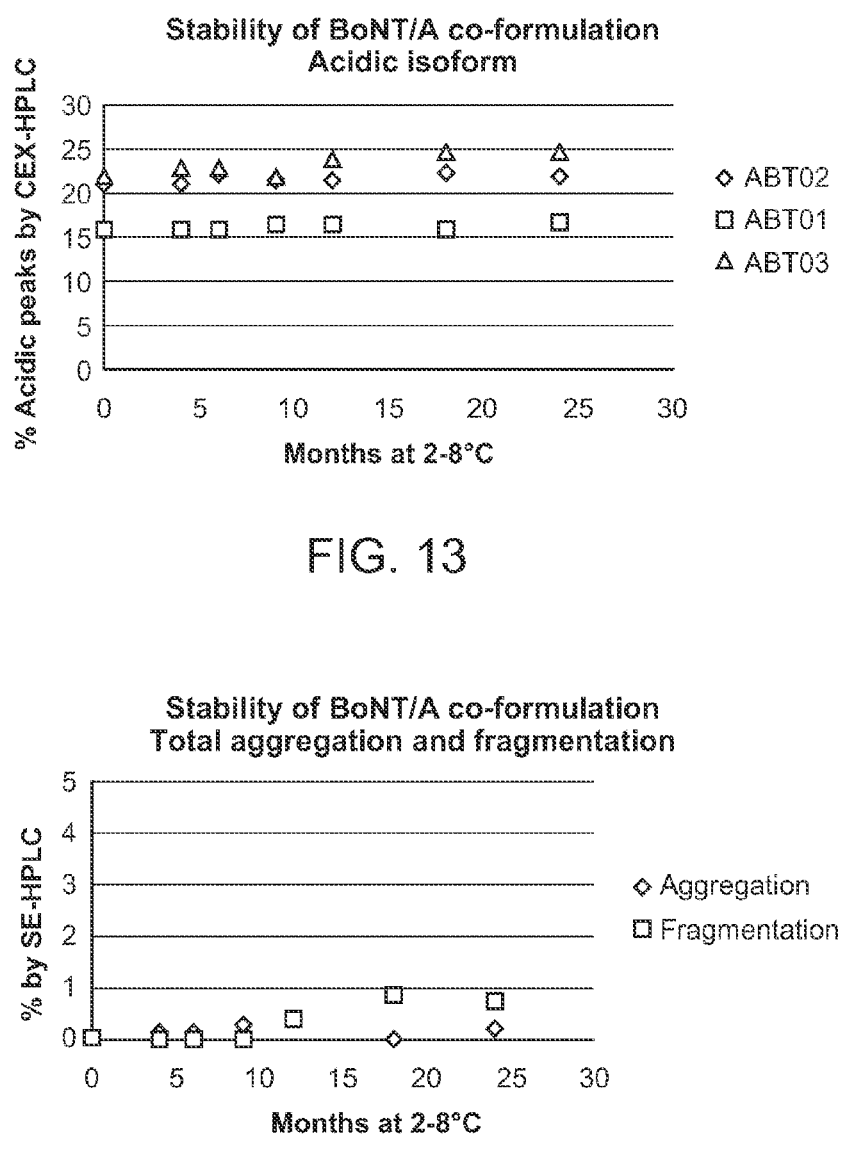

The stability of the three anti-BoNT/A antibody mixture (ABT01/ABT02/ABT03) product was monitored through a QC stability program. The product remains stable after 24 months storage at 2-8° C., as no significant changes in the impurity profile are observed (FIGS. 13 and 14).

5. Binding Activity of Co-Formulated Antibodies

Figure 15:
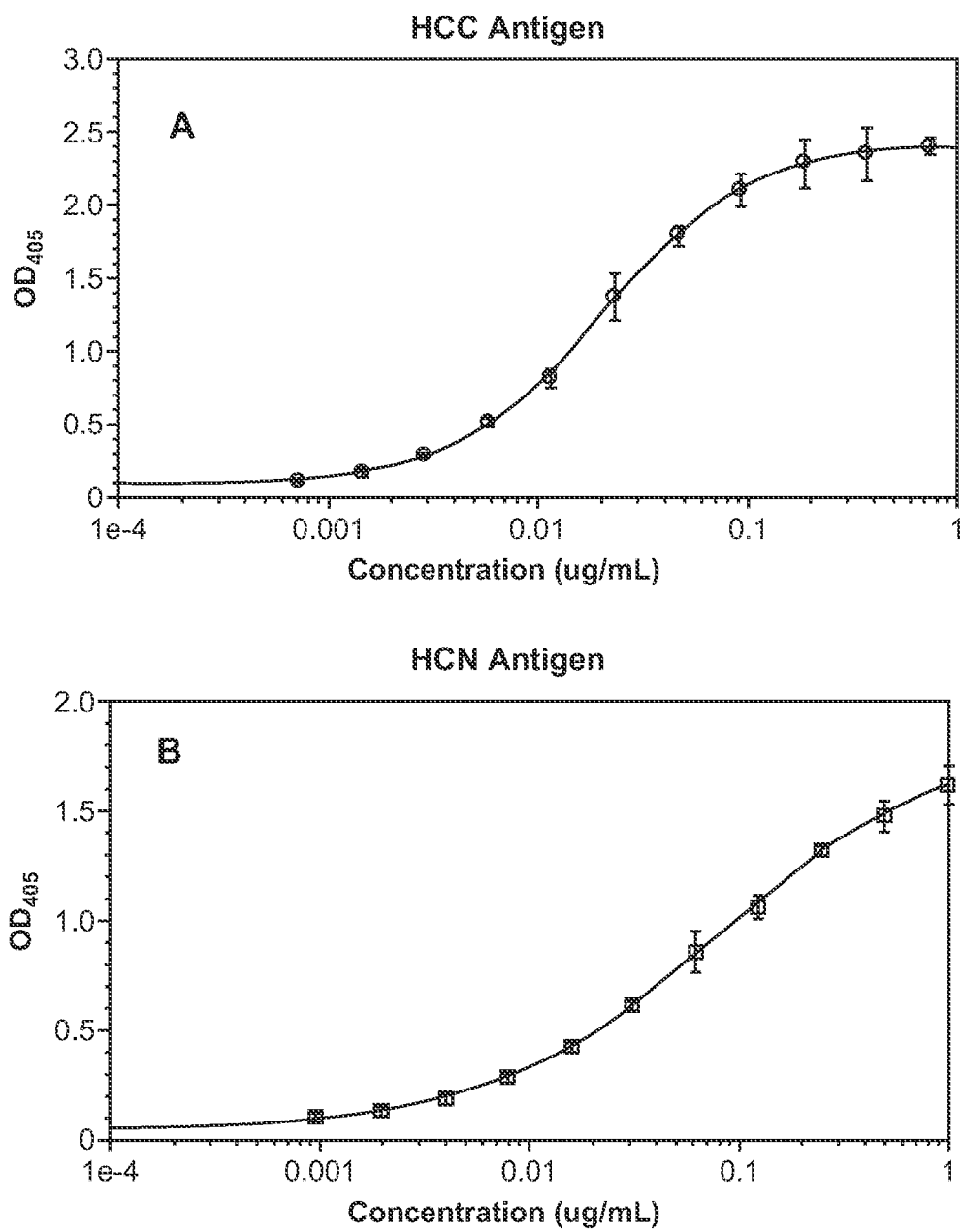

FIG. 15 shows ELISA data demonstrating the binding of (A) ABT02, (B) ABT01 and (C) ABT03 within the context of a 3-antibody mixture. Antibodies were co-formulated at a 1:1:1 ratio in 10 mM sodium succinate/succinic acid, 142 mM L-arginine, 0.005% Tween-80 at pH 6.0. and stored at 2-8° C. for ~>1 week prior to testing in the ELISA assay described above in this example.

In addition, the antibodies in the ABT01/ABT02/ABT03 mixture retained their binding activity as determined by a toxin domain binding ELISA assay, after 24 months storage at 2-8° C. (FIG. 16).

Choosing a drug product or drug substance formulation nearly always involves choosing excipients that represent a compromise, balancing the drug's stability to competing degradation mechanisms. Lowering the pH may reduce deamidation, but it also tends to increase clipping and some types of aggregation. A key challenge in formulating the 3-antibody mixture was in balancing not only each molecule's stability to each degradation mechanism, but also in balancing the degradation mechanisms and rates of degradation for each antibody.

The optimal formulation for the mixture of ABT02, ABT01 and ABT03 at a 1:1:1 ratio is 10 mM sodium succinate/succinic acid, 142 mM L-arginine, 0.005% Tween-80 at pH 6.0.

Example 6

Individual Formation and Co-Formulation Development for Anti-BoNT/B Antibodies

1. Stability of Individually Formulated Anti-BoNT/B Antibodies

Pre-formulation development studies were performed to assess the solubility, physical and chemical stability of each of the transiently expressed BoNT Type B antibodies to support the candidate selection for co-formulation development. Each mAb was assessed in the formulation of 10 mM NaSuccinate, 142 mM L-arginine at pH 6.0. With one exception, studies were performed in the absence of surfactant (polysorbate 80).

The BoNT/B antibodies assessed (listed below together with protein concentrations) were all soluble to the target concentration of 10 mg/ml. DSC profiles were within normal ranges for all monoclonal antibodies. Assays have been developed which are stability indicating and sufficient for development use. This initial stability screen showed that none of the transiently expressed BoNT/B candidates assessed had any strong tendency toward degradation. Although percent aggregate was high in the protein A pool for ABT12, this aggregate was not intrinsic and does not re-form upon storage at 2-8° C. The three antibodies chosen for continued development were ABT10, ABT14 and ABT17. ABT10 and ABT14 are both stable to physical and thermal stress. ABT17 is sensitive to agitation stress but not freeze/ thaw stress. However, the A350 increases and losses in total protein can be eliminated by addition of polysorbate 80.
ABT07: 1.49 cm$^{-1}$[g/L]$^{-1}$
ABT08: 1.49 cm$^{-1}$[g/L]$^{-1}$
ABT09: 1.44 cm$^{-1}$[g/L]$^{-1}$
ABT10:1.47 cm$^{-1}$[g/L]$^{-1}$
ABT11: 1.37 cm$^{-1}$[g/L]$^{-1}$
ABT12: 1.59 cm$^{-1}$[g/L]$^{-1}$
ABT13: 1.44 cm$^{-1}$[g/L]$^{-1}$
ABT14: 1.52 cm$^{-1}$[g/L]$^{-1}$
ABT17: 1.34 cm$^{-1}$[g/L]$^{-1}$
ABT17G: 1.34 cm$^{-1}$[g/L]$^{-1}$ 2. Stability of Transient BoNT/B 3-mAb Mixes:

This study assessed stability for the anti-BoNT/B antibody mixtures. The study tested physical (freeze/thaw and agitation) and chemical stability through 6 weeks at 40° C. and three weeks at 50° C. The mixture includes anti-BoNT/B antibodies ABT10, ABT14 and ABT17. Each transiently expressed antibody has shown its own individual sensitivity to both physical and chemical stress, and this study assesses temporary storage and shipping conditions as well as short term chemical stability for the mixes during use. The antibodies were formulated in 10 mM NaSuccinate/Succinic acid, 142 mM L-arginine at pH 6.0 at 1 mg/ml total protein (1:1:1 ratio).

Analytical methods used in this study included the following:

Visual: Observes visual changes in solution against a black/white background

UV absorbance at 280 nm: Measures total protein in solution

A350: Measures the presence of large particles that scatter light

SEC-HPLC: Measures size-based degradation (aggregation and truncation)

CEX-HPLC: Measures charge-based degradation (formation of acidic species).

Chemical stability was assessed at 40° C. through 6 weeks and 50° C. through three weeks. A 5° C. sample was pulled at four weeks. The physical stability study included agitation (1000 orbital shaking for 72 hours) and freeze/thaw (to −70° C. through 5 cycles).

Figure 17:
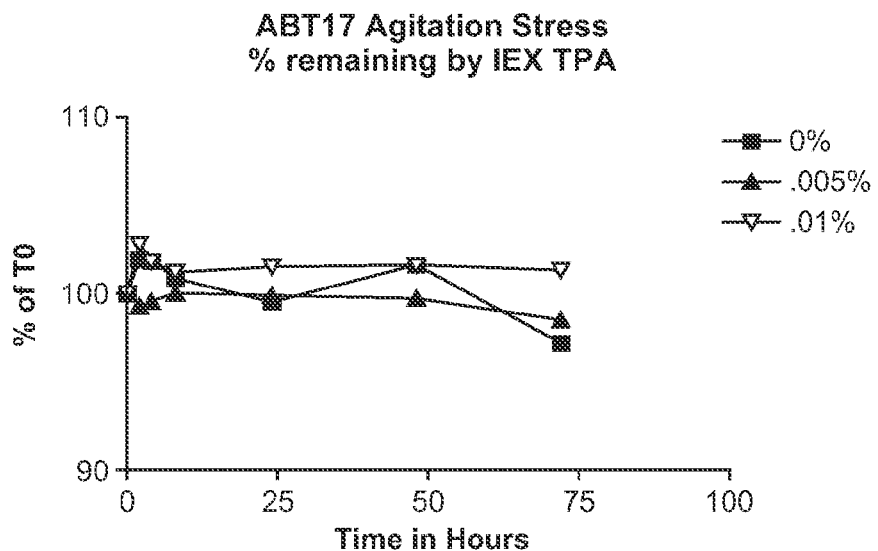

The BoNT/B Mix study was performed without surfactant for the chemical and freeze/thaw arms, but with two additional formulations containing 0.005% and 0.01% polysorbate 80 for the agitation arm due to previous observations suggesting ABT17 was agitation sensitive. Interestingly, no significant protein losses due to agitation were observed in this study (FIG. 17). FIG. 17 shows percent remaining compared to T=0 by CEX-HPLC total peak area for ABT17 for three levels of polysorbate 80. The greatest loss was in the surfactant free sample at just over 2%.

Figure 18:
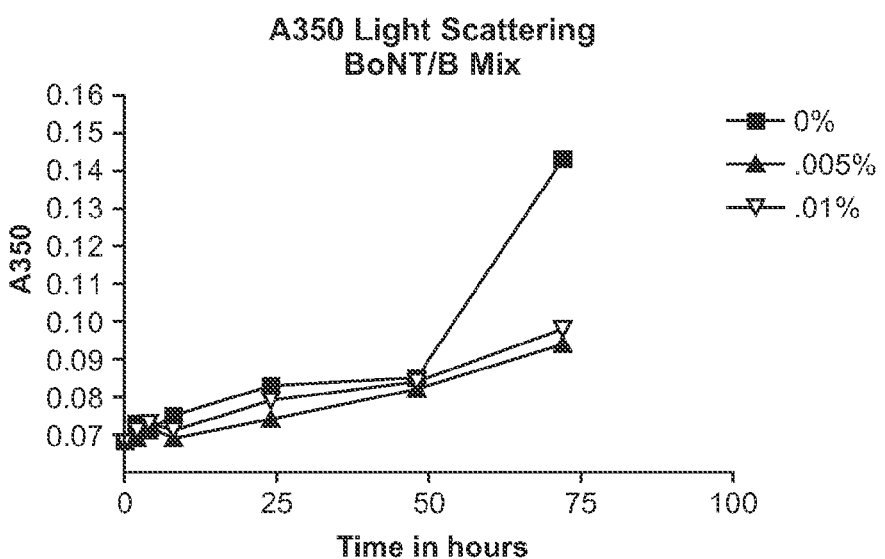

In additional to this positive result, only A350 light scattering showed increases during the shaking stress (FIG. 18). There were no significant losses in overall protein (FIG. 19) and no increase in percent aggregate by SEC-HPLC (FIG. 20). No changes in the charge-based profile for each antibody were observed.

None of the individual transient BoNT/B antibodies showed significant change on freeze/thaw stress. Similar to the individual antibodies, the antibody mixtures showed no significant change either. There were no losses in total protein, no increases in A350 light scattering and no increase in percent aggregate measured by SEC-HPLC. Table 13 summarizes the freeze/thaw data for the BoNT/B mix study.

TABLE 13

Summary of Freeze/thaw stress data for BoNT/B mix study.

| mAb | Assay | Freeze/thaw cycles | | | |
|---|---|---|---|---|---|
| | | 0 | 1 | 3 | 5 |
| Mix | Visual | CC | CC | CC | CC |
| Mix | A350 | 0.028 | 0.029 | 0.029 | 0.031 |
| Mix | % total protein by SEC-HPLC TPA | 100 | 100 | 99 | 100 |
| ABT10 | % of T0 by CEX - ABT10 peak area | 100 | 100 | 99 | 100 |
| ABT14 | % of T0 by CEX - ABT14 peak area | 100 | 98 | 98 | 99 |
| ABT17 | % of T0 by CEX - ABT17 peak area | 100 | 98 | 98 | 98 |
| Mix | % Aggregate | 0.83 | 0.90 | 0.82 | 0.93 |
| Mix | % Clip | 0 | 0 | 0 | 0 |

Figure 21:
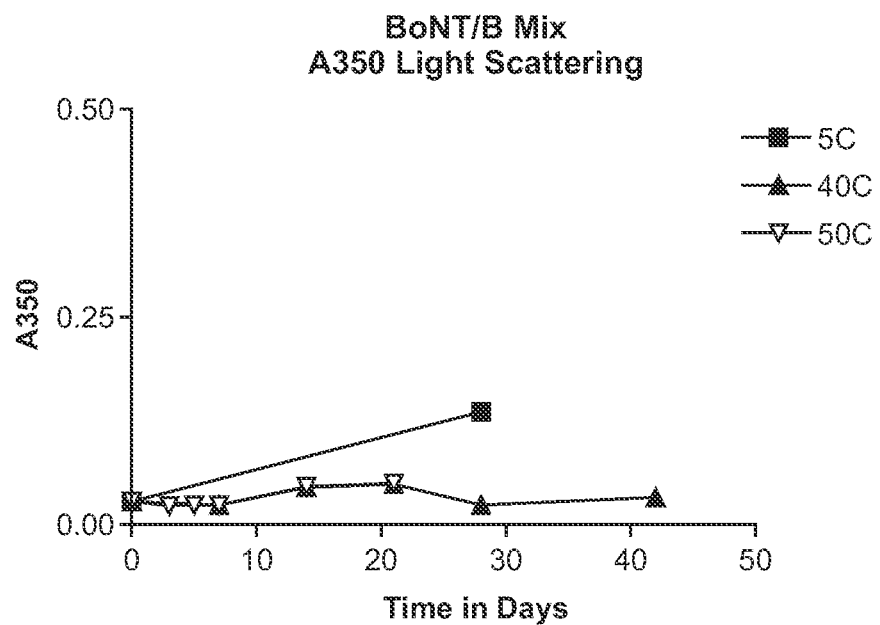
Figure 22:
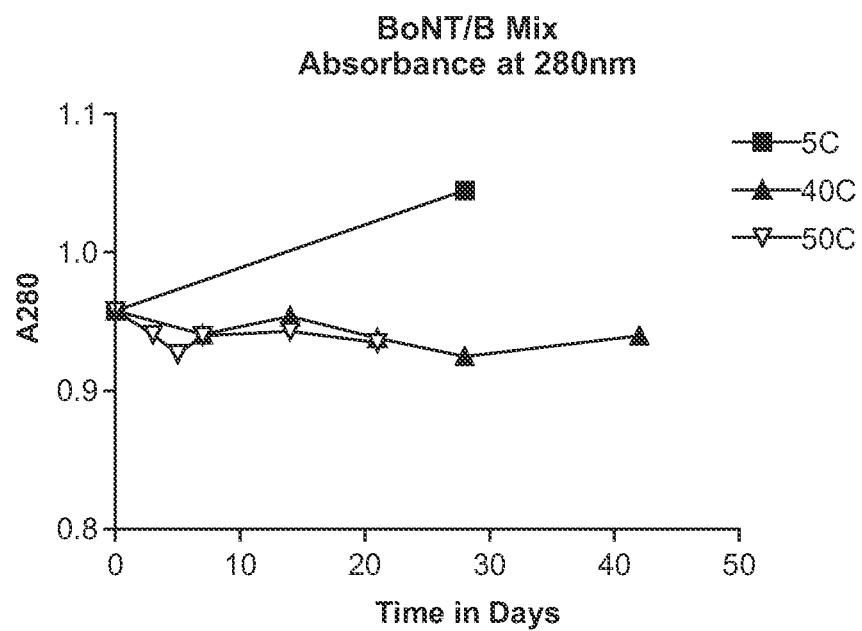
FIG. 22 shows A280 protein concentration measurements of BoNT/B ABT10/ABT14/ABT17 mixture stored through six weeks at 5, 40 and 50° C.
Figures 23, 24:
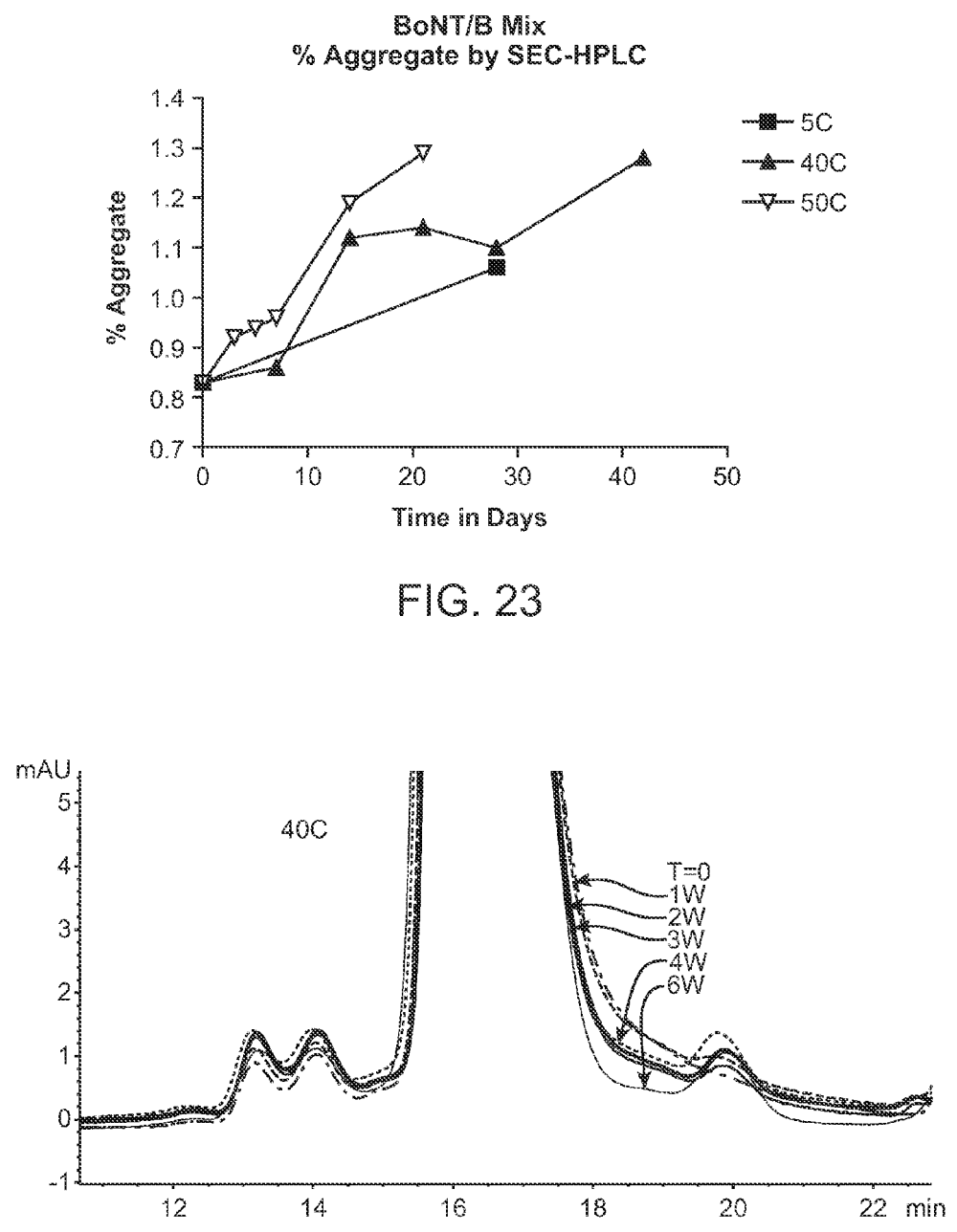

With respect to chemical stability, solutions appeared clear and colorless, only the 2-8° C. T=4 W sample had an increase in A350 light scattering and interference with the A280 read (FIGS. 21 and 22). Accelerated samples showed no measurable losses in total protein by A280 or SEC total peak area and no A350 increases, so this outlier is not a concern. The mixture showed increases in aggregate (FIGS. 23 and 24) and truncated species (FIG. 25) by SEC-HPLC on accelerated stability. The aggregate increased 0.5% after 6 weeks at 40° C., so aggregation is not considered significant. The individual mAb's separated by CEX-HPLC showed typical degradation patterns with shifts from basic and main peaks to more acidic forms (FIG. 26). Overall, the antibody mixture showed excellent chemical stability.

The anti-BoNT/B antibody mixture was slightly sensitive to agitation stress, and additional of polysorbate 80 alleviated most of the negative effects. When discernible by assay, each antibody was shown to behave similarly to patterns seen during individual mAb storage. The antibody mixture was stable to freeze thaw stress. The mixture was also shown to be stable through four weeks at 2-8° C. for short term use in clinic or laboratory settings.

In summary, the three anti-BoNT/B antibody mixture (ABT10/14/17) showed high physical and chemical stability when formulated in 10 mM NaSuccinate/Succinic acid, 142 mM L-arginine at pH 6.0 at 1 mg/ml total protein at a 1:1:1 ratio.

Other Examples for Anti-BoNT/B Antibody Mixtures

Various anti-BoNT/B antibody mixtures, as shown in Table 14, have been stored in the target formulation of 10 mM NaSuccinate/Succinic acid, 142 mM L-arginine at pH 6.0 at 1 mg/ml total protein (1:1:1 ratio) at 2-8° C. and periodically tested by SEC-HPLC for stability evaluation. No increases in aggregate or truncated species have been detected, and no significant losses in total protein have been detected. Table 14 shows the data for T=0 vs. four weeks for each of the five mixes.

TABLE 14

Mix Stability data summary at four weeks storage at 2-8° C.

| Co-formulation | % Aggregate | | % Truncated | | % Remaining of T = 0 |
|---|---|---|---|---|---|
| | T = 0 | 4 W | T = 0 | 4 W | 2-8° C. at T = 4 W |
| ABT12/14/10/11 | 3.89 | 3.46 | 0.48 | 0.34 | 98 |
| ABT12/14/10/07 | 2.70 | 2.65 | 0.55 | 0.32 | 98 |
| ABT12/14/07/11 | 4.07 | 3.66 | 0.25 | 0.07 | 99 |

TABLE 14-continued

Mix Stability data summary at four weeks storage at 2-8° C.

| Co-formulation | % Aggregate T = 0 | % Aggregate 4 W | % Truncated T = 0 | % Truncated 4 W | % Remaining of T = 0 2-8° C. at T = 4 W |
|---|---|---|---|---|---|
| ABT12/07/10/11 | 4.59 | 3.92 | 0.56 | 0.27 | 98 |
| ABT07/14/10/11 | 2.67 | 2.28 | 0.69 | 0.33 | 103 |

The stability screen showed that none of the antibodies formulated in the target formulation were showing any strong tendency toward degradation. Although slight differences in thermal, physical and chemical stability are being revealed, none of the antibodies are showing aggregation, truncation or protein losses at such a level as to cause concern or significantly differentiate one from the others.

Similar tests can be done for the lead candidate antibody mixtures which can include ABT10/ABT14/ABT11, ABT10/ABT14/ABT17 in 10 mM sodium succinate/succinic acid, 142 mM L-arginine, 0.005% Tween-80 at pH 6.0. The coformulation can be stored at 2-8° C. All of these formulations are physically and chemically stable.

Example 7

Individual Formulation and Co-Formulation Development for Anti-BoNT/E Antibodies
1. Stability of Individually Formulated Anti-BoNT/E Antibodies This study assesses the solubility, physical (agitation and freeze/thaw) stability and chemical stability of each of the BoNT/E mAbs (listed below with protein concentrations). Each mAb was assessed in the target formulation of 10 mM NaSuccinate, 142 mM L-arginine at pH 6.0. Studies were performed in the absence of surfactant (polysorbate 80).

ABT21: 1.50 cm$^{-1}$[g/L]$^{-1}$
ABT18: 1.43 cm$^{-1}$[g/L]$^{-1}$
ABT19: 1.43 cm$^{-1}$[g/L]$^{-1}$

The three BoNT/E antibodies assessed had typical DSC thermal stability profiles and easily attained the minimum solubility requirement of 10 mg/ml. ABT21 tailed by the current method by SEC but it did not aggregate even at stressed temperature. The charge profile appeared normal at time zero, but degradation shifted both to the acidic and basic peaks for samples stored at accelerated temperature.

ABT18 and ABT19 exhibited a normal sizing profile by SEC-HPLC and no apparent stability problem. The IEX-HPLC method separated the main peak of ABT19 from ABT14 and ABT03 with significant overlap of acidic and basic species. The method gradient was changed slightly to separate the main peak of ABT18 from ABT02 and ABT17.
2. Stability of Transient BoNT/E 3-mAb Mixes:

This study assessed stability for the anti-BoNT/E antibody mixtures. The study included physical (freeze/thaw and agitation) and chemical stability through 6 weeks at 40° C. and three weeks at 50° C. The mixture included BoNT/E antibodies ABT18, ABT19 and ABT21. Each transiently expressed antibody has shown its own individual sensitivity to both physical and chemical stress, and this study helped assess temporary storage and shipping conditions as well as short term chemical stability for the mixes during use. The antibodies were formulated in the target formulation of 10 mM NaSuccinate/Succinic acid, 142 mM L-arginine at pH 6.0 at 1 mg/ml total protein (1:1:1 ratio).

Analytical methods included the following:
Visual: Observes visual changes in solution against a black/white background
UV absorbance at 280 nm: Measures total protein in solution
A350: Measures the presence of large particles that scatter light
SEC-HPLC: Measures size-based degradation (aggregation and truncation)
CEX-HPLC: Measures charge-based degradation (formation of acidic species).

Chemical stability was assessed at 40° C. through 6 weeks and 50° C. through three weeks. A 5° C. sample was pulled at four weeks. The physical stability study included agitation (1000 orbital shaking for 72 hours) and freeze/thaw (to −70° C. through 5 cycles).

Figures 27, 28:
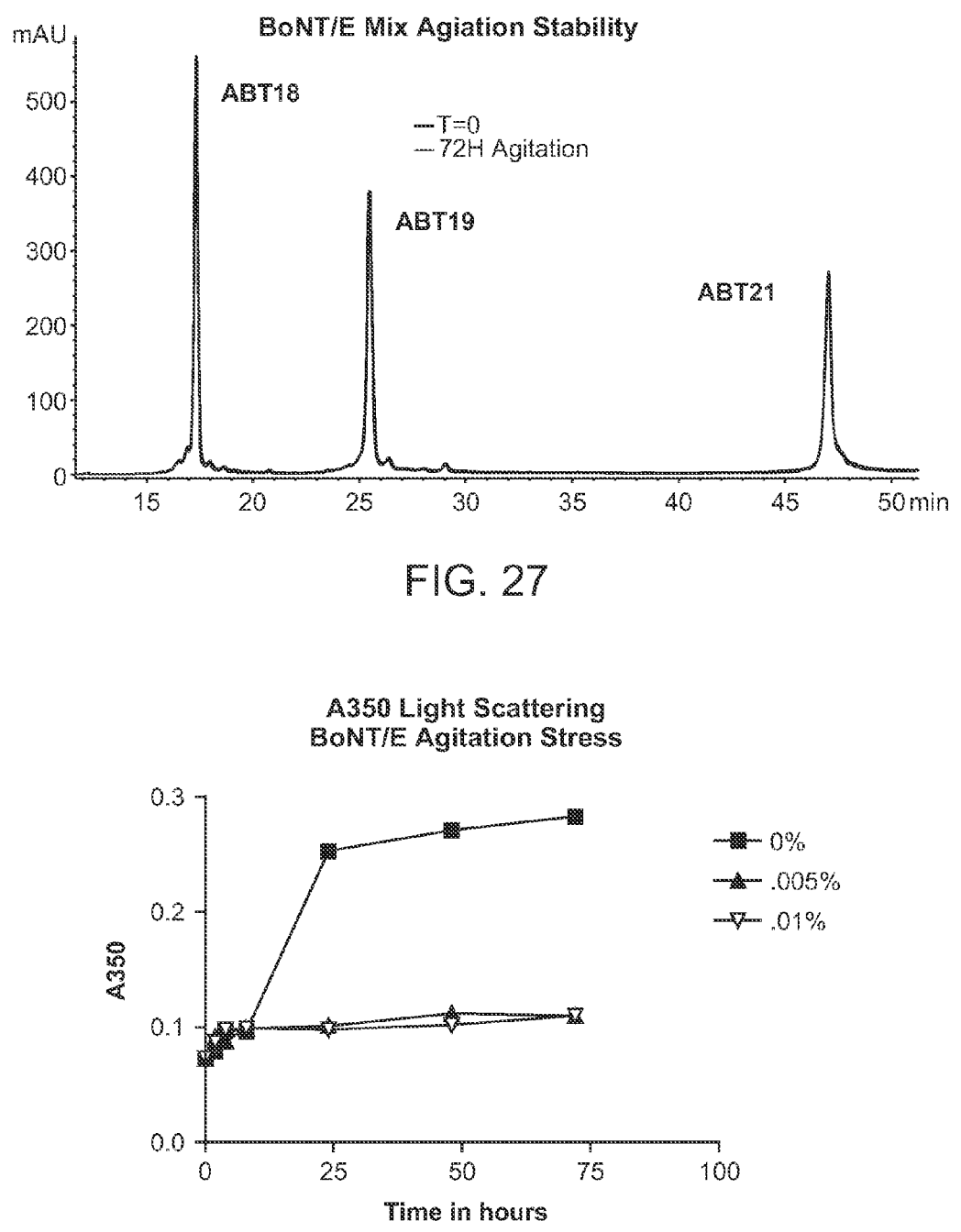

The BoNT/E Mix study was performed without surfactant for the chemical and freeze/thaw arms, but with two additional formulations containing 0.005% and 0.01% polysorbate 80 for the agitation arm in view of the agitation sensitivity with ABT18 and ABT21. ABT18 and ABT21 showed similar losses to previous individual mAb stability studies as measured by peak area on CEX-HPLC. ABT19 did not show a loss in total protein by this measurement (FIG. 27). Addition of surfactant at either 0.005% or 0.01% alleviated this effect, thus polysorbate 80 can be used as physical stabilizer for the BoNT/E mix.

A350 increases and visual changes were observed. The surfactant-free sample became more opalescent as shaking time increased, and A350's increased. Addition of surfactant reduced the A350 increases (FIG. 28). The SEC total peak area measurements showed variation (most likely due to light scattering increases) and a loss in total protein for the surfactant free sample (FIG. 29). A280 measurements had similar variation. The agitation—dependent aggregation did not appear to be forming soluble aggregates, as no increase in percent HMW by SEC-HPLC is apparent (FIG. 30).

None of the individual transient BoNT/E antibodies showed significant change on freeze/thaw stress. Similarly, there were no losses in total protein, no increases in A350 light scattering and no increase in percent aggregate measured by SEC-HPLC. Table 15 summarizes the freeze/thaw data for the BoNT/E mix study.

TABLE 15

Summary of Freeze/thaw stress data for BoNT/E mix study.

| mAb | Assay | Freeze/thaw cycles 0 | 1 | 3 | 5 |
|---|---|---|---|---|---|
| Mix | Visual | CC | CC | CC | CC |
| Mix | A350 | 0.073 | 0.056 | 0.053 | 0.057 |
| Mix | % total protein by SEC-HPLC TPA | 100 | 99 | 99 | 99 |
| ABT18 | % of T0 by CEX - ABT18 peak area | 100 | 99 | 98 | 98 |
| ABT19 | % of T0 by CEX - ABT19 peak area | 100 | 100 | 100 | 99 |
| ABT21 | % of T0 by CEX - ABT21 peak area | 100 | 104 | 94 | 97 |
| Mix | % Aggregate | 0.78 | 0.87 | 0.86 | 0.82 |
| Mix | % Clip | 0 | 0 | 0 | 0 |

Figure 33:
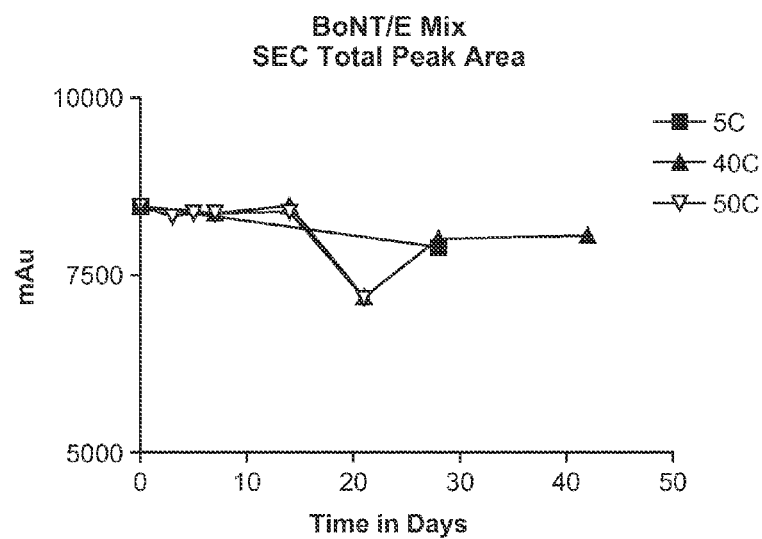
FIG. 33 shows SEC-HPLC total peak area measurements in milli-absorbance units (mAU's) showing insignificant drops in total protein at 5° C., 40° C. and 50° C.
Figure 34:
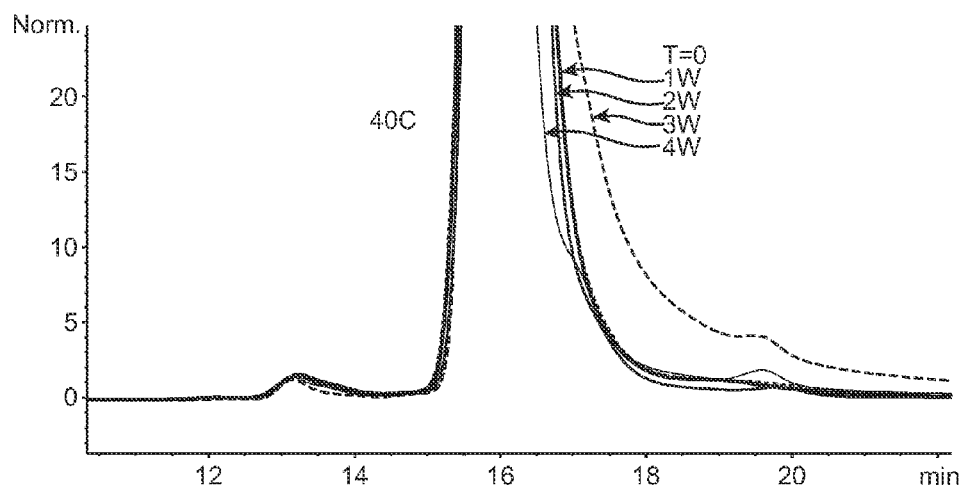
FIG. 34 shows SEC-HPLC chromatographic overlay of BoNT/E ABT18/ABT19/ABT21 mixture stored through four weeks at 40° C. T=3 W reflects loss of column resolution, and T=4 W reflects resolution using replacement column.

The A350 and A280 measurements for accelerated stability samples both dropped from the T=0 measurement (FIGS. 31 and 32). As no drop in total peak area by SEC (FIG. 33) or CEX was noted, this effect was believed to be due to assay variation. The mixture showed no increase in aggregate (FIG.

Figures 35, 36:
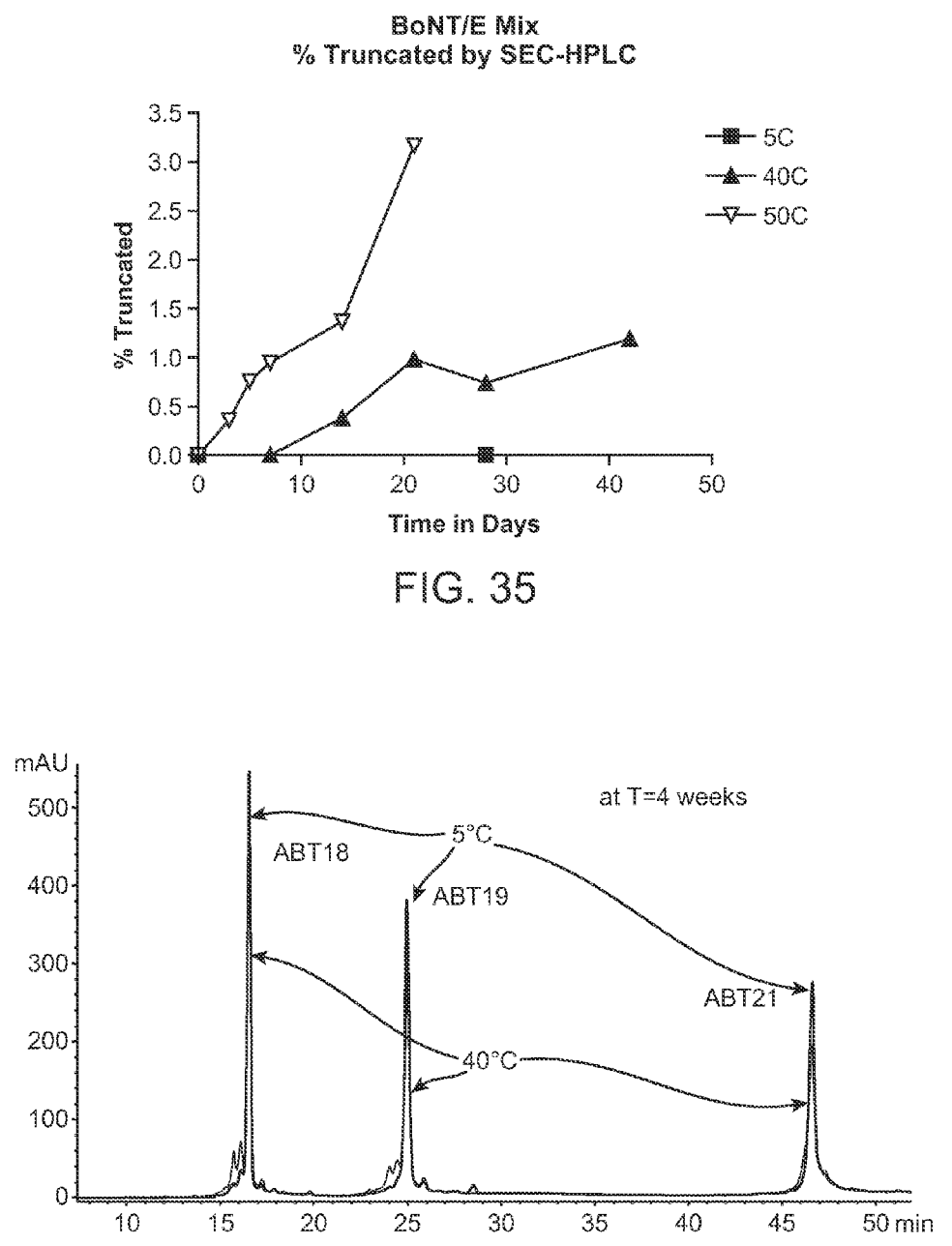
Figure 37:
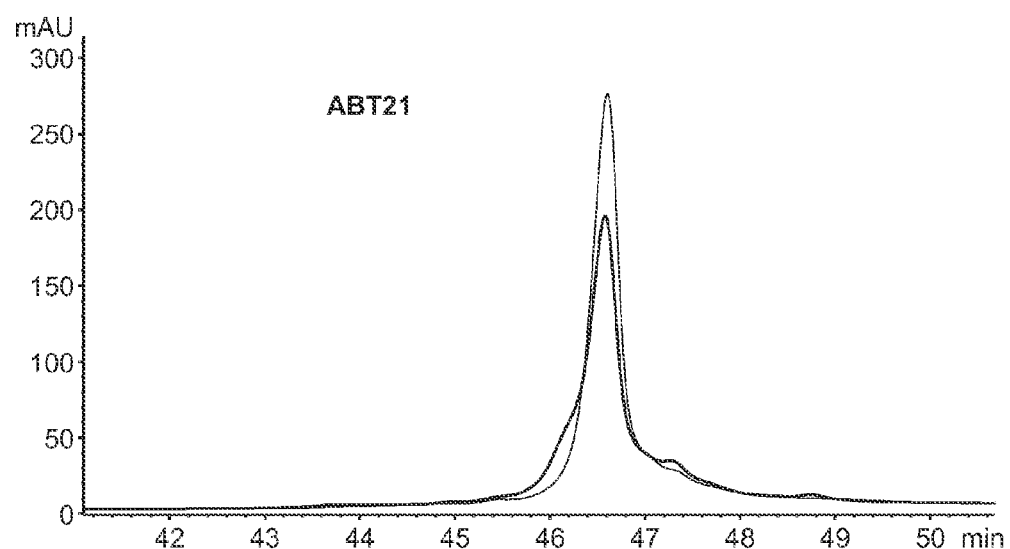
FIG. 37 is a magnified image showing chromatographic overlay of ABT21 separated by CEX-HPLC of 5° C. vs. 40° C. at the four week time point.

34). The relatively high rate of truncation was most likely due to ABT21's sensitivity to clipping; but at a total increase of 1% over six weeks at 40° C., this rate of change is still well within acceptable limits (FIG. 35). ABT18 and ABT19 separated by CEX-HPLC showed typical degradation patterns with shifts from basic and main peaks to more acidic forms (FIG. 36), while ABT21 shifts from main to both more acidic and basic regions (FIG. 37).

The anti-BoNT/E antibody mixture was slightly sensitive to agitation stress, and addition of polysorbate 80 alleviated most of the negative effects. When discernible by assay, each antibody was shown to behave similarly to patterns seen during individual mAb storage; for example, ABT21 shows the same charge-based change as observed in the initial individual mAb study. The antibody mixture was stable to freeze thaw stress and thus freezing is the preferred option for longer term storage and shipping. The mixture was also shown to be stable through four weeks at 2-8° C. for short term use in clinic or laboratory settings.

In summary, the three anti-BoNT/E antibody mixture (ABT18/19/21) showed high physical and chemical stability when formulated in 10 mM NaSuccinate/Succinic acid, 142 mM L-arginine at pH 6.0 at 1 mg/ml total protein at a 1:1:1 ratio. In addition, the physical stability of the three anti-BoNT/E antibody mixture (ABT18/19/21) was enhanced by addition of polysorbate 80.

Other Examples for Anti-BoNT/E Antibody Mixtures

Similar tests can be done for the lead candidate antibody mixtures which can include ABT21/ABT20/ABT18, ABT21/ABT20/ABT19 and ABT21/ABT19/ABT18 in 10 mM sodium succinate/succinic acid, 142 mM L-arginine, 0.005% Tween-80 at pH 6.0. The coformulation can be stored at 2-8° C. All of these formulations are physically and chemically stable.

Co Formulations with Antibodies Against More than One Serotype of BoNT

Stable formulations can also be prepared with mixtures of antibodies against different serotypes of BoNT. For example, a stable formulation can be prepared with three anti-BoNT/A antibodies and three anti-BoNT/B antibodies, or alternatively three anti-BoNT/B antibodies and three anti-BoNT/E antibodies, or alternatively three anti-BoNT/A antibodies and three anti-BoNT/E antibodies. In another example, a stable formulation can be prepared with three anti-BoNT/A antibodies, three anti-BoNT/B antibodies and three anti-BoNT/E antibodies.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

The invention claimed is:

1. A stable pharmaceutical formulation comprising a plurality of antibodies directed to at least one serotype of botulinum neurotoxin (BoNT) each of which antibodies specifically recognizes and binds a different epitope or a different BoNT serotype and is present at a concentration of at least about 1 mg/mL, an effective amount of a succinate buffer in a concentration from about 5 mM to about 15 mM, and an effective amount of arginine in a concentration of from about 140 mM to about 144 mM, wherein the pH of the formulation is between about 5 and about 6.5, wherein the formulation is stable at room temperature for at least 30 days, and wherein the plurality of antibodies comprises a first antibody comprising a heavy chain variable region of SEQ ID NO.3 and a light chain variable region of SEQ ID NO.4, a second antibody comprising a heavy chain variable region of SEQ ID NO.1 and a light chain variable region of SEQ ID NO.2, and a third antibody comprising a heavy chain variable region of SEQ ID NO.5 and a light chain variable region of SEQ ID NO.6.

2. The formulation of claim 1, wherein each antibody is present at a concentration between about 1 mg/mL and about 5 mg/mL.

3. The formulation of claim 1, wherein the pH is at about 6.

4. The formulation of claim 1, wherein the pH is at about 6.5.

5. The formulation of claim 1, wherein the succinate buffer comprises sodium succinate.

6. The formulation of claim 1, wherein the arginine is present in a concentration of about 142 mM.

7. The formulation of claim 1, further comprising a surfactant.

8. The formulation of claim 7, wherein the surfactant comprises at least one selected from the group consisting of polyoxyethylensorbitan fatty acid ester, polyoxyethylene alkyl ether, alkylphenylpolyoxyethylene ether, polyoxyethylene polyoxypropylene copolymer, and sodium dodecyl sulphate.

9. The formulation of claim 8, wherein the surfactant is polyoxyethylensorbitan fatty acid ester.

10. The formulation of claim 9, wherein the polyoxyethylensorbitan fatty acid ester is polysorbate 20 or polysorbate 80.

11. The formulation of claim 9, wherein the polyoxyethylensorbitan fatty acid ester is polysorbate 80.

12. The formulation of claim 7, wherein the surfactant is present in a concentration of from about 0.002% (w/v) to about 0.1% (w/v).

13. The formulation of claim 7, wherein the surfactant is present in a concentration of from about 0.003% (w/v) to about 0.007% (w/v).

14. The formulation of claim 1, further comprising a stabilizer and/or a cryoprotectant and/or a lyoprotectant.

15. The formulation of claim 14, wherein the stabilizer comprises at least one selected from the group consisting of a sugar, an amino acid, a polyol, a surfactant, an antioxidant, a preservative, a cyclodextrine, a polyethyleneglycol, albumin and a salt.

16. The formulation of claim 1, wherein the formulation is stable at a temperature from about 2.0° C. to about 8.0° C. for at least about five years.

17. The formulation of claim 1, wherein the formulation is stable at a temperature from about −80° C. to about −20° C. for at least about two years.

18. The formulation of claim 1, wherein the formulation is physically stable.

19. The formulation of claim 1, wherein the formulation is chemically stable.

20. The formulation of claim 1, wherein the formulation is biologically stable.

21. A lyophilized formulation prepared by lyophilizing the formulation of claim 1.

* * * * *

SEQUENCE LISTING

```
<160> NUMBER OF SEQ ID NOS: 36

<210> SEQ ID NO 1
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Gly Gly Val Val His Pro Gly Arg
1               5                   10                  15

Ser Leu Lys Leu Ser Cys Ala Gly Ser Gly Phe Thr Phe Ser Asp Tyr
            20                  25                  30
```

```
Asp Met His Trp Val Arg Gln Ala Pro Gly Lys Gly Leu Glu Trp Val
         35                  40                  45

Ala Val Met Trp Phe Asp Gly Thr Glu Lys Tyr Ser Ala Glu Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Asp Thr Ala Val Tyr Tyr Cys
             85                  90                  95

Ala Arg Glu Pro Asp Trp Leu Leu Trp Gly Asp Arg Gly Ala Leu Asp
            100                 105                 110

Val Trp Gly Gln Gly Thr Thr Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Met Thr Gln Ser Pro Ser Thr Leu Ser Ala Ser Val Gly
 1               5                  10                  15

Asp Arg Val Thr Ile Thr Cys Trp Ala Ser Gln Ser Ile Ser Ser Arg
             20                  25                  30

Leu Ala Trp Tyr Gln Gln Lys Pro Gly Lys Ala Pro Lys Leu Leu Met
         35                  40                  45

Tyr Glu Ala Thr Ser Leu Gly Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Ala Tyr Tyr Cys Gln His Tyr Asp Thr Tyr Pro Tyr
             85                  90                  95

Thr Phe Gly Gln Gly Thr Lys Leu Glu Ile Lys
            100                 105

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Gln Ser Gly Gly Gly Leu Val Gln Pro Gly Gly
 1               5                  10                  15

Ser Leu Arg Leu Ser Cys Ala Ala Ser Gly Phe Thr Phe Lys Tyr Asp
             20                  25                  30

Tyr Met Tyr Trp Ile Arg Gln Ala Pro Gly Lys Gly Leu Glu Trp Val
         35                  40                  45

Ala Thr Ile Ser Asp Gly Gly Ser Tyr Thr Tyr Tyr Ser Asp Ser Val
 50                  55                  60

Glu Gly Arg Phe Thr Thr Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
             85                  90                  95
```

-continued

Ser Arg Tyr Arg Tyr Asp Asp Ala Met Asp Tyr Trp Gly Gln Gly Thr
            100                 105                 110

Leu Val Thr Val Ser Ser
        115

<210> SEQ ID NO 4
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Ile Val Leu Thr Gln Ser Pro Ala Thr Leu Ser Leu Ser Pro Gly
1               5                   10                  15

Glu Arg Ala Thr Ile Ser Cys Arg Ala Ser Glu Ser Val Asp Ser Tyr
            20                  25                  30

Gly His Ser Phe Met Gln Trp Tyr Gln Gln Lys Pro Gly Gln Ala Pro
        35                  40                  45

Arg Leu Leu Ile Tyr Arg Ala Ser Asn Leu Glu Pro Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Gly Asn
                85                  90                  95

Glu Val Pro Phe Thr Phe Gly Gln Gly Thr Lys Val Glu Ile Lys
            100                 105                 110

<210> SEQ ID NO 5
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Ser Ile Ser Val Gly Gly Ser Asp Thr Tyr Tyr Ala Asp Ser Val
    50                  55                  60

Lys Gly Arg Phe Thr Val Ser Arg Asp Asn Ser Lys Asn Thr Leu Leu
65                  70                  75                  80

Leu Gln Met Asn Ser Leu Arg Ala Glu Asp Thr Ala Val Tyr Tyr Cys
                85                  90                  95

Ala Lys Val Arg Thr Lys Tyr Cys Ser Ser Leu Ser Cys Phe Ala Gly
            100                 105                 110

Phe Asp Ser Trp Gly Gln Gly Thr Arg Val Thr Val Ser Ser
        115                 120                 125

<210> SEQ ID NO 6
<211> LENGTH: 108
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 6

Asp Val Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu His Trp Tyr Gln Gln Lys Pro Gly Lys Ala Pro Thr Leu Leu Ile
        35                  40                  45

Ser Asp Ala Ser Ser Gln Ser Gly Val Pro Ser Arg Phe Ser Gly
50                  55                  60

Ser Arg Phe Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Arg Ala
                85                  90                  95

Leu Thr Phe Gly Gly Gly Thr Lys Val Glu Ile Lys
            100                 105

<210> SEQ ID NO 7
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Glu
1               5                   10                  15

Ser Leu Val Ile Ser Cys Lys Ala Ser Gly Asp Lys Asp Thr Phe Thr
            20                  25                  30

Ser Phe Trp Ile Ala Trp Val Arg Gln Met Pro Gly Lys Gly Leu Glu
        35                  40                  45

Trp Met Gly Ile Ile Tyr Ala Gly Asp Ser Asp Thr Arg Tyr Ser Pro
    50                  55                  60

Ser Phe Gln Gly His Val Asn Ile Ser Val Asp Arg Ser Thr Asn Thr
65                  70                  75                  80

Ala Tyr Leu Gln Trp Ser Ser Leu Lys Ala Ser Asp Thr Ala Met Tyr
                85                  90                  95

Tyr Cys Ala Arg His Asp Ser Arg Tyr Lys Tyr Phe Tyr Phe Gly Met
            100                 105                 110

Asp Val Trp Gly Gln Gly Thr Thr Val Thr Val Ser Ser
        115                 120                 125

<210> SEQ ID NO 8
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Gln Ser Gly Ala Glu Val Lys Lys Pro Gly Glu
1               5                   10                  15

Ser Leu Lys Ile Ser Cys Lys Ala Ser Gly Asp Lys Asp Thr Phe Thr
            20                  25                  30
```

```
Ser Phe Trp Ile Ala Trp Val Arg Gln Met Pro Gly Lys Gly Leu Glu
            35                  40                  45

Trp Met Gly Ile Ile Tyr Ala Gly Asp Ser Asp Thr Arg Tyr Ser Pro
 50                      55                  60

Ser Phe Gln Gly His Val Asn Ile Ser Val Asp Arg Ser Thr Asn Thr
 65                  70                  75                  80

Ala Tyr Leu Gln Trp Ser Ser Leu Lys Ala Ser Asp Thr Ala Met Tyr
                    85                  90                  95

Tyr Cys Ala Arg His Asp Ser Arg Tyr Lys Tyr Phe Tyr Phe Gly Met
                100                 105                 110

Asp Val Trp Gly Gln Gly Thr Thr Val Thr Val Ser Ser
            115                 120                 125
```

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Glu Pro Gly Lys Ala Pro Lys Leu Leu Ile
            35                  40                  45

Tyr Ser Ala Ser Ser Leu Gln Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                    85                  90                  95

Tyr Thr Phe Gly Gln Gly Thr Lys Leu Glu Ile Lys
                100                 105
```

<210> SEQ ID NO 10
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gln Val Gln Leu Leu Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95
```

Ala Arg Gly Tyr Ser Asn Tyr Asp Tyr Tyr Gly Met Asp Val Trp
            100                 105                 110

Gly Gln Gly Thr Thr Val Thr Val Ser Ser
        115                 120

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Glu Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Pro Pro Leu
                85                  90                  95

Thr Phe Gly Gly Gly Thr Lys Val Asp Ile Lys
            100                 105

<210> SEQ ID NO 12
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser His Tyr
            20                  25                  30

Gly Met His Trp Val Arg Gln Ser Pro Gly Lys Gly Leu Glu Trp Val
        35                  40                  45

Ala Val Ile Trp Tyr Asp Gly Arg Asn Pro Tyr Tyr Ala Ala Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Leu Thr Arg Phe His Asp Thr Thr Phe Gly Val Phe Glu
            100                 105                 110

Met Trp Gly Pro Gly Thr Thr Val Thr Val Ser Ser
        115                 120

<210> SEQ ID NO 13
<211> LENGTH: 106
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 13

Glu Ile Val Leu Thr Gln Ser Pro Ser Phe Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Leu Tyr Thr
                85                  90                  95

Phe Gly Gln Gly Thr Lys Val Asp Ile Lys
            100                 105

<210> SEQ ID NO 14
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Ile Phe Arg Thr Tyr
            20                  25                  30

Gly Met His Trp Val Arg Gln Ala Pro Gly Lys Gly Leu Glu Trp Val
        35                  40                  45

Ala Phe Val Ser Ser Asp Gly Asn Asn Lys Phe Tyr Ser Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Glu Thr Glu Asp Thr Ala Met Tyr Tyr Cys
                85                  90                  95

Ala Lys Asp Arg Tyr Pro Ile Asp Cys Ser Gly Ser Cys Phe Ser
            100                 105                 110

Tyr Gly Met Asp Val Trp Gly Gln Gly Thr Thr Val Thr Val Ser Ser
        115                 120                 125

<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Lys Phe
            20                  25                  30
```

```
Leu Ala Trp Tyr Gln Gln Lys Arg Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Ala Leu Thr Ile Ser Ser Leu Gln Ser
65              70                  75                  80

Glu Asp Phe Ala Asp Tyr Tyr Cys Gln Gln Tyr Asp Asn Trp Pro Ile
                85                  90                  95

Thr Phe Gly Gln Gly Thr Arg Leu Glu Ile Lys
            100                 105

<210> SEQ ID NO 16
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Leu His Trp Val Arg Gln Thr Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ser His Tyr Gly Asp Tyr Val Gly Tyr Leu Asp Tyr
            100                 105                 110

Trp Gly Gln Gly Thr Leu Val Thr Val Ser Ser
        115                 120

<210> SEQ ID NO 17
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser Tyr Val Leu Thr Gln Pro Pro Ser Val Ser Val Ala Pro Gly Lys
1               5                   10                  15

Thr Ala Arg Ile Thr Cys Glu Gly Asn Asn Val Gly Asn Lys Asn Val
            20                  25                  30

His Trp Tyr Gln Gln Arg Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Asn Arg Val Glu Ala Gly
65                  70                  75                  80
```

```
Asp Glu Ala Asp Tyr Tyr Cys Gln Val Trp Asp Ser Ser Ala Gln
                85                  90                  95

Trp Val Phe Gly Gly Gly Thr Lys Leu Thr Val Leu Gly
            100                 105

<210> SEQ ID NO 18
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Leu His Trp Val Arg Gln Thr Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ser His Tyr Gly Asp Tyr Val Gly Tyr Leu Asp Tyr
            100                 105                 110

Trp Gly Gln Gly Thr Leu Val Thr Val Ser Ser
        115                 120

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Ala Phe Gly Gln Gly Thr Lys Leu Glu Ile Lys
            100                 105

<210> SEQ ID NO 20
<211> LENGTH: 121
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 20

Gln Val Gln Leu Val Gln Ser Gly Gly Gly Leu Val Gln Pro Gly Gly
1               5                   10                  15

Ser Arg Arg Leu Ser Cys Ala Ala Ser Gly Phe Tyr Phe Asn Ala Tyr
            20                  25                  30

Trp Met Thr Trp Val Arg Gln Ala Pro Gly Lys Gly Leu Glu Trp Val
        35                  40                  45

Ala Asn Ile Asn Leu Asp Gly Thr Glu Ile Tyr Tyr Leu Asp Ser Val
    50                  55                  60

Lys Gly Arg Phe Thr Val Ser Arg Asp Asn Val Lys Asn Ser Val Phe
65                  70                  75                  80

Leu Gln Met Ser Ser Leu Arg Val Glu Asp Thr Ala Val Tyr Phe Cys
                85                  90                  95

Ala Arg Leu Glu Trp Gly Gly Arg Asn Gly Trp Val Pro Trp Gly
            100                 105                 110

Gln Gly Thr Leu Val Thr Val Ser Ser
        115                 120

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Met Thr Gln Ser Pro Ser Ser Leu Ser Ala Ser Val Gly
1               5                   10                  15

Asp Arg Val Ser Ile Ser Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Lys Thr Ser Ser Leu Glu Ser Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Ala Glu Val Lys Lys Pro Gly Ala
1               5                   10                  15

Ser Val Asn Val Ser Cys Lys Ala Ser Gly Tyr Thr Phe Thr Gly Tyr
            20                  25                  30
```

Tyr Ile Tyr Trp Val Arg Gln Ala Pro Gly Gln Gly Leu Glu Trp Met
            35                  40                  45

Gly Trp Ile Asn Pro Asn Ser Gly Val Thr Lys Tyr Ala Gln Lys Phe
 50                  55                  60

Gln Gly Arg Val Thr Met Thr Ile Asp Thr Ser Thr Asn Thr Ala Tyr
 65                  70                  75                  80

Met Glu Leu Asn Arg Leu Arg Ala Asp Asp Thr Ala Val Tyr Tyr Cys
                 85                  90                  95

Ala Arg Glu Trp Thr Gln Leu Trp Ser Pro Tyr Asp Tyr Trp Gly Gln
             100                 105                 110

Gly Thr Thr Val Thr Val Ser Ser
         115                 120

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Val Leu Thr Gln Ser Pro Ser Thr Leu Ser Ala Ser Val Gly
 1               5                  10                  15

Asp Arg Val Thr Ile Ser Cys Arg Ala Ser Arg Ser Ile Gly Trp Tyr
                 20                  25                  30

Leu Asn Trp Tyr Gln Gln Arg Pro Gly Lys Ala Pro Lys Leu Leu Ile
             35                  40                  45

Tyr Ala Ala Ser Ser Leu His Asn Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Ala Phe Gly Phe Pro Arg
                 85                  90                  95

Thr Phe Gly Gln Gly Thr Lys Val Glu Ile Lys
             100                 105

<210> SEQ ID NO 24
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Gln Glu Ser Gly Ser Arg Leu Val Lys Pro Ser Gln
 1               5                  10                  15

Thr Leu Ser Leu Thr Cys Gly Val Ser Gly Gly Ser Ile Ser Ser Ser
                 20                  25                  30

Ser Tyr Ser Trp Ser Trp Ile Arg Gln Thr Pro Gly Lys Gly Leu Glu
             35                  40                  45

Trp Ile Gly Tyr Ile Tyr His Ser Gly Ser Thr Tyr Tyr Asn Pro Ser
 50                  55                  60

Leu Lys Ser Arg Val Thr Met Ser Val Asp Lys Ser Arg Asn Gln Phe
 65                  70                  75                  80

Ser Leu Asn Met Ser Ser Val Thr Ala Ala Asp Thr Ala Val Tyr Tyr
                 85                  90                  95

Cys Ala Arg Thr Ala Phe Tyr Tyr Glu Asn Thr Gly Pro Ile Arg Cys
                100                 105                 110

Tyr Leu Asp Phe Trp Gly Gln Gly Thr Leu Val Thr Val Ser Ser
            115                 120                 125

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Met Thr Gln Ser Pro Ser Thr Leu Ser Ala Ser Ile Gly
1               5                   10                  15

Asp Arg Val Thr Ile Ser Cys Arg Ala Ser Gln Ser Ile Gln Ser Trp
            20                  25                  30

Leu Ala Trp Tyr Gln Gln Arg Pro Gly Glu Ala Pro Lys Leu Leu Ile
        35                  40                  45

Tyr Ser Ala Ser Thr Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gln Gly Thr Lys Leu Glu Ile Lys
            100                 105

<210> SEQ ID NO 26
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Ser Trp Val Arg Gln Ala Pro Gly Lys Gly Leu Ala Trp Val
        35                  40                  45

Ser Ser Leu Thr Ala Ser Gly Asp Asn Thr Phe Tyr Ala Asp Ser Val
    50                  55                  60

Lys Gly Arg Phe Thr Ile Ser Arg Asp Asn Ser Asn Asn Thr Leu Tyr
65                  70                  75                  80

Leu Gln Met His Ser Leu Arg Ala Glu Asp Thr Ala Val Tyr Tyr Cys
                85                  90                  95

Ala Lys Ala Leu Val Gly Arg Tyr Asp Ile Ser Thr Gly Tyr Tyr Arg
            100                 105                 110

Pro Val Met Asp Ser Trp Gly Gln Gly Thr Leu Val Thr Val Ser Ser
        115                 120                 125

<210> SEQ ID NO 27
<211> LENGTH: 107
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Leu Ser Ala Ser Val Gly
1               5                   10                  15

Asp Arg Val Thr Ile Thr Cys Arg Thr Ser Gln Gly Phe Thr Ser Ala
            20                  25                  30

Leu Ala Trp Tyr Gln Gln Lys Pro Gly Glu Pro Pro Lys Leu Leu Ile
        35                  40                  45

Tyr Asp Ala Ser Lys Leu Glu Ser Gly Val Pro Ser Arg Phe Ser Gly
    50                  55                  60

Ser Gly Ser Gly Thr Asn Phe Ala Leu Thr Ile Ser Ser Leu Gln Pro
65                  70                  75                  80

Glu Asp Phe Ala Thr Tyr Phe Cys Gln Gln Ser Asn Ser Tyr Pro Leu
                85                  90                  95

Thr Phe Gly Gly Gly Thr Lys Val Glu Ile Lys
            100                 105

<210> SEQ ID NO 28
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Gln Glu Ser Gly Ala Glu Val Lys Lys Pro Gly Ser
1               5                   10                  15

Ser Val Lys Val Ser Cys Lys Ala Ser Gly Gly Asp Leu Asn Lys Tyr
            20                  25                  30

Ala Ile Thr Trp Leu Arg Gln Ala Pro Gly Gln Gly Phe Glu Trp Met
        35                  40                  45

Gly Gly Ile Thr Pro Ile Phe Ala Thr Thr Asn Tyr Ala Gln Lys Phe
    50                  55                  60

Gln Gly Arg Val Thr Ile Thr Ala Asp Glu Ser Thr Ser Thr Val Tyr
65                  70                  75                  80

Met Asp Leu Ser Ser Leu Gly Ser Glu Asp Thr Ala Ile Tyr Phe Cys
                85                  90                  95

Ala Lys Ser Pro Arg Gly Ile Val Gly Thr Phe Asp Thr Trp Gly
            100                 105                 110

Gln Gly Thr Met Val Thr Val Ser Ser
        115                 120

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Ile Val Leu Thr Gln Ser Pro Ser Phe Leu Ser Ala Phe Val Gly
1               5                   10                  15

Asp Arg Val Thr Ile Thr Cys Arg Thr Ser Gln Ser Ile Asn Asn Tyr
            20                  25                  30
```

Leu Asn Trp Tyr Gln Gln Lys Ala Gly Lys Ala Pro Lys Leu Leu Ile
            35                  40                  45

Tyr Ala Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Leu
                85                  90                  95

Thr Phe Gly Gly Gly Thr Lys Val Glu Ile Lys
            100                 105

<210> SEQ ID NO 30
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Val Gln Ser Gly Gly Gly Val Val Gln Pro Gly Lys
1               5                   10                  15

Ser Leu Arg Leu Ser Cys Ala Ala Ser Gly Phe Ala Phe Gly Gly Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Phe Tyr Cys
                85                  90                  95

Ala Arg Ala Arg Leu Cys Thr Ser Thr Ser Cys Tyr Trp Thr Phe Asp
            100                 105                 110

Pro Trp Gly Gln Gly Thr Leu Val Thr Val Ser Ser
        115                 120

<210> SEQ ID NO 31
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Gln Met Thr Gln Ser Pro Ser Ser Val Ser Ala Ser Val Gly
1               5                   10                  15

Asp Arg Val Ser Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Thr Pro Pro
                85                  90                  95

Thr Phe Gly Gln Gly Thr Lys Leu Glu Ile Lys
            100                 105

<210> SEQ ID NO 32
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Gln Glu Ser Gly Pro Gly Leu Val Lys Pro Ser Glu
1               5                   10                  15

Thr Leu Ser Leu Thr Cys Ser Val Ser Gly Val Ser Ile Ser Asp Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Thr Ser Gly Trp Ser Gly Gly Ala Phe Asp Ile Trp Gly Gln
            100                 105                 110

Gly Thr Met Val Thr Val Ser Ser
        115                 120

<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Ile Val Leu Thr Gln Ser Pro Asn Ser Leu Ala Val Ser Leu Gly
1               5                   10                  15

Glu Arg Ala Thr Ile Arg Cys Lys Ser Ser Gln Ser Val Leu Tyr Ser
            20                  25                  30

Gly Asn Asn Lys Asn Tyr Ile Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Glu Thr Asp Phe Thr Leu Thr
65                  70                  75                  80

Ile Ser Ser Leu Arg Ala Glu Asp Val Ala Leu Tyr Tyr Cys Gln Gln
                85                  90                  95

Tyr Tyr Ser Arg Trp Thr Phe Gly Gln Gly Thr Lys Leu Glu Ile Lys
            100                 105                 110

<210> SEQ ID NO 34
<211> LENGTH: 120
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 34

Glu Val Gln Leu Val Arg Ser Gly Gly Asn Leu Val Gln Pro Gly Gly
1               5                   10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
        35                  40                  45

Asn Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65                  70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Val Met Thr Gln Ser Pro Ser Ser Leu Ser Ala Ser Val Gly
1               5                   10                  15

Asp Arg Val Thr Ile Ser Cys Arg Ala Ser Gln Ser Ile Arg His Tyr
            20                  25                  30

Val Asn Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Tyr Ser Ile Pro Leu
                85                  90                  95

Thr Phe Gly Gly Gly Thr Lys Val Glu Ile Lys
            100                 105

<210> SEQ ID NO 36
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

-continued

```
Pro Met Ser Trp Val Arg Gln Ala Pro Gly Lys Gly Leu Ala Trp Val
        35                  40                  45
Ser Ser Leu Thr Ala Ser Gly Asp Asn Thr Phe Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met His Ser Leu Arg Ala Glu Asp Thr Ala Val Tyr Tyr Cys
                85                  90                  95
Ala Lys Ala Leu Val Gly Arg Tyr Asp Ile Ser Thr Gly Tyr Tyr Arg
            100                 105                 110
Pro Val Met Asp Ser Trp Gly Gln Gly Thr Leu Val Thr Val Ser Ser
        115                 120                 125
```